US011510875B2

(12) United States Patent
Fox et al.

(10) Patent No.: US 11,510,875 B2
(45) Date of Patent: Nov. 29, 2022

(54) ADJUVANT FORMULATIONS COMPRISING TLR4 AGONISTS AND METHODS OF USING THE SAME

(71) Applicant: ACCESS TO ADVANCED HEALTH INSTITUTE, Seattle, WA (US)

(72) Inventors: Christopher Fox, Sumner, WA (US); Steven G. Reed, Bellevue, WA (US); Susan Baldwin, Seattle, WA (US); Thomas Vedvick, Federal Way, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

(21) Appl. No.: 14/377,488

(22) PCT Filed: Feb. 7, 2013

(86) PCT No.: PCT/US2013/025204
§ 371 (c)(1),
(2) Date: Aug. 7, 2014

(87) PCT Pub. No.: WO2013/119856
PCT Pub. Date: Aug. 15, 2013

(65) Prior Publication Data
US 2015/0017191 A1   Jan. 15, 2015

Related U.S. Application Data

(60) Provisional application No. 61/596,066, filed on Feb. 7, 2012.

(51) Int. Cl.
| A61K 9/113 | (2006.01) |
| A61K 39/39 | (2006.01) |
| A61K 39/015 | (2006.01) |
| A61K 39/12 | (2006.01) |
| A61K 9/107 | (2006.01) |
| A61K 47/06 | (2006.01) |
| A61K 39/00 | (2006.01) |
| A61K 47/24 | (2006.01) |
| A61K 47/26 | (2006.01) |

(52) U.S. Cl.
CPC .............. *A61K 9/113* (2013.01); *A61K 9/107* (2013.01); *A61K 39/00* (2013.01); *A61K 39/015* (2013.01); *A61K 39/12* (2013.01); *A61K 39/39* (2013.01); *A61K 47/06* (2013.01); *A61K 47/24* (2013.01); *A61K 47/26* (2013.01); *A61K 2039/55566* (2013.01); *A61K 2039/55572* (2013.01); *C12N 2760/16134* (2013.01); *C12N 2760/16234* (2013.01)

(58) Field of Classification Search
CPC .......... A61K 2039/55572; A61K 39/00; A61K 39/015; A61K 39/12; A61K 39/39; A61K 47/06; A61K 47/24; A61K 47/26; A61K 9/107; A61K 9/113; A61K 2039/55566; C12N 2760/16134; C12N 2760/16234
See application file for complete search history.

(56) References Cited

U.S. PATENT DOCUMENTS

| 3,238,190 | A | 3/1966 | Erbring et al. |
| 3,598,122 | A | 8/1971 | Zaffaroni |
| 3,598,123 | A | 8/1971 | Zaffaroni |
| 4,286,592 | A | 9/1981 | Chandrasekaran |
| 4,314,557 | A | 2/1982 | Chandrasekaran |
| 4,379,454 | A | 4/1983 | Campbell et al. |
| 4,420,461 | A | 12/1983 | Reckel et al. |
| 4,420,558 | A | 12/1983 | De Mey et al. |
| 4,436,727 | A | 3/1984 | Ribi |
| 4,568,343 | A | 2/1986 | Leeper et al. |
| 4,595,654 | A | 6/1986 | Reckel et al. |
| 4,614,722 | A | 9/1986 | Pasula |
| 4,659,659 | A | 4/1987 | Dwek et al. |
| 4,743,540 | A | 5/1988 | Ralph et al. |
| 4,767,402 | A | 8/1988 | Kost et al. |
| 4,769,330 | A | 9/1988 | Paoletti et al. |
| 4,780,212 | A | 10/1988 | Kost et al. |
| 4,897,268 | A | 1/1990 | Tice et al. |
| 4,912,094 | A | 3/1990 | Myers et al. |
| 4,948,587 | A | 8/1990 | Kost et al. |
| 4,981,684 | A | 1/1991 | MacKenzie et al. |
| 5,017,487 | A | 5/1991 | Stunnenberg et al. |
| 5,057,540 | A | 10/1991 | Kensil et al. |

(Continued)

FOREIGN PATENT DOCUMENTS

| CN | 1306438 A | 8/2001 |
| EP | 0 366 412 A2 | 5/1990 |

(Continued)

OTHER PUBLICATIONS

ICI Americas, "The HLB System" (1980) pp. 1-22.*
Fox et al., Endotoxins: Structure, Function and Recognition, Subcellular Biochemistry, 53: 303-321 (2010).*
Fox et al., AAPS PharmSci Tech, 12:498-506 (2012).*
Hippalgaonkar, K. et al. (2010) "Injectable Lipid Emulsions-Advancements, Opportunities and Challenges" AAPS Pharmscitech, 11(4): 1526-1540.
Reed S.G. (2009). "New Adjuvants For Prophylactic and Therapeutic Vaccines, New Cells For New Vaccines IV," pp. 1-57.
Akamatsu et al., "Synthesis of lipid A monosaccharide analogues containing acidic amino acid: Exploring the structural basis for the endotoxic and antagonistic activities," *Bioorganic & Medicinal Chemistry* 14:6759-6777, 2006.

(Continued)

Primary Examiner — Matthew P Coughlin
Assistant Examiner — Thurman Wheeler
(74) Attorney, Agent, or Firm — Benjamin A. Keim; Newport IP, LLC

(57) ABSTRACT

Formulations and methods, including vaccines and pharmaceutical compositions for inducing or enhancing an immune response are disclosed. The formulations generally comprise a TLR4 agonist and a metabolizable oil at a concentration of about 0.01%-1% v/v, wherein the hydrophobic:lipophilic balance (HLB) of the emulsion is greater than about 9.

61 Claims, 22 Drawing Sheets

(56) References Cited

U.S. PATENT DOCUMENTS

Figure 2G:
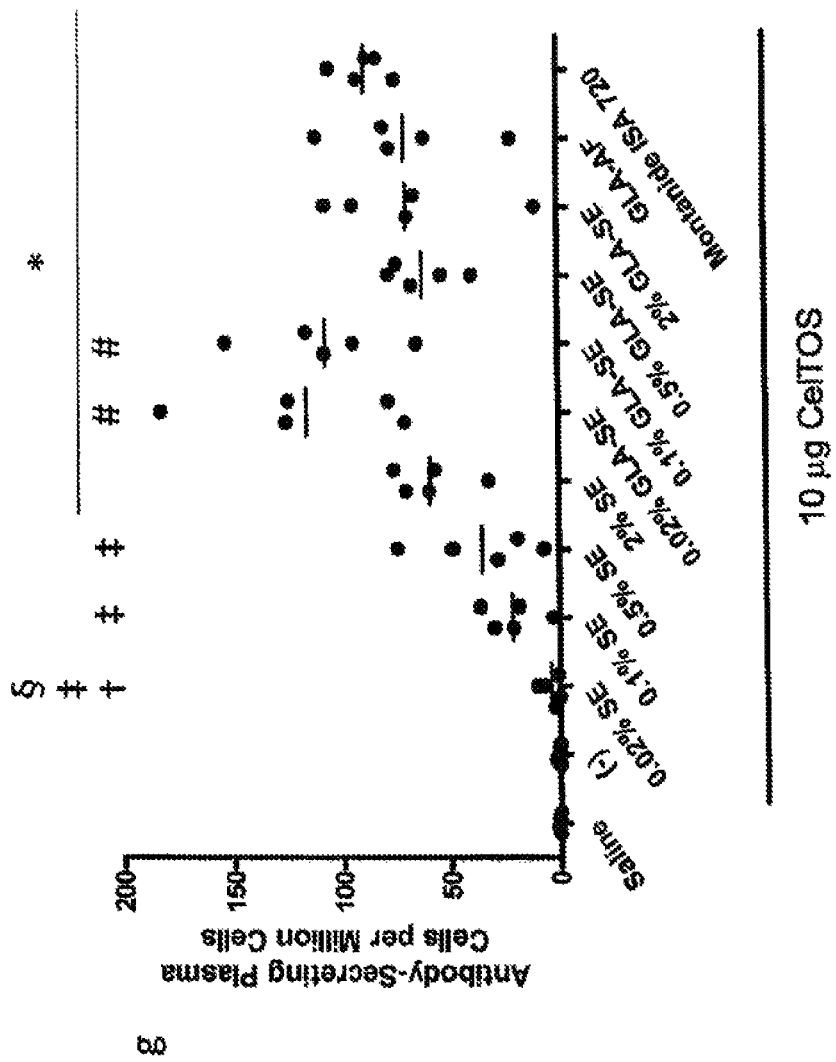

| | | |
|---|---|---|
| 5,075,109 A | 12/1991 | Tice et al. |
| 5,124,141 A | 6/1992 | Makler |
| 5,147,785 A | 9/1992 | Pasula |
| 5,162,990 A | 11/1992 | Odeyale et al. |
| 5,231,168 A | 7/1993 | Dziegiel et al. |
| 5,278,302 A | 1/1994 | Caruthers et al. |
| 5,298,396 A | 3/1994 | Kotzin et al. |
| 5,411,865 A | 5/1995 | Reed |
| 5,422,109 A | 6/1995 | Brancq et al. |
| 5,424,067 A | 6/1995 | Brancq et al. |
| 5,457,041 A | 10/1995 | Ginaven et al. |
| 5,464,387 A | 11/1995 | Haak et al. |
| 5,565,209 A | 10/1996 | Rijke |
| 5,591,139 A | 1/1997 | Lin et al. |
| 5,595,888 A | 1/1997 | Gray et al. |
| 5,618,275 A | 4/1997 | Bock |
| 5,654,140 A | 8/1997 | Persico et al. |
| 5,656,016 A | 8/1997 | Ogden |
| 5,666,153 A | 9/1997 | Copeland |
| 5,693,531 A | 12/1997 | Chiorini et al. |
| 5,719,263 A | 2/1998 | Reed |
| 5,722,397 A | 3/1998 | Eppstein |
| 5,786,148 A | 7/1998 | Bandman et al. |
| 5,795,577 A | 8/1998 | Kieny et al. |
| 5,840,871 A | 11/1998 | Hillman et al. |
| 5,843,464 A | 12/1998 | Bakaletz et al. |
| 5,846,758 A | 12/1998 | Medenica |
| 5,885,211 A | 3/1999 | Eppstein et al. |
| 5,912,166 A | 6/1999 | Reed et al. |
| 5,955,306 A | 9/1999 | Gimeno et al. |
| 5,981,215 A | 11/1999 | Meissner et al. |
| 5,993,800 A | 11/1999 | Linsley et al. |
| 6,018,678 A | 1/2000 | Mitragotri et al. |
| 6,027,732 A | 2/2000 | Morein et al. |
| 6,033,928 A | 3/2000 | Eriguchi et al. |
| 6,057,427 A | 5/2000 | Smith et al. |
| 6,106,824 A | 8/2000 | Kaplitt et al. |
| 6,110,492 A * | 8/2000 | Alving ................ A61K 9/127 424/450 |
| 6,120,769 A | 9/2000 | Gefter et al. |
| 6,218,186 B1 | 4/2001 | Choi et al. |
| 6,231,861 B1 | 5/2001 | Barnwell |
| 6,261,762 B1 | 7/2001 | Alizon et al. |
| 6,309,847 B1 | 10/2001 | Cohen et al. |
| 6,316,183 B1 | 11/2001 | Alizon et al. |
| 6,322,532 B1 | 11/2001 | D'Sa et al. |
| 6,375,944 B1 | 4/2002 | Trinchieri et al. |
| 6,472,515 B1 | 10/2002 | Climent-Johansson et al. |
| 6,512,102 B1 | 1/2003 | Xu et al. |
| 6,544,518 B1 | 4/2003 | Friede et al. |
| 6,544,728 B1 | 4/2003 | Alizon et al. |
| 6,555,653 B2 | 4/2003 | Alderson et al. |
| 6,587,792 B1 | 7/2003 | Thomas |
| 6,596,501 B2 | 7/2003 | Roth |
| 6,613,892 B2 | 9/2003 | Preston et al. |
| 6,630,161 B1 * | 10/2003 | Leesman ................ A61K 39/39 424/283.1 |
| 6,654,462 B1 | 11/2003 | Hedberg |
| 6,660,487 B2 | 12/2003 | Faustman |
| 6,676,961 B1 | 1/2004 | Lichter |
| 6,682,901 B2 | 1/2004 | Blaschuk et al. |
| 6,685,699 B1 | 2/2004 | Eppstein et al. |
| 6,692,752 B1 | 2/2004 | Slaoui et al. |
| 6,706,872 B1 | 3/2004 | Barnwell |
| 6,713,068 B1 | 3/2004 | Audonnet et al. |
| 6,733,763 B2 | 5/2004 | Raychaudhuri et al. |
| 6,734,172 B2 | 5/2004 | Scholler et al. |
| 6,749,856 B1 | 6/2004 | Berzofsky et al. |
| 6,752,995 B2 | 6/2004 | Johnston et al. |
| 6,770,445 B1 | 8/2004 | Scholler et al. |
| 6,783,981 B1 | 8/2004 | Uden et al. |
| 6,797,276 B1 | 9/2004 | Glenn et al. |
| 6,844,192 B2 | 1/2005 | Orlando et al. |
| 6,846,489 B1 | 1/2005 | Garcon et al. |
| 6,846,648 B2 | 1/2005 | Maes |
| 6,855,322 B2 | 2/2005 | Lyon et al. |
| 6,869,607 B1 | 3/2005 | Buschle et al. |
| 6,871,477 B1 | 3/2005 | Tucker |
| 6,875,610 B2 | 4/2005 | Higginbotham et al. |
| 6,893,820 B1 | 5/2005 | Plass |
| 6,908,453 B2 | 6/2005 | Fleming et al. |
| 6,919,078 B2 | 7/2005 | Ni et al. |
| 6,919,210 B1 | 7/2005 | Okamoto |
| 6,929,796 B1 | 8/2005 | Conti-Fine |
| 6,932,972 B2 | 8/2005 | Stephenne et al. |
| 6,933,123 B2 | 8/2005 | Hu et al. |
| 6,936,255 B1 | 8/2005 | Wettendorff |
| 6,949,246 B2 | 9/2005 | Reed et al. |
| 6,969,704 B1 | 11/2005 | Pinsky et al. |
| 6,970,739 B1 | 11/2005 | Inoue |
| 6,974,588 B1 | 12/2005 | Miranda et al. |
| 6,977,073 B1 | 12/2005 | Cezayirli et al. |
| 6,979,535 B2 | 12/2005 | Alizon et al. |
| 6,979,730 B2 | 12/2005 | Reiter et al. |
| 6,991,791 B2 | 1/2006 | Le et al. |
| 7,001,770 B1 | 2/2006 | Atencio et al. |
| 7,008,774 B2 | 3/2006 | Ryan et al. |
| 7,012,134 B2 | 3/2006 | Ruben et al. |
| 7,018,345 B2 | 3/2006 | Mori et al. |
| 7,029,678 B2 | 4/2006 | Momin et al. |
| 7,029,685 B2 | 4/2006 | Lanar et al. |
| 7,030,232 B1 | 4/2006 | Reiter et al. |
| 7,033,598 B2 | 4/2006 | Lerner |
| 7,037,712 B2 | 5/2006 | Both et al. |
| 7,052,904 B2 | 5/2006 | Zheng et al. |
| 7,060,276 B2 | 6/2006 | Lanar et al. |
| 7,060,802 B1 | 6/2006 | Trakht et al. |
| 7,067,310 B2 | 6/2006 | Chartier et al. |
| 7,070,931 B2 | 7/2006 | Fujinaga et al. |
| 7,078,180 B2 | 7/2006 | Genetta |
| 7,084,256 B2 | 8/2006 | McCormick et al. |
| 7,087,231 B2 | 8/2006 | Guerin-Marchand et al. |
| 7,087,713 B2 | 8/2006 | Campos-Neto et al. |
| 2003/0215497 A1 | 11/2003 | Leesman |
| 2007/0021017 A1 | 1/2007 | Derin-Holzapfel |
| 2007/0191314 A1* | 8/2007 | Klucker et al. ............... 514/102 |
| 2008/0131466 A1 | 6/2008 | Reed et al. |
| 2009/0010959 A1* | 1/2009 | Biemans ................ A61P 27/14 424/197.11 |
| 2009/0045033 A1 | 2/2009 | Hausladen |
| 2010/0037466 A1 | 2/2010 | Rowlay et al. |
| 2010/0129391 A1 | 5/2010 | Reed et al. |
| 2010/0310602 A1 | 12/2010 | Reed et al. |
| 2011/0014274 A1* | 1/2011 | Reed et al. ................... 424/450 |
| 2011/0305748 A1 | 12/2011 | Clegg et al. |

FOREIGN PATENT DOCUMENTS

| | | |
|---|---|---|
| EP | 0 399 843 A2 | 11/1990 |
| EP | 0 399 843 A3 | 11/1990 |
| EP | 0 399 843 B1 | 11/1990 |
| EP | 0 109 942 A2 | 3/1991 |
| EP | 0 468 520 A2 | 1/1992 |
| EP | 0 382 271 B1 | 12/1994 |
| EP | 0 198 474 B1 | 6/1996 |
| EP | 0 414 374 B1 | 10/1997 |
| EP | 0 362 279 B2 | 11/1999 |
| EP | 0 304 578 B1 | 10/2001 |
| GB | 2232892 | 1/1991 |
| JP | 2013-70426 A | 4/2013 |
| WO | WO-89/01973 A2 | 3/1989 |
| WO | WO-89/01973 A3 | 3/1989 |
| WO | WO-90/01496 A1 | 2/1990 |
| WO | WO-90/06951 A1 | 6/1990 |
| WO | WO-90/07936 A1 | 7/1990 |
| WO | WO-91/00106 A1 | 1/1991 |
| WO | WO-91/00107 A1 | 1/1991 |
| WO | WO-91/02805 A2 | 3/1991 |
| WO | WO-91/02805 A3 | 3/1991 |
| WO | WO-93/02184 A1 | 2/1993 |
| WO | WO-93/03709 A1 | 3/1993 |
| WO | WO-93/10152 A1 | 5/1993 |
| WO | WO-93/25234 A1 | 12/1993 |
| WO | WO-93/25698 A1 | 12/1993 |

(56) References Cited

FOREIGN PATENT DOCUMENTS

| WO | WO-94/00152 A1 | 1/1994 |
|---|---|---|
| WO | WO-94/00153 A1 | 1/1994 |
| WO | WO-94/03622 A1 | 2/1994 |
| WO | WO-94/05792 A1 | 3/1994 |
| WO | WO-94/20137 A1 | 9/1994 |
| WO | WO-95/17209 A1 | 6/1995 |
| WO | WO-95/17210 A1 | 6/1995 |
| WO | WO-95/20600 A1 | 8/1995 |
| WO | WO-95/26204 A1 | 10/1995 |
| WO | WO-96/02555 A1 | 2/1996 |
| WO | WO-96/11272 A2 | 4/1996 |
| WO | WO-96/11272 A3 | 4/1996 |
| WO | WO-96/11711 A1 | 4/1996 |
| WO | WO-96/26277 A1 | 8/1996 |
| WO | WO-96/33739 A1 | 10/1996 |
| WO | WO-98/12302 A1 | 3/1998 |
| WO | WO-98/16247 A1 | 4/1998 |
| WO | WO-98/20117 A1 | 5/1998 |
| WO | WO-98/56414 A1 | 12/1998 |
| WO | WO-99/03884 A2 | 1/1999 |
| WO | WO-99/03884 A3 | 1/1999 |
| WO | WO 99/10008 A1 | 3/1999 |
| WO | WO-99/010375 A2 | 3/1999 |
| WO | WO-99/010375 A3 | 3/1999 |
| WO | WO-99/11241 A1 | 3/1999 |
| WO | WO-99/12565 A1 | 3/1999 |
| WO | WO-99/17741 A1 | 4/1999 |
| WO | WO-99/40188 A2 | 8/1999 |
| WO | WO-99/40188 A3 | 8/1999 |
| WO | WO-99/51748 A2 | 10/1999 |
| WO | WO-99/51748 A3 | 10/1999 |
| WO | WO-99/53061 A2 | 10/1999 |
| WO | WO-00/04149 A2 | 1/2000 |
| WO | WO-2008/124647 A2 | 10/2008 |
| WO | WO-2008/124647 A3 | 10/2008 |
| WO | WO-2008/153541 A1 | 12/2008 |

OTHER PUBLICATIONS

Andaloussi et al., (2006). "Stimulation of TLR9 with CpG ODN Enhances Apoptosis of Glioma and Prolongs the Survival of Mice with Experimental Brain Tumors," *Glia* 54(6):526-535.

Anderson R.C. et al. (2010). Physicochemical characterization and biological activity of synthetic TLR4 agonist formulations. *Coll Surf B: Biointerfaces* 75:123-32.

Anonymous. (Nov. 1995). "Standards for the diagnosis and care of patients with chronic obstructive pulmonary disease. American Thoracic Society," *Am. J. Respir. Crit. Care Med.* 152(5 Pt. 2):S77-121.

Armant, M.A. et al. (2002). "Toll-Like Receptors: A Family of Pattern-Recognition Receptors in Mammals," *Genome Biol.* 3(8): 3011.I-3011.6.

Badaro et al., "Evaluation of Micro Enzyme-linked Immunosorbent Assay (ELISA) for Antibodies in American Visceral Leishmaniasis: Antigen Selection for Detection of Infection-Specific Responses," *Am. J Trop. Med. Hyg.* 35:72-78, 1986.

Badaro et al., "rK39: A Cloned Antigen of Leishmania Chagasi that Predicts Active Visceral Leishmaniasis," *J Inf Dis.* 173(3):758-761, Mar. 1996.

Baldwin S.L. et al. (2009). "Enhanced humoral and Type 1 cellular immune responses with Fluzone adjuvanted with a synthetic TLR4 agonist formulated in an emulsion," *Vaccine*: 27:5956-5963.

Bomford, R. et al., "Adjuvanticity and ISCOM Formation by Structurally Diverse Saponins," *Vaccine* 10(9):572-577, 1992.

Baudner, B.C. et al. (2009). MF59 emulsion is an effective delivery system for a synthetic TLR4 agonist (E6020). *Pharm Res.* 26:1477-1485.

Bayes, M. et al., "Gateways to clinical trials." *Methods Find. Exp. Clin. Pharmacol.* Apr. 2005 27(3):193-219.

Berkner, K.L. (1988). "Development of Adenovirus Vectors for the Expression of Heterologous Genes," *Biotechniques* 6:616-627.

Beutler, B. et al. (1986). "Cachectin and Tumour Necrosis Factor as Two Sides of the Same Biological Coin," *Nature* 320:584-588.

Bergmann-Leitner, E.S. et al. (Aug. 2010). Immunization with pre-erythrocytic antigen CelTOS from *Plasmodium falciparum* elicits cross-species protection against heterologous challenge with *Plasmodium berghei. PLoS One* 5(8):e12294, 9 pages.

Bergmann-Leitner, E.S. et al. (2011). "Cellular and humoral immune effector mechanisms required for sterile protection against sporozoite challenge induced with the novel malaria vaccine candidate CelTOS," *Vaccine* 29:5940-5949.

Bibette J. et al. (1992). "Stability criteria for emulsions," *Phys Rev Lett.* 69(16):2439-2442.

Bock, T.K. et al. (Apr. 1994). "A novel assay to determine the hemolytic activity of drugs incorporated in colloidal carrier systems," *Phann Res.* 11(4):589-591.

Bray, R.S. et al. (1966) "The Immunology and Serology of Leishmanisis," *Trans. R. Soc. Trop. Med. Hyg.* 60:605-609.

Brazolot-Millan, C.L. et al. (1998). "CpG DNA Can Induce Strong Th1 Humoral and Cell-Mediated Immune Responses Against Hepatitis B Surface Antigen in Young Mice," *Proc. Natl. Acad. Sci. USA* 95(26):15553-15558.

Brito L.A. et al. (2011). Alternative renewable source of squalene for use in emulsion adjuvants. *Vaccine* 29:6262-6268.

Capek I. (2004). "Degradation of kinetically-stable o/w emulsions," *Adv. Coll. Inter. Sci.* 107(2-3):125-155.

Chen, L. et al. (2006). "District Responses of Lung and Spleen Dendritic Cells to the TLR9 Agonist CpG Oligodeoxynucleotide," *J. Immunol.* 177:2373-2383.

Choudhry, A. et al. (1990). "Enzyme-Linked Immunosorbent Assay in the Diagnosis of Lala-Azar in Bhadohi (Varanasi) India," *Trans. R. Soc. Trop. Med. Hyg.* 84:363-366.

Choudhry, A. et al. (1992). "An Indirect Fluorescent Antibody (IFA) Test for the Serodiagnosis of Kala-Azar," *J. Comm. Dis.* 24:32-36.

Cioppa, G.D. et al. (2011). "Trivalent and quadrivalent MF59-adjuvanted influenza vaccine in young children: A dose-and schedulefinding study," *Vaccine* 29:8696-8704.

Coler, R.N. et al. (2011). "Development and characterization of synthetic glucopyranosyl lipid adjuvant system as a vaccine adjuvant," PLoS ONE 6:e16333.

Cooper, C.L. et al. (Sep. 2005). "CPG 7909 adjuvant improves hepatitis B virus vaccine seroprotection in antiretroviral-treated HIV-infected adults." *AIDS* 19(14):1473-1479.

Correale, P. et al. (1997). "In Vitro Generation of Human Cytotoxic T Lymphocytes Specific for Peptides Derived From Prostate-Specific Antigen," *Journal of the National Cancer Center* 89:293-299.

Cotten, M. et al. (Jul. 1992). "High-Efficiency Receptor-Mediated Delivery of Small and Large (48 Kilobase Gene Constructs Using the Endosome-Disruption Activity of Defective or Chemically Inactivated Adenovirus Particles," *Proc. Natl. Acad. Sci. USA* 89:6094-6098.

Curiel, D.T. et al. (1992). "High-Efficiency Gene Transfer Mediated by Adenovirus Coupled to DNA-Polylysine Complexes," *Hum. Gene Ther.* 3:147-154.

Dalgleish, D.G. (1997). "Adsorption of protein and the stability of emulsions," *Trends Food Sci Tech.* 8(1):1-6.

Datta et al., "A Subset of Toll-Like Receptor Ligands Induces Cross-Presentation by Bone Marrow-Derived Dendritic Cells," *J Immunol.* 170(8):4102-4110, Apr. 2003.

Davis et al., "CpG DNA is a Potent Enhancer of Specific Immunity in Mice Immunized with Recombinant Hepatitis B Surface Antigen," *J Immunol.* 160(2):870-876, Jan. 1998.

DeMan J.M. Chemical and physical properties of fatty acids. In: Chow CK, editor. Fatty Acids in Foods and their Health Implications. Boca Raton, FL: CRC Press; 2008. p. 17-46.

Deng et al., "CpG Oligodeoxynucleotides Stimulate Protective Innate Immunity Against Pulmonary *Klebsiella* Infection," *J Immunol.* 173:5148-5155,2004.

Edelman, "Vaccine Adjuvants," *Rev. Infect. Dis.* 2(3):370-83, May-Jun. 1980.

Edelman, "The Development and Use of Vaccine Adjuvants," *Mol. Biotechnol.* 21(2):129-148, Jun. 2002.

(56) References Cited

OTHER PUBLICATIONS

El-On et al., "Leishmania Donovani: Physicochemical, Immunological, and Biological Characterization of Excreted Factor from Promastigotes," *Exper. Parasitol.* 47(2):254-269, Apr. 1979.
Falsey, A.R. (2008). "Half-dose influenza vaccine," *Arch Intern Med.* 168:2402-2403.
Fearon et al., "The Instructive Role of Innate Immunity in the Acquired Immune Response," *Science* 272(5258):50-54, Apr. 5, 1996.
Felgner et al., "Lipofection: A Highly Efficient, lipid-mediated DNA-Transfection Procedure," *Proc. Natl. Acad. Sci. USA* 84(21):7413-7417, Nov. 1987.
Feuillet et al., "Involvement of Toll-like Receptor 5 in the Recognition of Flagellated Bacteria," *PNAS* 103(33):12487-12492, Aug. 15, 2006.
Forchielli, M. L. et al. (2010). "The spectrum of plant and animal sterols in different oil-derived intravenous emulsions," *Lipids* 45:63-71.
Fox, C.B. et al. (2007). "Detecting phase transitions in phosphatidylcholine vesicles by Raman microscopy and self-modeling curve resolution," *J Phys Chem B*. 111(39):11428-11436.
Fox, C.B. et al. (Aug. 2008). "Monitoring the effects of component structure and source and formulation stability and adjuvant activity of oil-in-water emulsions," *Coll Surf B: Biointerfaces* 65:98-105.
Fox, C. B. (2009). Squalene emulsions for parenteral vaccine and drug delivery, *Molecules* 14:3286-3312.
Fox, C. B. (2011). "Immunomodulatory and physical effects of oil composition in vaccine adjuvant emulsions," *Vaccine* 29:9563-9572.
Fox, C. B. et al. (2011). "Effects of emulsifier concentration, composition, and order of addition in squalene-phosphatidylcholine oil-in-water emulsions," *Pharm Dev Technol.* 16:511-519.
Frey A. et al. (1998). "A statistically defined endpoint titer determination method for immunoassays," J Immunological Methods 221:35-41.
Gibson et al., "Plasmacytoid Dendritic Cells Produce Cytokines and Mature in Response to the TLR7 Agonists, Imiquimod and Resiquimod," *Cell. Immunol.* 218(1-2):74-86, Jul.-Aug. 2002.
Gisvold, "Digitonin and Phytosterol from the Seed of Digitalis Purpurea," *Phytochem. Notes, Amer. Pharmacol. Assoc.* 23(7):664-666, Jul. 1934.
Glück, "Immunopotentiating Reconstituted Influenza Virosomes (IRIVs) and other Adjuvants for Improved Presentation of Small Antigens," *Vaccine* 10(13):915-919, 1992.
Gorden et al., "Synthetic TLR Agonists Reveal Functional Differences Between Human TLR7 and TLR8," *J Immunol.* 174:1259-1268,2005.
Green et al., "Mitochondria and Apoptosis," *Science* 281 (5381):1309-1312, Aug. 28, 1998.
Hemmi et al., "Small Anti-Viral Compounds Activate Immune Cells Via the TLR7 MyD88-Dependent Signaling Pathway," *Nat. Immunol.* 3(2):196-200, Feb. 2002.
Hilleman M.R. (1999). Personal historical chronicle of six decades of basic and applied research in virology, immunology, and vaccinology. *Immunol Rev.* 170:7-27.
Horsmans et al., "Isatoribine, an Agonist of TLR7, Reduces Plasma Virus Concentration in Chronic Hepatitis C Infection," *Hepatol.* 42(3):724-731, Sep. 2005.
Hubert et al., "STEAP: A Prostate-Specific Cell-Surface Antigen Highly Expressed in Human Prostate Tumors," *PNAS* 96(25):14523-14528, Dec. 7, 1999.
International Search Report dated Apr. 16, 2013, for PCT/US2013/025204, filed on Feb. 7, 2013, 2 pages.
Jacobson et al., "Epidemiology and Estimated Population Burden of Selected Autoimmune Diseases in the United States,"*Clin. Immunol. Immunopathol.* 84(3):223-243, Sep. 1997.
Johansen et al., "Toll-Like Receptor Ligands as Adjuvants in Allergen-Specific Immunotherapy," *Clin. Exp. Allerg* 35(12):1591-1598, Dec. 2005.

Kabalnov A. et al. (1996). "Phospholipids as emulsion stabilizers: phase behavior versus emulsion stability," *J Coll Inter Sci.* 184:227-235.
Kaisho et al., "Pleiotropic Function of Toll-like Receptors," *Microbes Infect.* 6(15):1388-1394, Dec. 2004.
Keitel W. et al. (2010). Dose ranging of adjuvant and antigen in a cell culture H5NI influenza vaccine: Safety and immunogenicity of a phase 1/2 clinical trial. *Vaccine* 28:840-848.
Kensil et al., "Separation and Characterization of Saponins with Adjuvant Activity from Quillaja Saponaria Molina Cortex," *J Immunology* 146(2):431-437, Jan. 15, 1991.
Kensil, "Saponins as Vaccine Adjuvants," *Crit. Rev. Then Drug Carrier Syst.* 13(1-2): 1-55, 1996.
Kolls et al., "Prolonged and Effective Blockade of Tumor Necrosis Factor Activity Through Adenovirus-Mediated Gene Transfer," *Proc. Natl. Acad. Sci. USA* 91:215-219, Jan. 1994.
Krieg, A.M. et al. (Apr. 6, 1995). "CpG motifs in bacterial DNA trigger direct B-cell activation," *Nature* 374(6522):546-549.
Kriegler et al., "A Novel Form of TNF/Cachectin is a Cell Surface Cytotoxic Transmembrane Protein: Ramifications for the Complex Physiology of TNF," *Cell* 53(1):45-53, Apr. 8, 1988.
Lacaille-Dubois et al., "A Review of the Biological and Pharmacological Activities of Saponins," *Phytomedicine* 2(4):363-386, 1996.
Langley J.M. et al. "Safety and cross-reactive immunogenicity of candidate AS03-adjuvanted prepandemic H5NI influenza vaccines: A randomized controlled phase 1/2 trial in adults," *J Infect Dis* 2010: 201:1644-1653.
Lee et al., "Activation of Anti-Hepatitis C Virus Responses Via Toll-Like Receptor 7," *Proc. Nat. Acad. Sci. USA* 103(6):1828-1833, Feb. 7, 2006.
Li et al., "Assessment of Recombinant Adenoviral Vectors for Hepatic Gene Therapy," *Hum. Gene Ther*. 4(4):403-409, Aug. 1993.
Lien et al., "Adjuvants and Their Signaling Pathways: Beyond TLRs," *Nat. Immunol.* 4(12): 1162-1164, Dec. 2003.
Lin et al., "Implication of Toll-Like Receptor and Tumor Necrosis Factor Alpha Signaling in Septic Shock," *Shock* 24(3):206-209, Sep. 2005.
Lu et al., "A Novel Gene (PLU-1) Containing Highly Conserved Putative DNA/Chromatin Binding Motifs is Specifically Up-Regulated in Breast Cancer," *J Biol. Chem.* 274(22):15633-15645, May 28, 1999.
Luster, "The Role of Chemokines in Linking Innate and Adaptive Immunity," *Curr. Opin. Immunol.* 14(1):129-135, Feb. 2002.
McClements D.J. (2007). "Critical review of techniques and methodologies for characterization of emulsion stability," *Crit Rev Food Sci Nutri.* 47:611-649.
McCluskie et al., "CpG DNA is a Potent Enhancer of Systemic and Mucosal Immune Responses Against Hepatitis B Surface Antigen with Intranasal Administration to Mice," *J Immunol.* 161(9):4463-4466, Nov. 1998.
Medzhitov et al., "Innate Immunity: Impact on the Adaptive Immune Response," *Curr. Opin. Immunol.* 9(1):4-9, Feb. 1997.
Medzhitov, "Toll-Like Receptors and Innate Immunity," *Nat. Rev. Immunol.* 1(2):135-145, Nov. 2001.
Merck Index, Twelfth Edition, Entry 3737, "Escin" p. 628, 1996.
Mikrut B. Case study: formulation of an intravenous fat emulsion. In: Burgess DJ, editor. Injectable Dispersed Systems: Formulation, Processing, and Performance. Boca Raton, FL: Taylor and Francis; 2005. p. 415-425.
Mitchell et al., "Expression of the Pneumolysin Gene in *Escherichia coli*: Rapid Purification and Biological Properties," *Biochem. Biophys. Acta* 1007:67-72, 1989.
Mologen AG (Berlin, FRG: located at < http://www.mologen.com/English/04.20-dSLIM.shtml> last visited Jan. 12, 2015, 2 pages.
Nakao et al., "Surface-Expressed TLR6 Participates in the Recognition of Diacylated Lipopeptide and Peptidoglycan in Human Cells," *J Immunol.* 174:1566-1573, 2005.
Nelson et al., "Molecular Cloning and Characterization of Prostase, an Androgen Regulated Serine Protease with Prostate-Restricted Expression," *Proc. Natl. Acad. Sci. USA* 96(6):3114-3119, Mar. 16, 1999.

(56) References Cited

OTHER PUBLICATIONS

Nii T. et al. (2004). "Properties of various phosphatidylcholines as emulsifiers or dispersing agents in microparticle preparations for drug carriers," *Coll Surf B: Biointerfaces* 39(1-2):57-63.
Ott G et al. (1995). "MF59: Design and evaluation of a safe and potent adjuvant for human vaccines," Chapter 10 in *Vaccine Design: The Subunit and Adjuvant Approach*. New York: Plenum Press,: 277-296.
Reddy L.H. et al. (2009). "Squalene: a natural triterpene for use in diseasemanagement and therapy," Adv Drug Del Rev. 61:1412-26.
Reed et al., "An Improved Serodiagnostic Procedure for Visceral Leishmaniasis," *Am. J Trap. Med. Hyg.* 43(6):632-639, Dec. 1990.
Reiter et al., "Prostate Stem Cell Antigen: A Cell Surface Marker Overexpressed in Prostate Cancer," *Proc. Nat. Acad. Sci. USA* 95(4):1735-1740, Feb. 17, 1998.
Robbins et al., "Human Tumor Antigens Recognized by T-Cells," *Curr. Opin. Immunol.* 8(5):628-636, Oct. 1996.
Rosenberg S.A. et al. (2010). "Different adjuvanticity of incomplete Freund' s adjuvant derived from beef or vegetable components in melanoma patients immunized with a peptide vaccine," J Immunother 33:626-629.
Rubins, J.B. et al. (Dec. 1998). "Pneumolysin in Pneumococcal Adherence and Colonization," *Microb. Pathog.* 25(6):337-342.
Ruhenstroth-Bauer et al. "Purification of digitonin," Hoppe-Seyler's Zeitschrift fur physiologische Chemie (1955), 302(2-3), 111-118 (translation of Summary only).
Salem et al., "The Adjuvant Effects of the Toll-Like Receptor 3 Ligand Polyinosinic-Cytidylic Acid Poly (I:C) on Antigen-Specific CD8+ T Cell Responses are Partially Dependent on NK Cells with the Induction of a Beneficial Cytokine Milieu," *Vaccine* 24(24):5119-5132, Jun. 12, 2006.
Salomon et al., "Cripto: A Novel Epidermal Growth Factor (EGF)-Related Peptide in Mammary Gland Development and Neoplasia," *BioEssays* 21(1):61-70, Jan. 1999.
Schirmbeck et al. "Antigenic Epitopes Fused to Cationic Peptide Bound to Oligonucleotides Facilitate Toll-Like Receptor 9-Dependent, but CD4+T Cell Help-Independent Priming of CD8+T Cells," *J. Immunol.* 171(10):5198-5207, Nov. 15, 2003.
Schmidt, M. et al. (Dec. 6, 2005). "MIDGE Vectors and dSLIM Immunomodulators: DNA-based Molecules for Gene Therapeutic Strategies," in *Modern Biopharmaceuticals*, vol. 1, Chapter 7, pp. 183-200.
Schmidt et al., "Cytokine and Ig-Production by CO-Containing Sequences with Phosphorodiester Backbone and Dumbbell Shape," *Allergy* 61(1):56-63, Jan. 2006.
Schnur et al., "Leishmania! Serotypes as Distinguished by the Gel Diffusion of Factors Excreted in Vitro and in Vivo," *Isrl. J Med. Sci.* 8(7):932-942, Jul. 1972.
Senaldi et al., "Serological Diagnosis of Visceral Leishmaniasis by a Dot-Enzyme Immunoassay for the Detection of a Leishmania Donovani-Related Circulating Antigen," *J Immunol. Methods* 193(1):9-15, Jun. 1996.
Sergeiev, V. P., et al., (1969) Med. Parasitol. 38:208-212. (Summary in English only).
Sethi, S. et al. (Apr. 2001). "Bacterial infection in chronic obstructive pulmonary disease in 2000: a state-of-the-art review," *Clin. Microbiol. Rev.* 14(2):336-363.
Smith et al., "The Active Form of Tumor Necrosis Factor is a Trimer," *J Biol. Chem.* 262(15):6951-6954, May 25, 1987.
Soboll et al., "Expression of Toll-Like Receptors (TLR) and Responsiveness to TLR Agonists by Polarized Mouse Uterine Epithelial Cells in Culture," *Biol. Reprod.* 75(1):131-139, Jul. 2006.
Takeda et al., "Toll-Like Receptors," *Ann. Rev. Immunol.* 21:335-376, 2003.
Takeda et al., "Toll-Like Receptors in Innate Immunity," *Int. Immunol.* 17(1):1-14, Jan. 2005.
Tanaka Y. et al. (1983). "Mechanism of human erythrocyte hemolysis induced by short-chain phosphatidylcholines and lysophosphatidylcholine." *J Biochem.* 94:833-840.

Tatulian S.A. (1983). "Effect of lipid phase transition on the binding of anions to dimyristoylphosphatidylcholine liposomes," *Biochim Biophys Acta*. 736:189-195.
Tatulian S.A. (1987). "Binding of alkaline-earth metal cations and some anions to phosphatidylcholine liposomes," *Eur J Biochem.* 170:413-420.
Triozzi et al., "Effects of a Beta-Human Chorionic Gonadotropin Subunit Immunogen Administered in Aqueous Solution with a Novel Nonionic Block Copolymer Adjuvant in Patients with Advanced Cancer," *Clin. Cancer Res.* 3(12 Pt 1):2355-2362, Dec. 1997.
Tsan et al., "Cytokine Function of Heat Shock Proteins," *Am. J Physiol. Cell Physiol.* 286(4):C739-C744, Apr. 2004.
Tsan et al., "Endogenous Ligands of Toll-Like Receptors," *J Leukoc. Biol.* 76(3):514-519, Sep. 2, 2004.
Van den Eynde et al., "Tumor Antigens Recognized by T-lymphocytes," *Int. J Clin. Lab. Res.* 27:81-86, 1997.
Vernooij E.A.A.M et al. (1998). "Rapid determination of acyl chain position in egg phosphatidylcholine by high performance liquid chromatography/electrospray mass spectrometry," *Rapid Comm Mass Spec.* 12:83-86.
Vernooij, E.A.A.M. et al. ( 2002). "RP-HPLC/ESI MS determination of acyl chain positions in phospholipids," *J Sep Sci.* 25:285-289.
Vincent et al., "Long-term Correction of Mouse Dystrophic Degeneration by Adenovirusmediated TransferofaMinidystrophinGene," *Nat. Genet.* 5(2):130-134, Oct. 1993.
Vollmer et al. "Immunopharmacology of CpG Oligodeoxynucleotides and Ribavirin," *Antimicrob. Agents Chemother.* 48(6):2314-2317, Jun. 2004.
Vollmer, "Progress in drug development of Immunostimulatory CpG oligodeoxynucleotide ligands for TLR9," *Exp. Opin. Biolog. Ther.* 5(5):673-682, May 2005.
Wang et al. "pH-sensitive Immunoliposomes Mediate Target-Cell-Specific Delivery and Controlled Expression of a Foreign Gene in Mouse," *Proc. Natl. Acad. Sci. USA* 84:7851-7855, Nov. 1987.
Wasylyk et al., "The Ets Family of Transcription Factors," *Eur. J Bioch.* 211 (1-2):7-18, Jan. 15, 1993.
Weeratna et al., "TLR Agonists as Vaccine Adjuvants: Comparison of CpG ODN and Resiquimod (R-848)," *Vaccine* 23(45):5263-5270, Nov. 2005.
Weihrauch et al., "Phase I/II Combined Chemoimmunotherapy with Carcinoembryonic Antigen-Derived HLA-A2-Restricted CAP-I Peptide and Irinotecan, 5-Fluorouracil, and Leucovorin in Patients with Primary Metastatic Colorectal Cancer," *Clin. Cancer Res.* 11(16):5993-6001, Aug. 15, 2005.
Written Opinion dated Apr. 16, 2013, for PCT/US2013/025204, filed on Feb. 7, 2013, 4 pages.
Wu et al., "Targeting Genes: Delivery and Persistent Expression of a Foreign Gene Driven by Mammalian Regulatory Elements in Vivo," *J Biol. Chem.* 264(29):16985-16987, Oct. 15, 1989.
Yang Y.W. et al. (2004). "Cell death induced by vaccine adjuvants containing surfactants," *Vaccine* 22: 1524-36.
Yasuda T. et al. (1977). "Immunogenicity of liposomal model membranes in mice: Dependence on phospholipid composition," *Proc Natl Acad Sci.* 74: 1234-1236.
Yeh et al., "Improving Protein Delivery from Microparticles Using Blends of Poly(DL Lactide Co-Glycolide) and Poly(Ethylene Oxide )-Poly(Propylene Oxide) Copolymers," *Pharm. Res.* 13(11):1693-1698, Nov. 1996.
Yoon J.K. et al. (1996). "Interfacial properties as stability predictors of lecithin-stabilized perfluorocarbon emulsions," *Pharm Dev Tech.* 1(4):333-341.
Yoshikawa M, et al., "Bioactive Saponins and Glycosides. III. Horse Chestnut. (1 ): The Structures, Inhibitory Effects on Ethanol Absorption, and Hypoglycemic Activity of Escins Ia, Ib, IIa, IIb, and IIIa from the Seeds of *Aesculus hippocastanum* L.," *Chem. Pharm. Bull.* 44(8):1454-1464, Aug. 1996.
Zijlstra et al., "The Direct Agglutination Test for Diagnosis of Visceral Leishmaniasis Under Field Conditions in Sudan: Comparison of Aqueous and Freeze-Dried Antigens," *Trans. R. Soc. Trap. Med. Hyg* 91(6):671-673, Nov.-Dec. 1997.
Fiedler, U., (1953). "Aesculus Hippocastanum," Arzneimittel-Forschung, 4: 213-216. (With Google Translation), 16 pages total.

(56) References Cited

OTHER PUBLICATIONS

CN 201910261589.3—Second Office Action, dated Jan. 24, 2022, 16 pages (with English translation).
CN 201910261589.3—First Office Action, dated Jan. 28, 2021, 71 pages (with English translation).
CN 201910261589.3—Rejection Decision, dated May 27, 2022, 13 pages (with English translation).

* cited by examiner

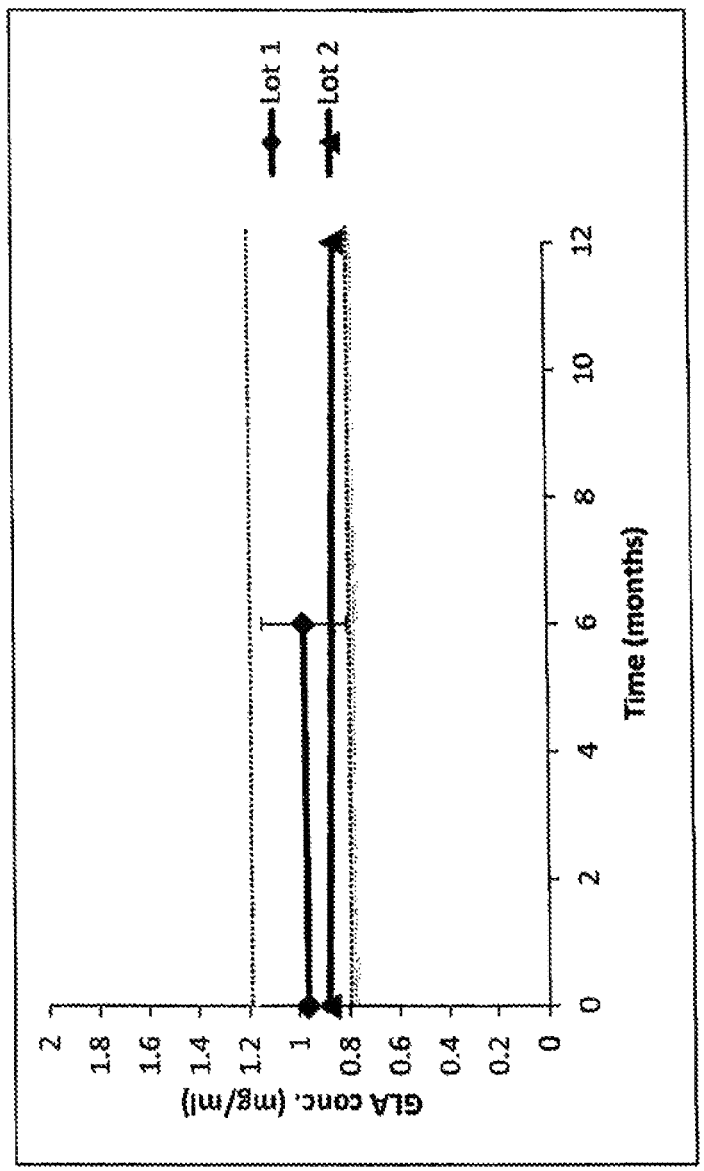
Figure 1. GLA-AF stability by HPLC

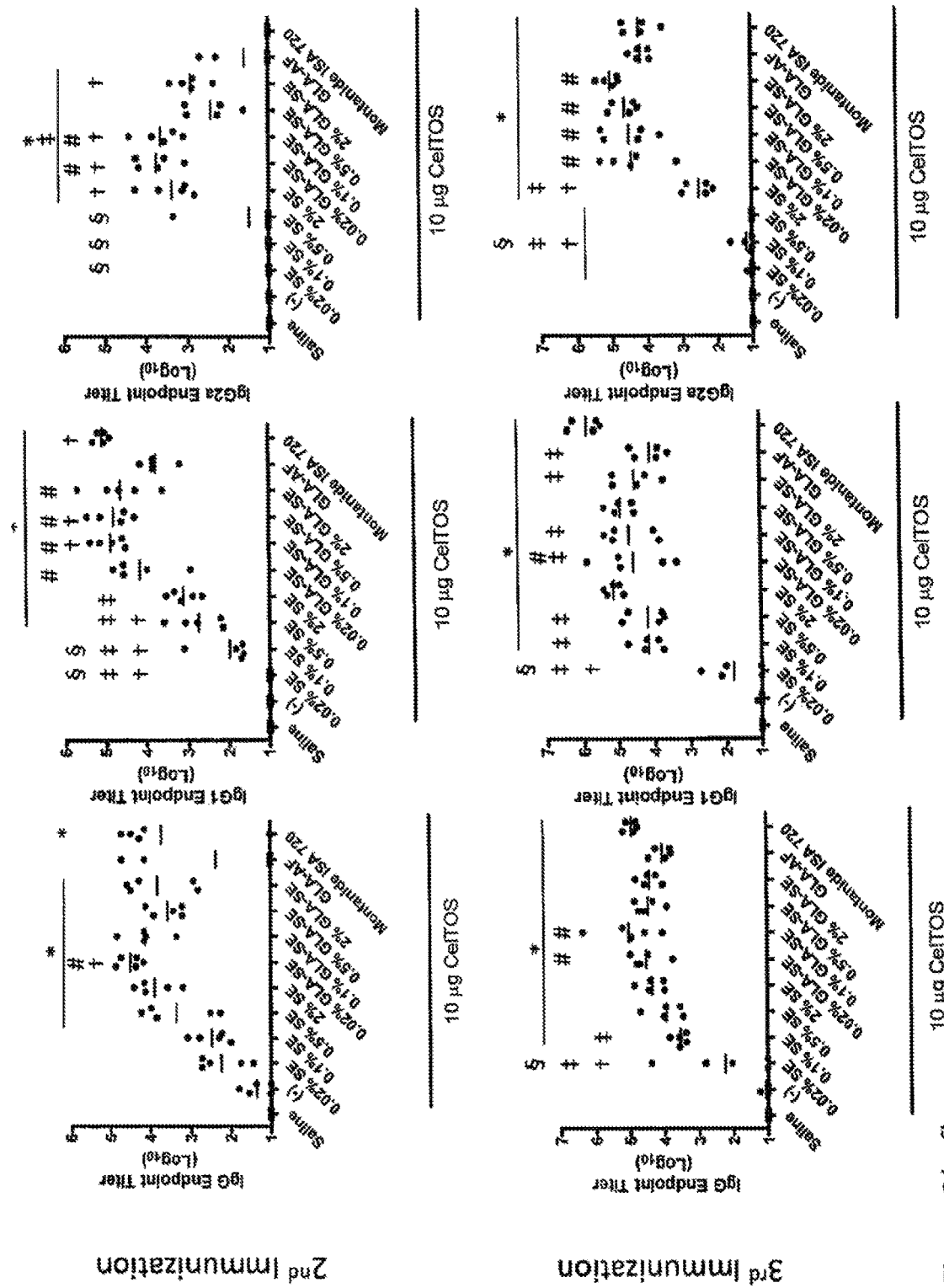
Figure 2(a-f)
*p<0.05 vs. Ag, #p<0.05 vs. Same % oil +/- GLA, §p<0.05 vs. 2% SE, †p<0.05 vs. GLA-AF, ‡p<0.05 vs. Montanide

*p<0.05 vs. Ag
p<0.05 vs. Same % oil +/- GLA
§p<0.05 vs. 2% SE
†p<0.05 vs. GLA-AF
‡p<0.05 vs. Montanide

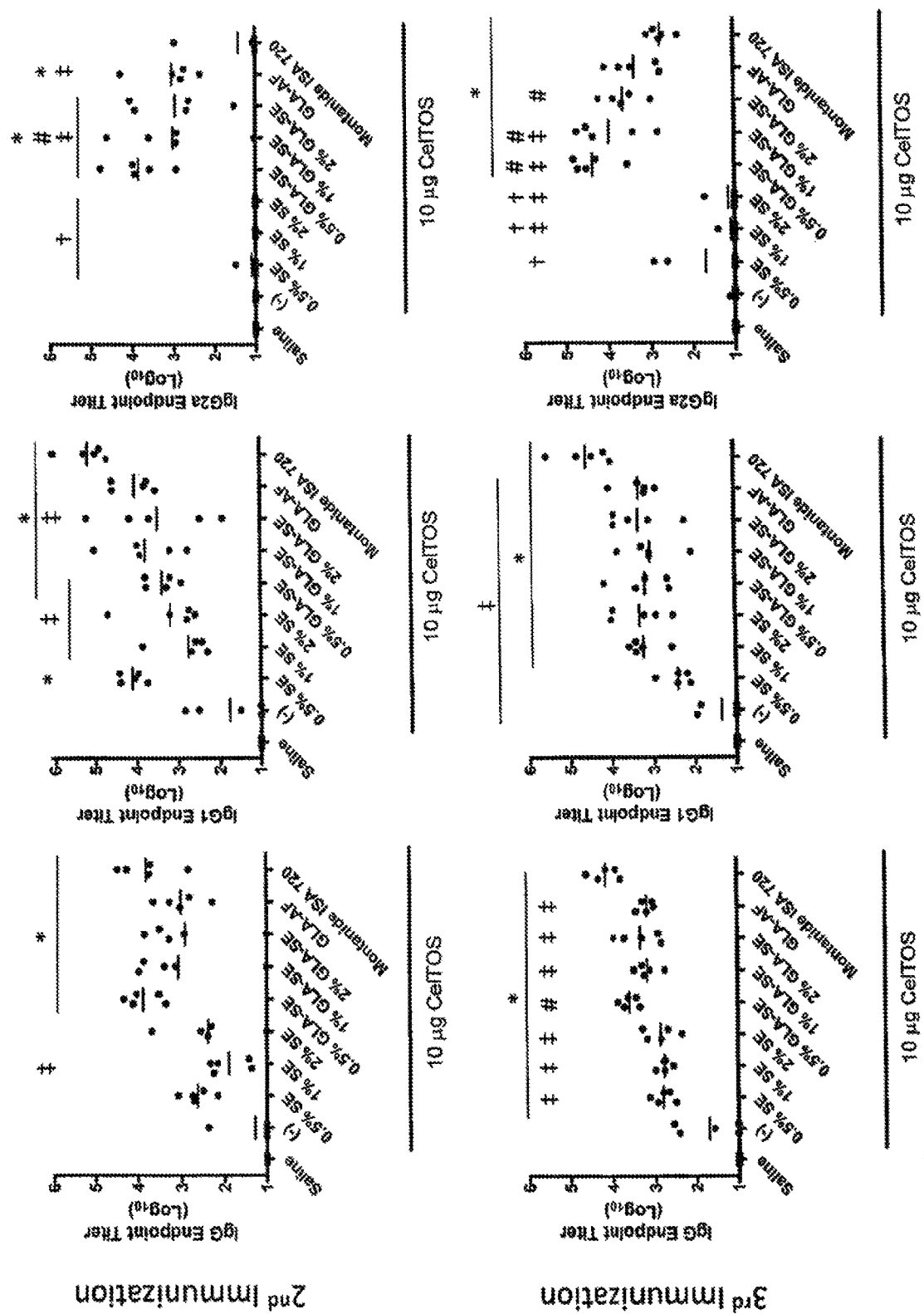
Figure 3(a-f)
*p<0.05 vs. Ag, #p<0.05 vs. Same % oil +/- GLA, §p<0.05 vs. 2% SE, †p<0.05 vs. GLA-AF, ‡p<0.05 vs. Montanide

* $p<0.05$ vs. Ag
$p<0.05$ vs. Same % oil +/- GLA
§ $p<0.05$ vs. 2% SE
† $p<0.05$ vs. GLA-AF
‡ $p<0.05$ vs. Montanide

*p<0.05 vs. Ag
p<0.05 vs. Same % oil +/- GLA
§p<0.05 vs. 2% SE
†p<0.05 vs. GLA-AF
‡p<0.05 vs. Montanide Stats key on next slide

*p<0.05 vs. Ag
p<0.05 vs. Same % oil +/- GLA
†p<0.05 vs. GLA-AF
‡p<0.05 vs. Montanide Table 1. Particle size and polydispersity of adjuvant formulations.

| Formulation | Lot # | Size (Z-avg, nm) | PdI |
|---|---|---|---|
| GLA-AF | 1 | 87.9 ± 1.6 | 0.248 ± 0.005 |
| GLA-AF | 2 | 91.8 ± 1.7 | 0.233 ± 0.009 |
| SE | 1 | 95.3 ± 1.9 | 0.039 ± 0.015 |
| SE | 2 | 97.7 ± 1.9 | 0.067 ± 0.013 |

Figure 6

ADJUVANT FORMULATIONS COMPRISING TLR4 AGONISTS AND METHODS OF USING THE SAME

This invention was made with Government support under Grant No. W911NF-10-1-0378 awarded by the Army Research Office. The Government has certain rights in the invention.

CROSS REFERENCE TO RELATED APPLICATIONS

This application is a National Phase application under 35 U.S.C. § 371 of International Application No. PCT/US2013/025204, filed Feb. 7, 2013, which claims the priority benefit of U.S. provisional application Ser. No. 61/596,066, filed Feb. 7, 2012, the contents of which are incorporated herein by reference in their entirety.

BACKGROUND OF THE INVENTION

1. Field of the Invention

The present invention relates to the field of pharmaceutical and vaccine formulations. More specifically, embodiments described herein relate to pharmaceutical and vaccine formulations, particularly oil-in-water emulsions, wherein the compositions comprise a TLR4 agonist, such as a glucopyranosyl lipid adjuvant (GLA).

2. Description of the Related Art

The immune system of higher organisms has been characterized as distinguishing foreign agents (or "non-self") agents from familiar or "self" components, such that foreign agents elicit immune responses while "self" components are ignored or tolerated. Immune responses have traditionally been characterized as either humoral responses, in which antibodies specific for antigens are produced by differentiated B lymphocytes known as plasma cells, or cell mediated responses, in which various types of T lymphocytes act to eliminate antigens by a number of mechanisms. For example, CD4+ helper T cells that are capable of recognizing specific antigens may respond by releasing soluble mediators such as cytokines to recruit additional cells of the immune system to participate in an immune response. Also, CD8+ cytotoxic T cells that are also capable of specific antigen recognition may respond by binding to and destroying or damaging an antigen-bearing cell or particle. It is known in the immunological arts to provide certain vaccines according to a variety of formulations, usually for the purpose of inducing a desired immune response in a host.

For example, certain emulsion systems for formulating adjuvant compositions have been described, including single or multiphase emulsion systems. Oil in water emulsion adjuvants per se have been suggested to be useful as adjuvant composition (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B).

Despite these known methods for producing emulsion systems for preparing adjuvant compositions, current emulsion adjuvant compositions still suffer from many drawbacks. Accordingly, there is a need for further, improved emulsion adjuvant compositions, such as oil-in-water emulsion formulations comprising TLR4 agonists. As described herein, the present invention meets these needs and offers other related advantages.

BRIEF SUMMARY OF THE INVENTION

According to one aspect, the present invention provides an oil-in-water emulsion comprising a TLR4 agonist and a metabolizable oil, wherein the metabolizable oil is present in the oil-in-water emulsion at a concentration of about 0.01%-1% v/v, or preferably about 0.01%-0.5% v/v, wherein the hydrophobic:lipophilic balance (HLB) of the oil-in-water emulsion is greater than about 9, or greater than about 10, or between about 9-12.

Also provided herein is an oil-in-water emulsion comprising a TLR4 agonist, a metabolizable oil, and a surfactant, wherein the metabolizable oil is present in the oil-in-water emulsion at a concentration of about 0.01%-1% v/v, or preferably about 0.01%-0.5% v/v. In some embodiments, the metabolizable oil concentration is below 1% v/v. In some embodiments, the hydrophobic:lipophilic balance (HLB) of the oil-in-water emulsion is greater than about 9, or greater than about 10, or between about 9-12.

The TLR4 agonist used in the oil-in-water emulsions of the invention can be selected from TLR4 agonists known and available in the art. In certain specific embodiments, the TLR4 agonist is selected from MPL, 3D-MPL or a synthetic GLA adjuvant.

In some embodiments, the synthetic GLA adjuvant has the following structure:

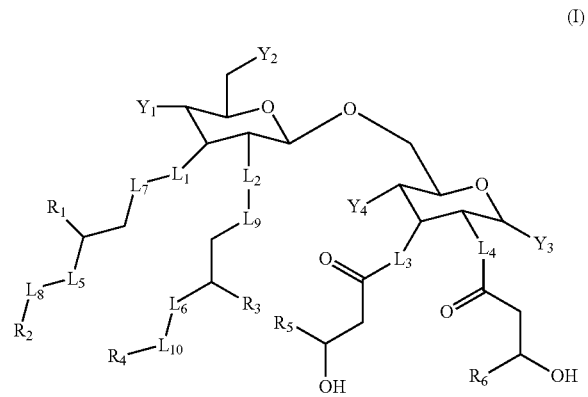

(I)

or a pharmaceutically acceptable salt thereof, wherein:

$L_1$, $L_2$, $L_3$, $L_4$, $L_5$ and $L_6$ are the same or different and independently —O—, —NH— or —(CH$_2$)—;

$L_7$, $L_8$, $L_9$, and $L_{10}$ are the same or different and independently absent or —C(=O)—;

$Y_1$ is an acid functional group;

$Y_2$ and $Y_3$ are the same or different and independently —OH, —SH, or an acid functional group;

$Y_4$ is —OH or —SH;

$R_1$, $R_3$, $R_5$ and $R_6$ are the same or different and independently $C_{8-13}$ alkyl; and $R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl.

For example, in a more specific embodiment, the oil-in-water emulsion comprises a synthetic GLA adjuvant having the following structure:

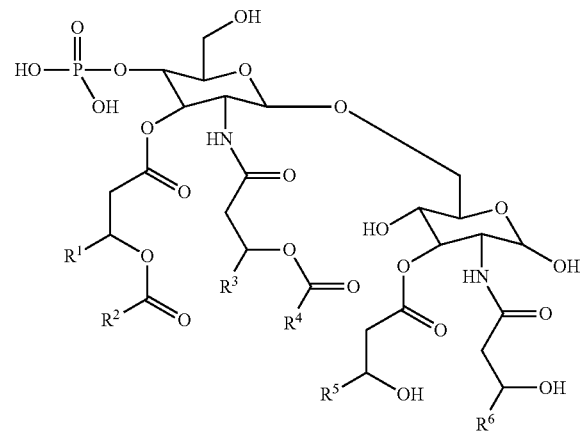

In certain embodiments of the above GLA structure, $R^1$, $R^3$, $R^5$ and $R^6$ are $C_{11}$-$C_{20}$ alkyl; and $R^2$ and $R^4$ are $C_{12}$-$C_{20}$ alkyl. In a more specific embodiment, $R^1$, $R^3$, $R^5$ and $R^6$ are $C_{11}$ alkyl; and $R^2$ and $R^4$ are $C_{13}$ alkyl. In another more specific embodiment, $R^1$, $R^3$, $R^5$ and $R^6$ are $C_{10}$ alkyl; and $R^2$ and $R^4$ are $C_8$ alkyl.

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the oil-in-water emulsion comprises a synthetic GLA adjuvant having the following structure:

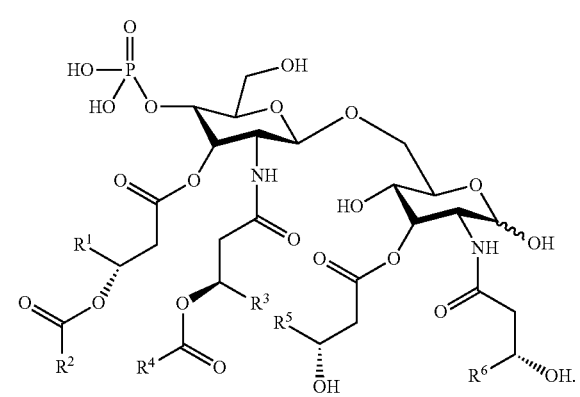

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the oil-in-water emulsion comprises a synthetic GLA adjuvant having the following structure:

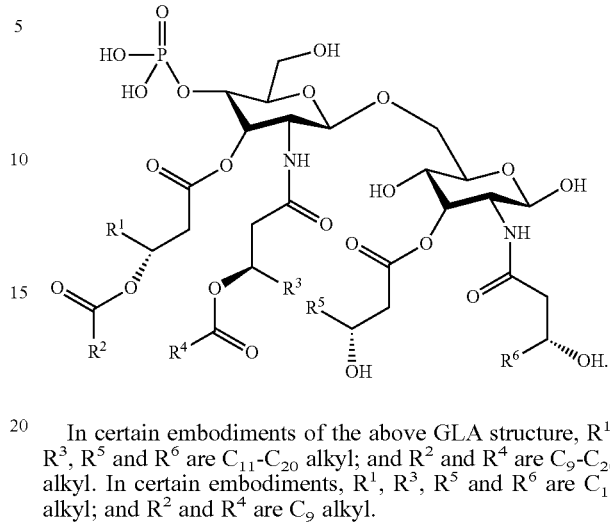

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the oil-in-water emulsion comprises a synthetic GLA adjuvant having the following structure:

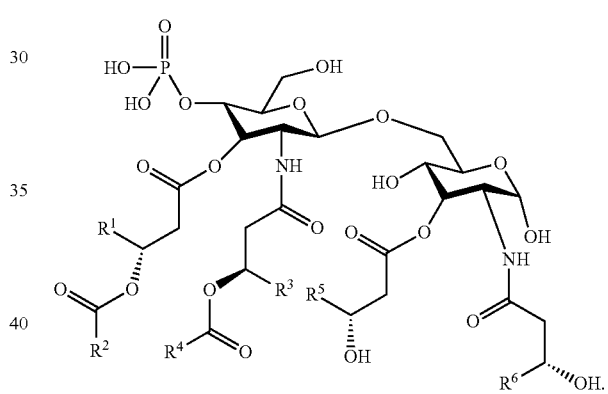

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the oil-in-water emulsion comprises a synthetic GLA adjuvant having the following structure:

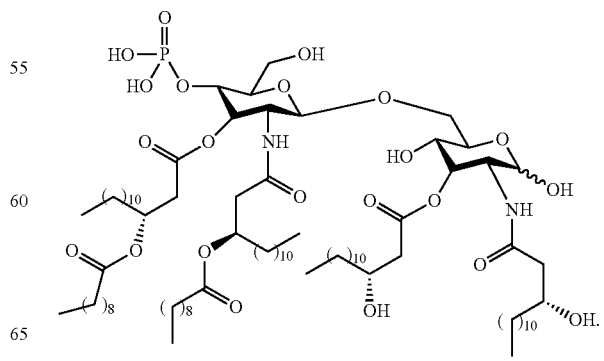

In certain embodiments, the oil-in-water emulsion comprises a synthetic GLA adjuvant having the following structure:

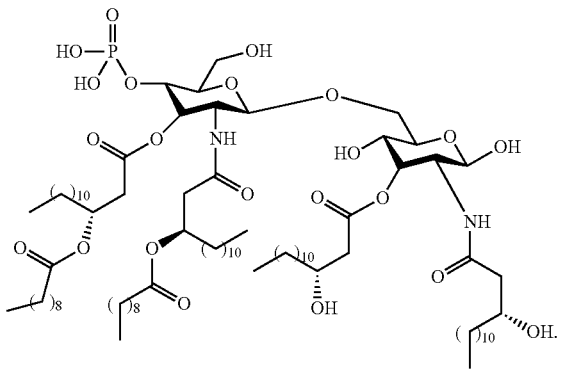

In certain embodiments, the oil-in-water emulsion comprises a synthetic GLA adjuvant having the following structure:

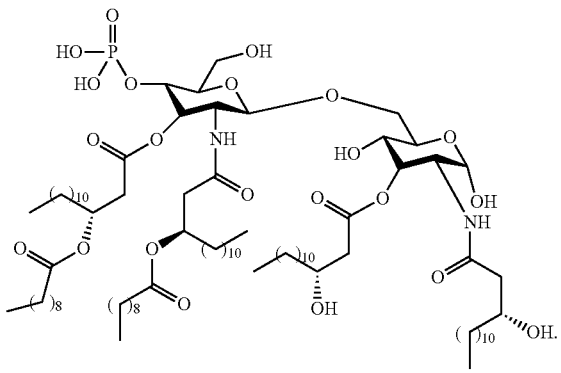

It will be understood that the emulsions of the invention can include other components necessary or desired for an intended effect. For example, the oil-in-water emulsions of the invention, in some embodiments, further comprise 1,2-dimyristoyl-sn-glycero-3-phosphocholine(DMPC). In some embodiments, the DMPC in the oil-in-water emulsions is synthetic. In some embodiments, the oil-in-water emulsion comprises 1-palmitoyl-2-oleoyl-sn-glycerol-3-phsphocholine (POPC). In some embodiments, the POPC in the oil-in-water emulsions is synthetic. In some embodiments, the oil-in-water emulsion comprises 1,2-dioleoyl-sn-glycero-3-phosphocholine (DOPC). In some embodiments, the DOPC in the oil-in-water emulsions is synthetic. In other embodiments, the emulsions further comprise a surfactant, such as pluronic F68. In still other embodiments, the emulsions further comprise an antioxidant, such as vitamin E.

The metabolizable oil used in the emulsions of the invention can be selected from any of a variety of available sources. In certain embodiments, the metabolizable oil comprises squalene. In other embodiments, the metabolizable oil comprises yeast-derived squalene. In still other embodiments, the metabolizable oil comprises a yeast-derived isoprenoid that is structurally distinct from squalene.

Of course, it will be understood that the emulsions can be used in the presence of one or more antigens in order to elicit antigen-specific immune responses. Alternatively, the emulsions can be used in the absence of antigen in order to elicit a non-specific immune response.

In another aspect, the invention provides an oil-in-water emulsion comprising a TLR4 agonist (such as a synthetic GLA adjuvant), a metabolizable oil, and DMPC or DOPC. In some embodiments, the metabolizable oil concentration in the oil-in-water emulsion is about 0.01%-20% (e.g., about 10%, about 5%, about 2%, about 1%, about 0.5%, about 0.2%). In some embodiments, DMPC or DOPC concentration in the oil-in-water emulsion is about 0.002%-2%. In some embodiments, the HLB of the emulsion is greater than about 9 or about 10. In some embodiments, the DMPC or DOPC concentration is from about 0.015% to 0.25%. In some embodiments, the DMPC is DOPC in the emulsion is synthetic.

In one specific embodiment of the invention, there is provided an oil-in-water emulsion comprising a synthetic GLA adjuvant, a metabolizable oil at a concentration of about 0.01%-1% v/v, and DMPC at a concentration of about 0.002%-2% DMPC, wherein the HLB of the emulsion is greater than about 10. In some embodiments, the DMPC concentration is from about 0.015% to 0.25%.

Also provided by the present invention are methods for stimulating an immune response in a subject comprising administering an oil-in-water emulsion as described herein to the subject and thereby stimulating an immune response in the subject. Of course the methods may be used to elicit non-specific immune responses, wherein the emulsions do not contain antigen. More typically, the emulsions will contain one or more antigens, such that the immune response is an antigen-specific immune response.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE SEVERAL VIEWS OF THE DRAWING(S)

FIG. 1. GLA concentration over time in GLA-AF batches as measured by HPLC-CAD. The dotted lines represent the upper and lower specification limits for the HPLC method.

FIG. 2. Antibody responses to PfCelTOS vaccines containing various adjuvant formulations with emulsion doses from 0.02% to 2% v/v oil as measured after the $2^{nd}$ and $3^{rd}$ immunizations. Top panel from left to right: (a-c) IgG, IgG1 and IgG2a antibody endpoint titers measured 3 weeks after the $2^{nd}$ immunization. Bottom panel from left to right: (d-f) IgG, IgG1 and IgG2a antibody endpoint titers measured 3 weeks after the $3^{rd}$ immunization. (g) Long-lived antibody-secreting cells in the bone marrow detected 3 weeks after the $3^{rd}$ immunization.

FIG. 3. Antibody responses to PfCelTOS vaccines containing various adjuvant formulations with emulsion doses from 0.5% to 2% v/v oil as measured after the $2^{nd}$ and $3^{rd}$ immunizations. Top panel from left to right: (a-c) IgG, IgG1 and IgG2a antibody endpoint titers measured 3 weeks after the $2^{nd}$ immunization. Bottom panel from left to right: (d-f) IgG, IgG1 and IgG2a antibody endpoint titers measured 3 weeks after the $3^{rd}$ immunization. (g) Long-lived antibody-secreting cells in the bone marrow detected 3 weeks after the $3^{rd}$ immunization.

Figure 4:
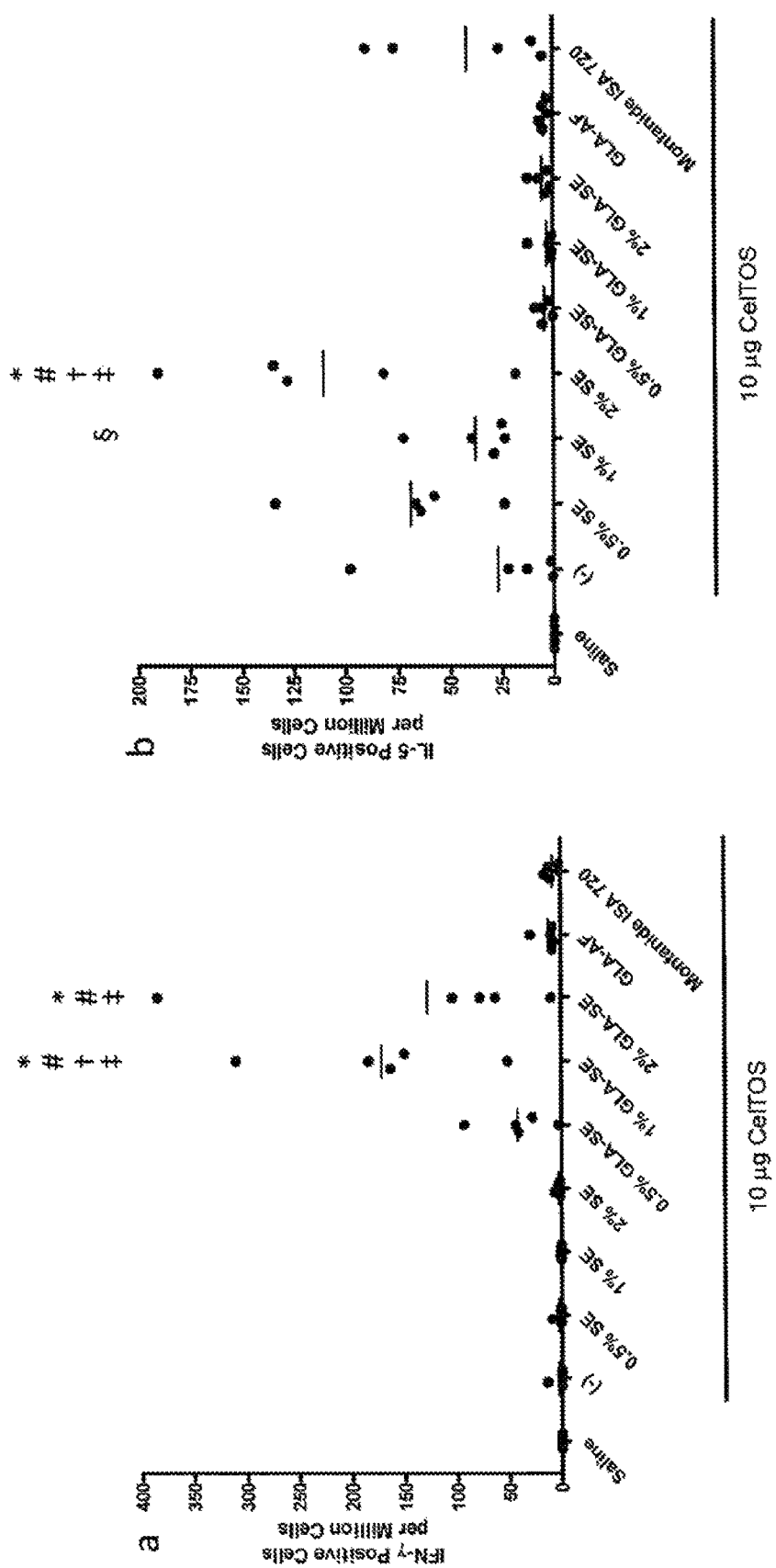

FIG. 4. Antigen-specific cytokine-producing cells detected by ELISPOT assay 3 weeks after the $3^{rd}$ immunization. (a) IFN-γ producing cells. (b) IL-5 producing cells.

Figure 5:
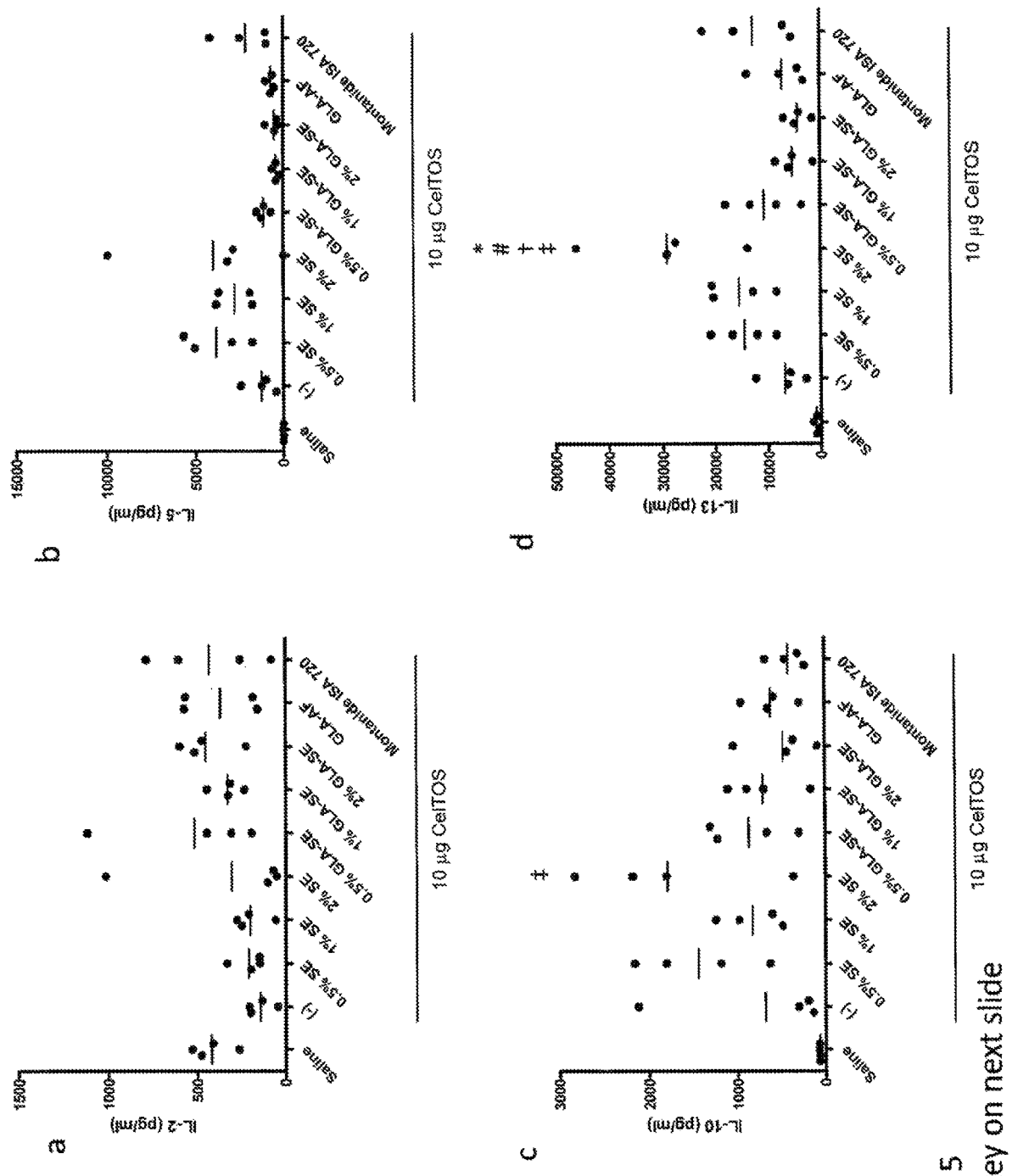
Figure 5:
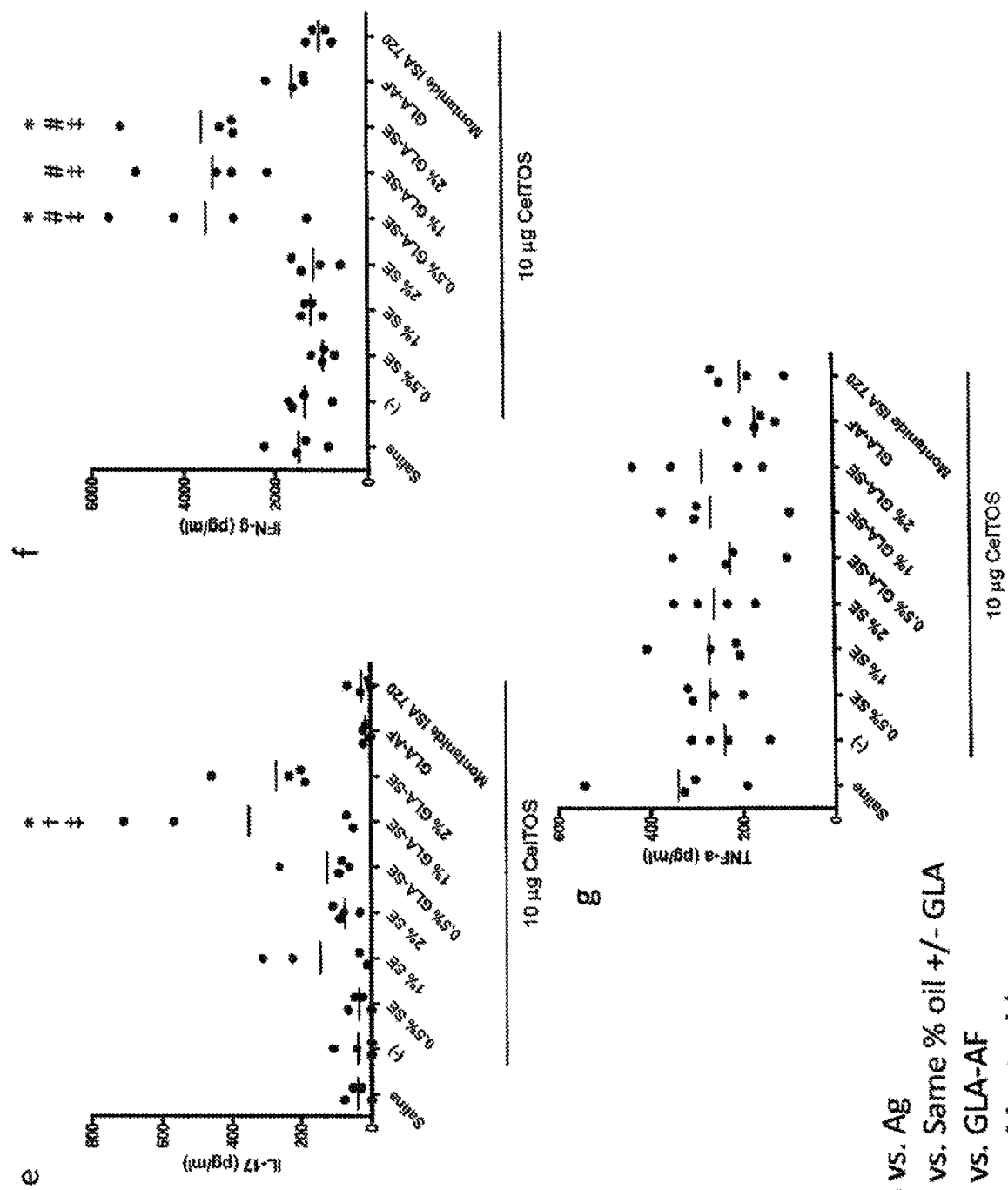

FIG. 5. Antigen-specific cytokine production detected 3 weeks after the 3$^{rd}$ immunization by multiplex bead assay (Luminex®). (a) IL-2 (b) IL-5 (c) IL-10 (d) IL-13 (e) IL-17 (f) IFN-γ (g) TNF-α.

FIG. 6. Particle size and polydispersity of adjuvant formulations.

Figure 7:
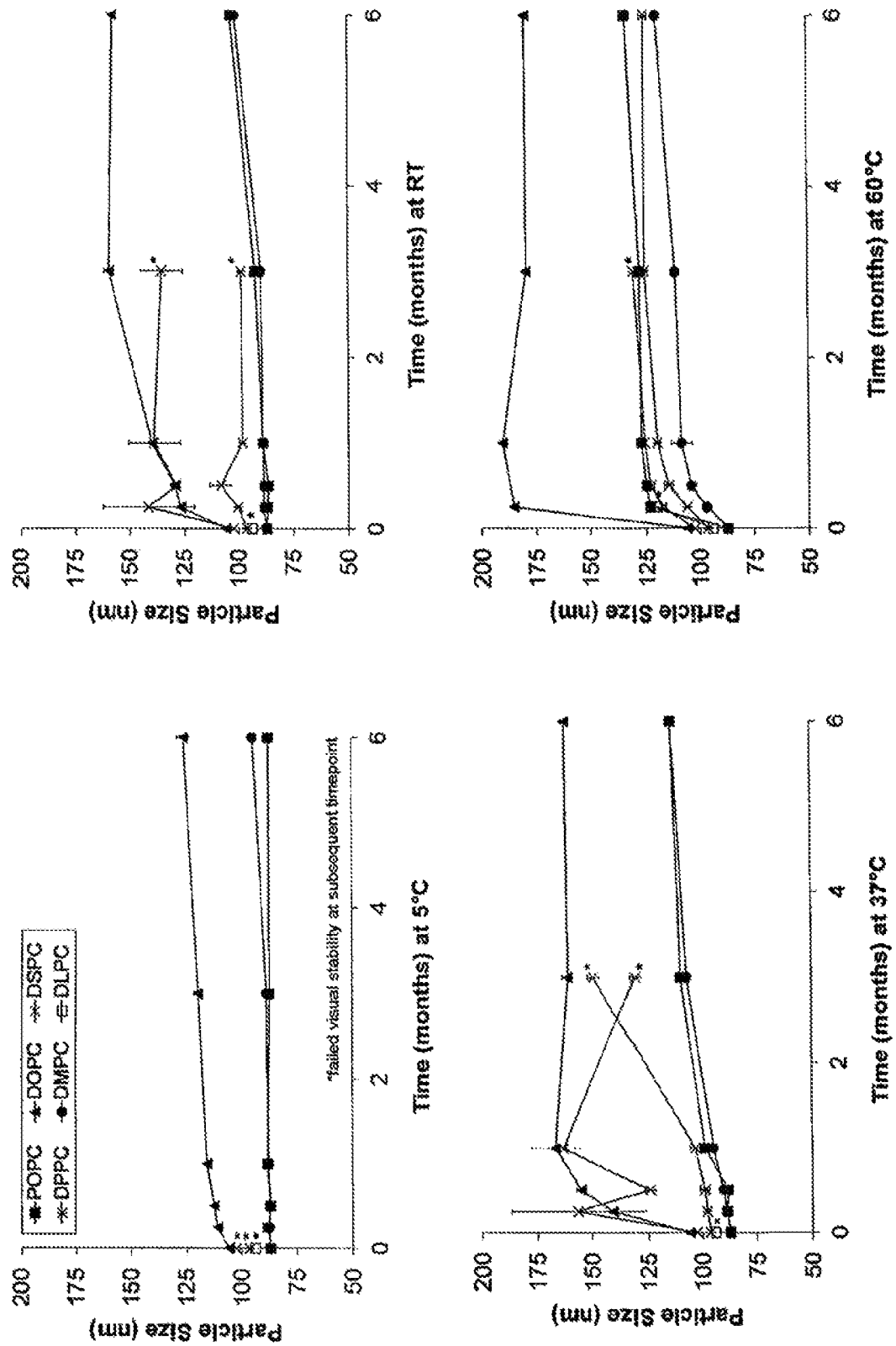

FIG. 7. Emulsion particle size stability at various storage temperatures. Shown are results following storage at (a) 5° C. (top left graph), (b) RT (top right graph), (c) 37° C. (bottom left graph) and (d) 60° C. (bottom right graph). Particle size was measured using Malvern Instruments APS, with error bars representing standard size deviation of three separate aliquots from one batch of each emulsion.

Figure 8:
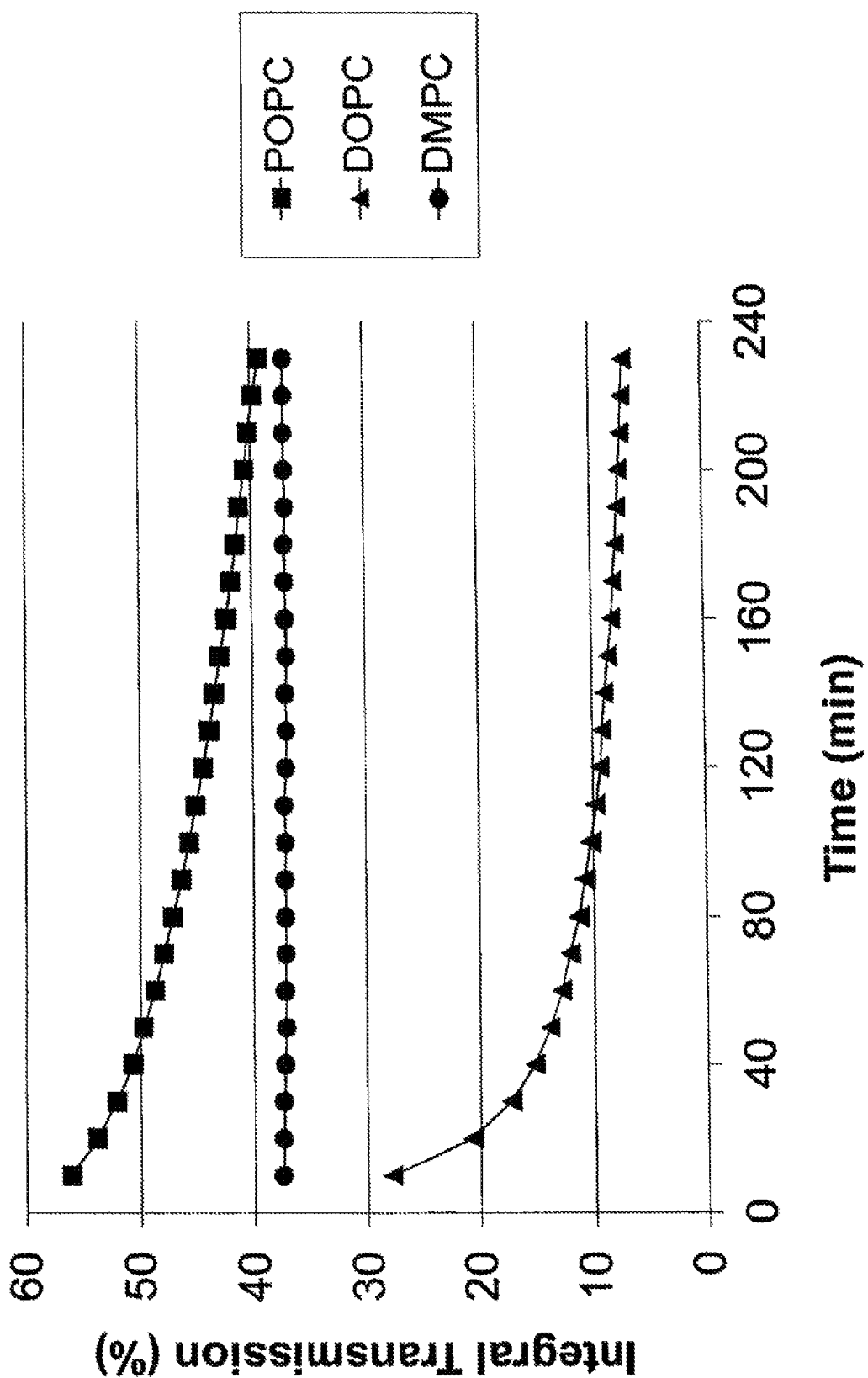

FIG. 8. Laser scattering optical profiling analysis of emulsion stability. Integral transmission profiles of the 25-30 mm region of cuvettes containing emulsion, measured over 4 hours at 60° C.

Figure 9A:
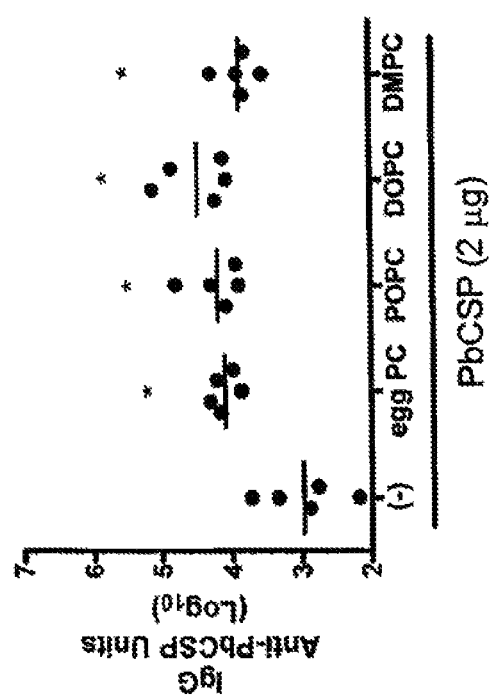
Figure 9B:
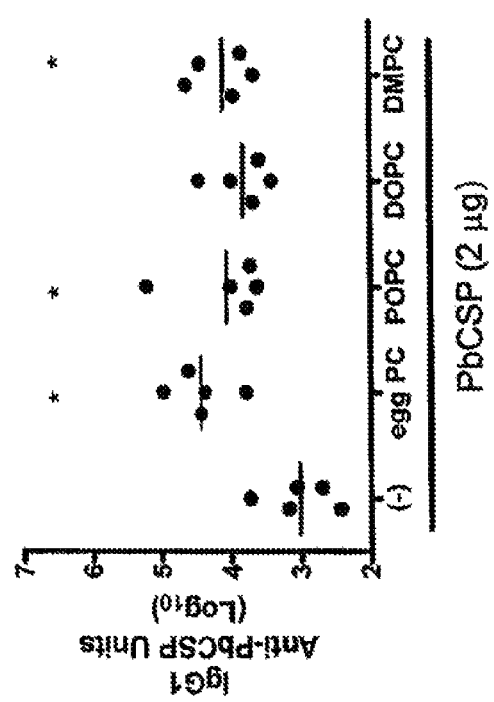
Figure 9C:
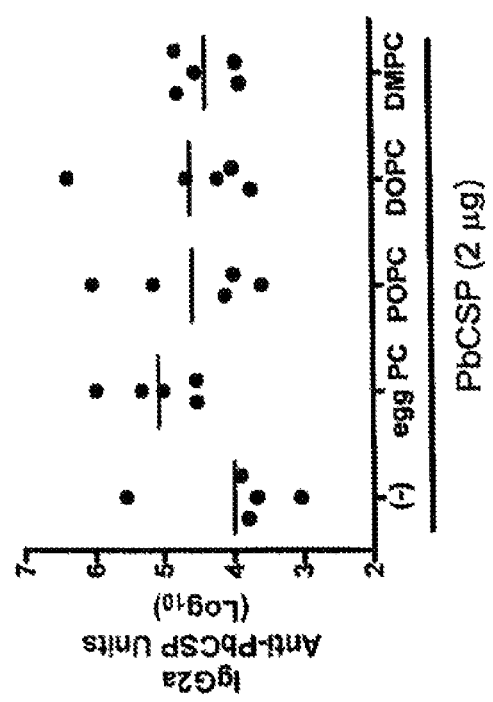
Figure 10A:
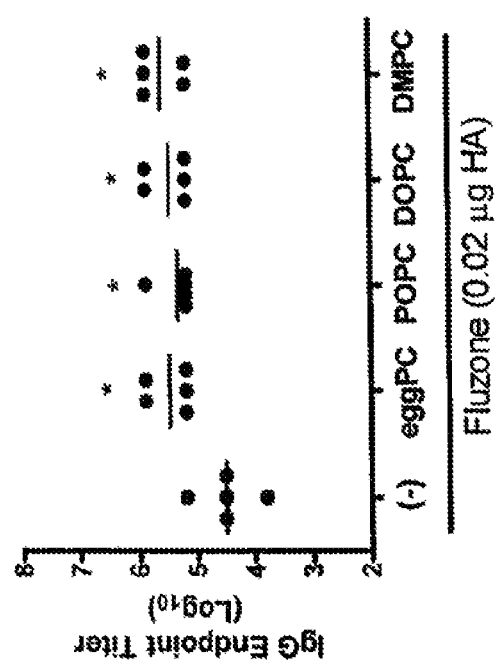
Figure 10B:
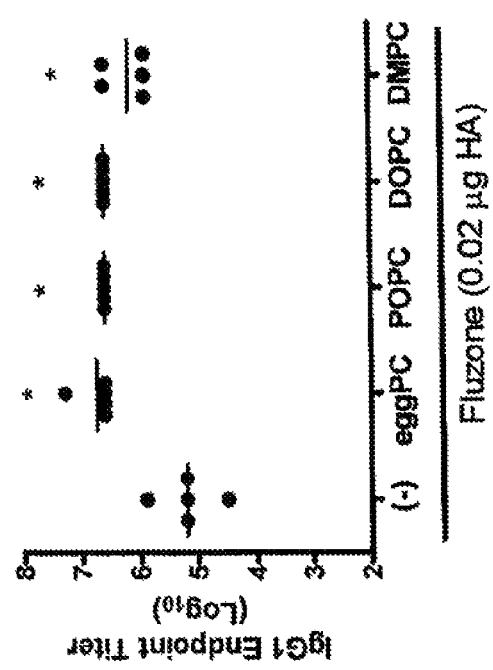
Figure 10C:
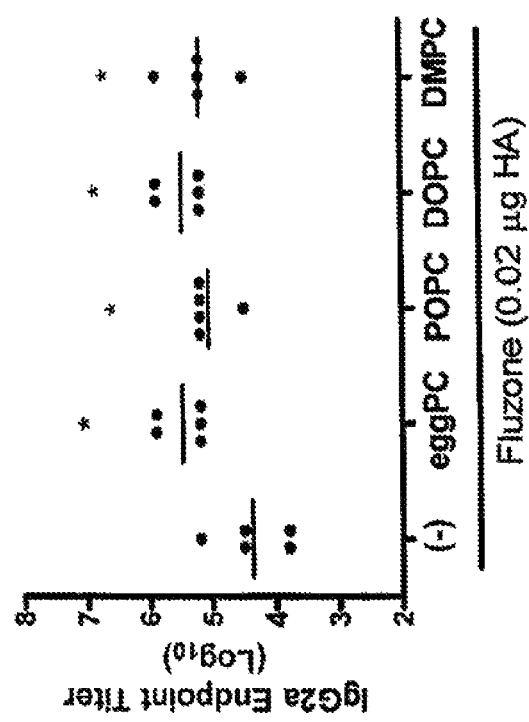
Figure 10D:
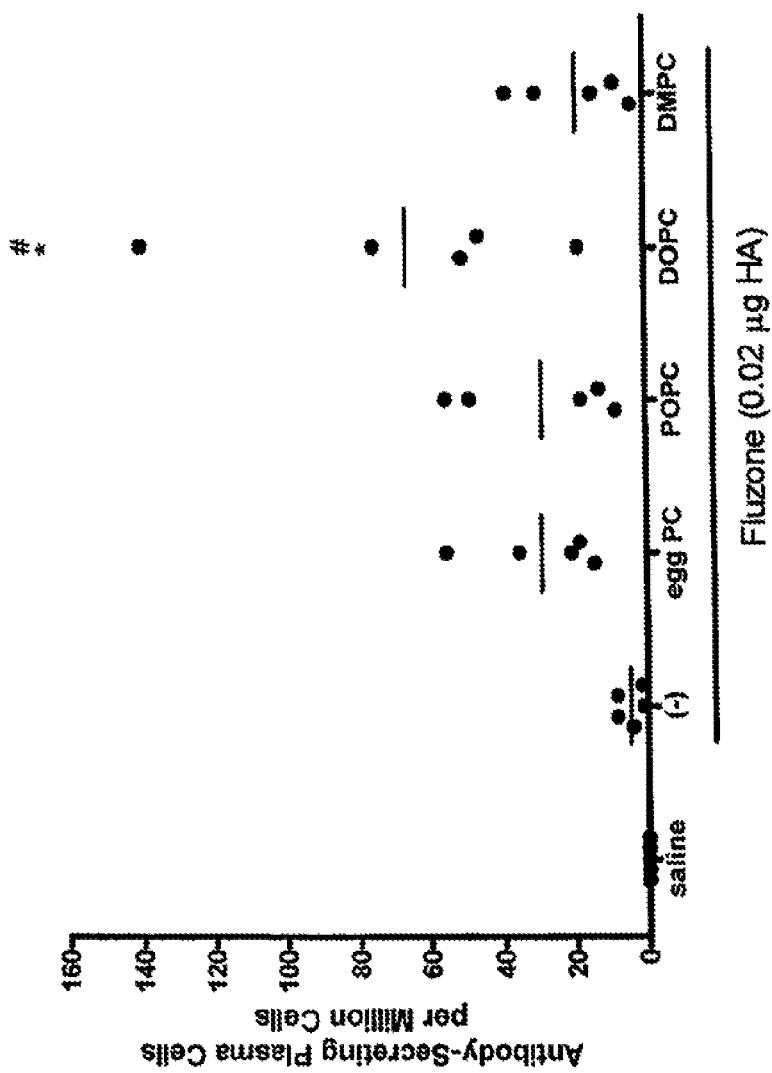

FIG. 9. Effect of emulsions on antibody responses induced by immunization with recombinant malaria antigen. BALB/c mice were immunized twice with PbCSP antigen formulated with emulsions containing egg PC or synthetic PC, including POPC, DOPC, and DMPC. Antigen-specific IgG (a), IgG1 (b) and IgG2a (c) were determined by ELISA. n=5 per group, and data are shown as values from individual mice (Log$_{10}$) with the bar representing the mean. *=p-value<0.05 versus immunization with protein alone.

FIG. 10. Effect of adjuvant formulation in humoral immune responses induced by immunization with inactivated split-virus influenza vaccine (Fluzone). BALB/c mice were immunized with Fluzone formulated with emulsions containing egg PC or synthetic PC, including POPC, DOPC, and DMPC. Antigen-specific IgG (a), IgG1 (b) and IgG2a (c) were determined by ELISA. IgG-secreting bone marrow plasma cells against Fluzone were determined by ELISPOT (d). Results for (a-c) are shown as the endpoint titer (Log$_{10}$), with each dot representing individual mice and the bar representing the mean. Results for (d) also represent individual mice in each group, with the bar representing the mean ASPC/group. *=p-value<0.05 versus immunization with vaccine alone and #=p-value<0.05 versus immunization with the vaccine containing the DMPC emulsion.

Figure 11A:
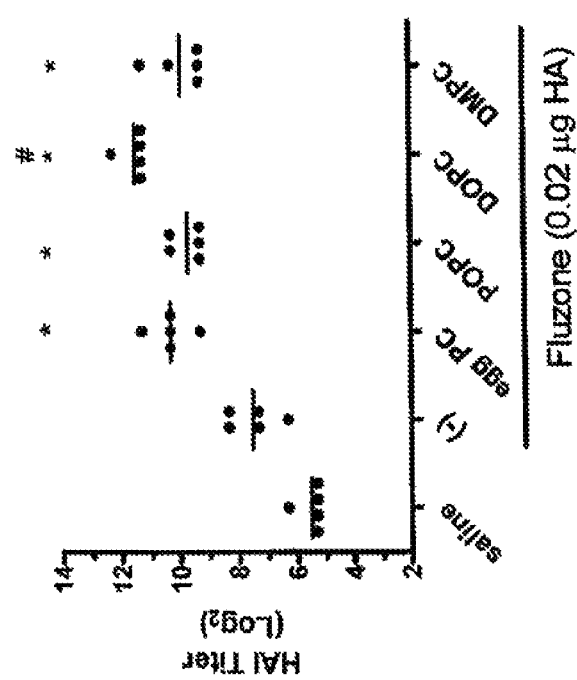
Figure 11B:
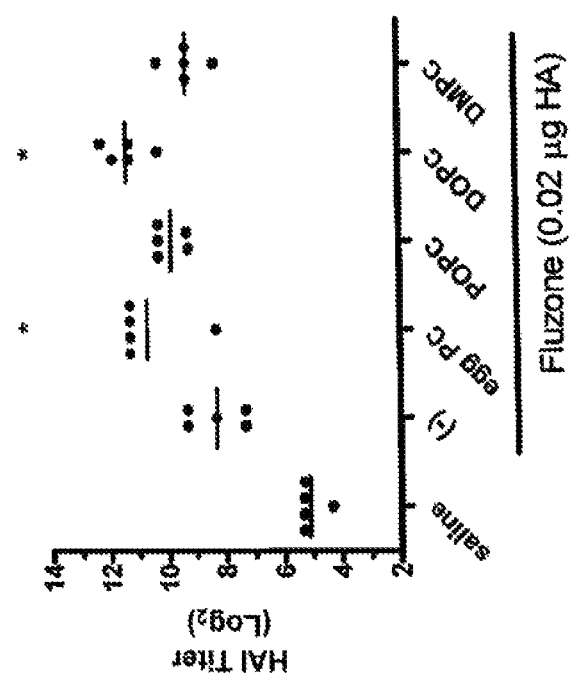

FIG. 11. HI titers were enhanced by immunization with Fluzone formulated with egg PC or synthetic PCs. BALB/c mice were immunized with Fluzone and various emulsions, then serum HI titers determined four weeks after boosting. (a) HI titers against the A/Solomon Islands/3/2006 (H1N1) component of Fluzone. (b) HI titers against the A/Wisconsin/67/2005 (H3N2) component of Fluzone. Data are shown as the (Log$_2$) titer for each individual animal, with the bar representing the mean. *=p-value<0.05 versus immunization with vaccine alone and #=p-value<0.05 versus immunization with the vaccine containing POPC emulsion or DMPC emulsion.

Figure 12A:
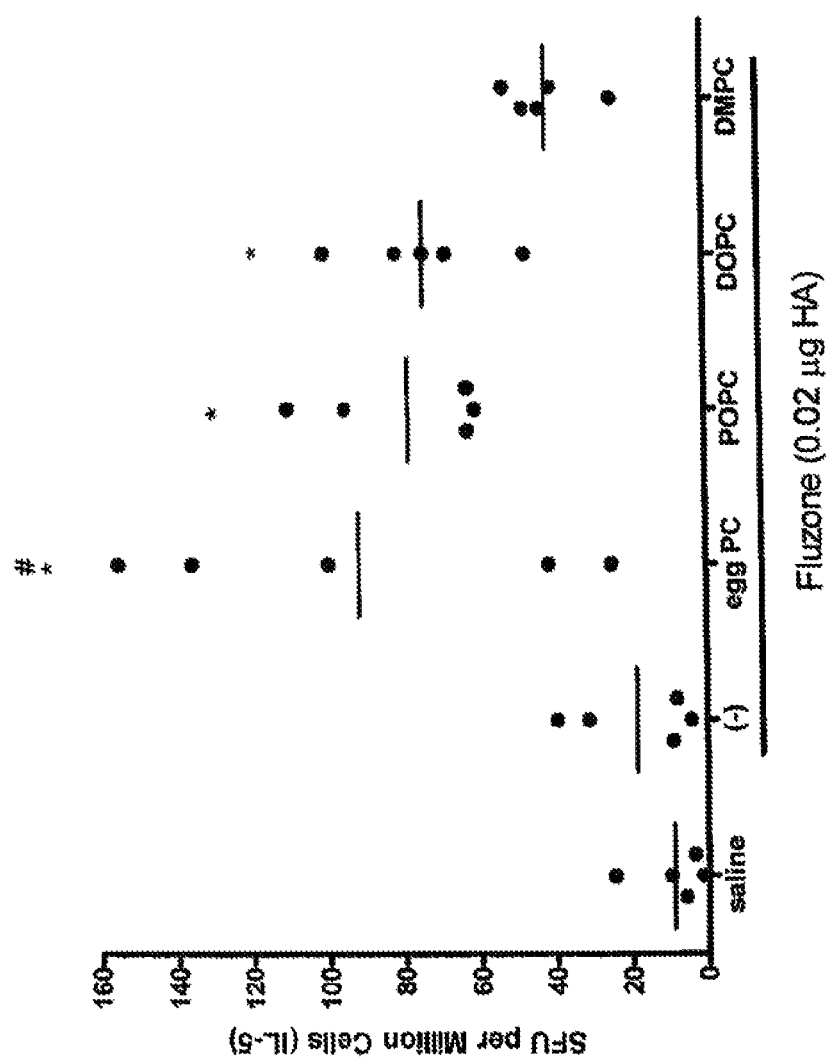
Figure 12B:
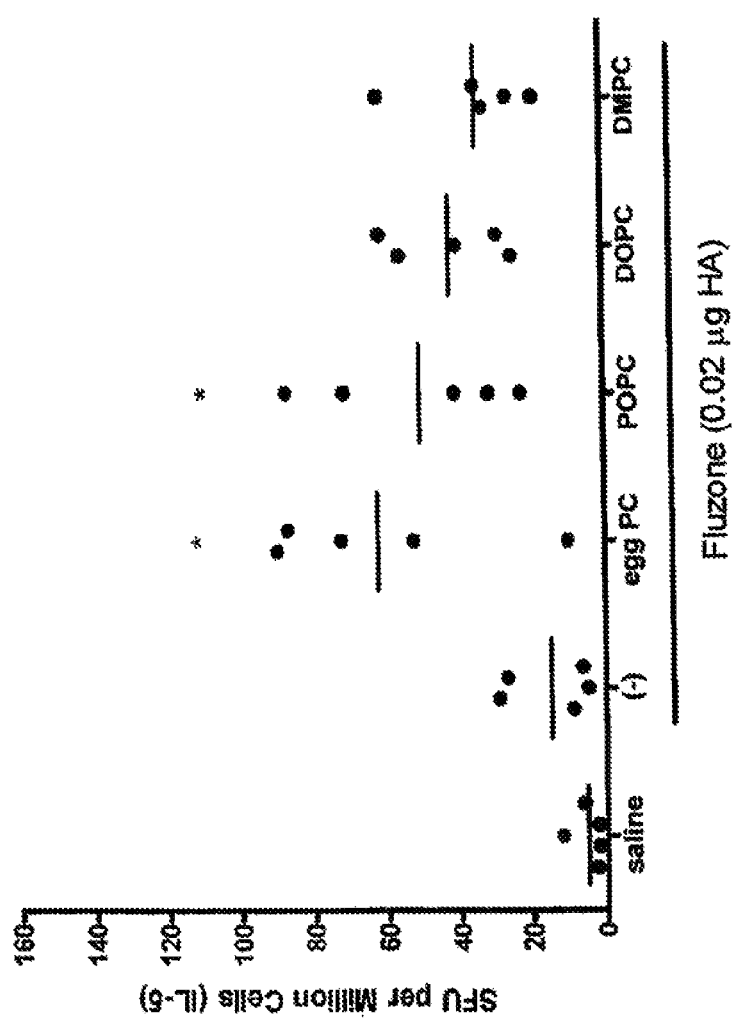

FIG. 12. IL-5 producing cells are increased after immunization with Fluzone formulated with emulsions. Splenocytes from BALB/c mice immunized with Fluzone and various emulsions were stimulated with either (a) 5 HAU of inactivated A/Solomon Islands/3/2006 (H1N1) or (b) 2 HAU inactivated A/Wisconsin/67/2005(H3N2) and IL-5 producing cells determined by ELISPOT. Data is represented as the number of spot forming units (SFU) per million splenocytes for individual mice/group, with the bar representing the mean, n=5 per group. *=p-value<0.05 versus immunization with vaccine alone and #=p-value<0.05 versus immunization with the vaccine containing the DMPC emulsion.

DETAILED DESCRIPTION OF THE INVENTION

The present invention in its many aspects provides emulsion compositions comprising TLR4 agonists, particularly oil-in-water emulsions comprising TLR4 agonists, and related methods of using the same as adjuvant and immunostimulatory compositions.

As discussed herein, the formulations of the invention generally comprise an oil-in-water emulsion comprising a TLR4 agonist and a metabolizable oil, wherein the metabolizable oil is present in the oil-in-water emulsion at a concentration of about 0.01%-1% v/v, or about 0.01%-0.5% v/v, and wherein the hydrophobic:lipophilic balance (HLB) of the oil-in-water emulsion is greater than about 9, or greater than about 10, or between about 9-12.

Methods for determining the HLB of an emulsion are known in the art. See, e.g., world wide web at firp.ula.ve/archivos/historicos/76_Book_HLB_ICI.pdf and at chemist-scorner.com/hlb-the-easiest-way-to-create-an-emulsion/.

The oil emulsion adjuvants for use in the present invention may be natural or synthetic, and may be mineral or organic. Examples of mineral and organic oils will be readily apparent to the man skilled in the art.

In a particular embodiment, a composition of the invention comprises an emulsion of oil in water wherein the TLR4 agonist is incorporated in the oil phase. In order for an oil in water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any plant oil, vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used.

In certain illustrative embodiments, the formulations of the present invention comprise a metabolizable oil that is present at a concentration of about 0.01%-1% v/v, about 0.01%-0.5% v/v, at about 0.5% v/v, or about 0.2% v/v. In some embodiments, the metabolizable oil is present at a concentration below 1% v/v. Illustrative metabolizable oils useful according to the subject invention include, but are not limited to, squalene, soybean oil, sesame oil and caprylic/capric acid triglycerides (MIGLYCOL 810 oil). In one preferred embodiment, the metabolizable oil comprises squalene. In a more specific embodiment, the metabolizable oil comprises one or more yeast-derived isoprenoids, such as yeast-derived squalene or related isoprenoid structure derived from yeast.

Squalene (2,6,10,15,19,23-Hexamethyl-2,6,10,14,18,22-tetracosahexaene), for example, is an unsaturated oil which is found in large quantities in shark-liver oil, and in lower quantities in olive oil, wheat germ nil, rice bran oil, and yeast, and is a particularly preferred oil for use in this invention. Squalene is a metabolizable oil virtue of the fact that it is an intermediate in the biosynthesis of cholesterol (Merck index, 10th Edition, entry no. 8619).

In other illustrative embodiments, certain formulations of the invention comprise an antioxidant. Illustrative antioxidants useful in the emulsion of the subject invention include, but are not limited to, a tocopherol, and ascorbic acid, with a tocopherol being preferred.

In still other illustrative embodiments, certain emulsions of the invention comprise a surfactant. Surfactants useful according to the subject invention are Pluronic F68, Tween 80, polysorbate 80 (CAPMUL POE-O low PV surfactant, ABITEC Corp., Janesville, Wis.), polyethylene 660 12-hydroxystearate (SOLUTOL HS15, BASF Corp., Chicago, Ill.) and poloxamer 188 (PLURONIC Q F68 block co-polymer, BASF Corp., Chicago, Ill.), sodium cholate, glycerodeoxycholate, phosphatidyl choline, with poloxamer 188 being preferred. Other suitable surfactants include sphingolipids such as sphingomyelin and sphingosine and phospholipids such as egg phosphatidylcholine, 1,2-Dimyristoyl-sn-glycero-3-phosphoethanolamine, L-α-Phosphatidylethanolamine, and 1,2-Dipalmitoyl-sn-glycero-3-phosphocholine (DPPC) or mixtures thereof. DPPC is acceptable for use in humans. In some embodiments, the surfactant is DMPC, DOPC, and/or POPC (including synthetic DMPC, DOPC and POPC). One or more surfactants may be used.

In addition, in still other illustrative embodiments, certain formulations of the invention have a hydropobic:lipophilic balance (HLB) of greater than about 9 or greater than about 10 or greater than about 11. In other related embodiments, the formulations have an HLB between about 9-12, or between about 10-12, or between about 10-11.

In certain other illustrative embodiments, the formulations of the invention comprise the phospholipid 1,2-dimyristoyl-sn-glycero-3-phosphocholine (DMPC), particularly synthetic DMPC. Further, in some embodiments wherein the emulsion comprises DMPC, the emulsion does not comprise an antioxidant. Further still, in some embodiments wherein the emulsion comprises DMPC, the formulations have an HLB of greater than about 9, or greater than about 10, or greater than about 11, or have an HLB between about 9-12, about 10-12, or about 10-11. Where the formulations comprise DMPC, the formulations generally do not comprise egg phosphatidyl choline (PC).

Agents that can be added to the emulsion of the subject invention to make the adjuvant isotonic include dextrose, glycerol, mannitol, sorbitol, PEG 300, PEG 400 and polyethylene glycol.

Illustrative oil emulsions are oil in water emulsions, and in particular squalene in water emulsions. In addition, the most preferred oil emulsion adjuvants of the present invention comprise an antioxidant, which is preferably the oil .alpha.-tocopherol (vitamin E, EP 0 382 271 B1). WO 95/17210 and WO 99/11241 disclose emulsion adjuvants based on squalene, alpha-tocopherol, and TWEEN® 80, optionally formulated with the immuno stimulants QS21 and/or 3D-MPL (which are discussed above). WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges The method of producing oil in water emulsions is well known to the person skilled in the art. Commonly, the method comprises the mixing the oil phase with a suitable surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar)) could be adapted to produce smaller or larger volumes of emulsion. This adaptation could be achieved by routine experimentation comprising the measurement of the resultant emulsion until a preparation was achieved with oil droplets of the required diameter.

TLR4 Agonists

In certain preferred embodiments, a TLR4 agonist used in the formulations of the invention comprises a glucopyranosyl lipid adjuvant (GLA), such as those described in U.S. Patent Publication Nos. US2007/021017, US2009/045033, US2010/037466, and US 2010/0310602, the contents of which are incorporated herein by reference in their entireties.

For example, in certain embodiments, the TLR4 agonist is a synthetic GLA adjuvant having the following structure:

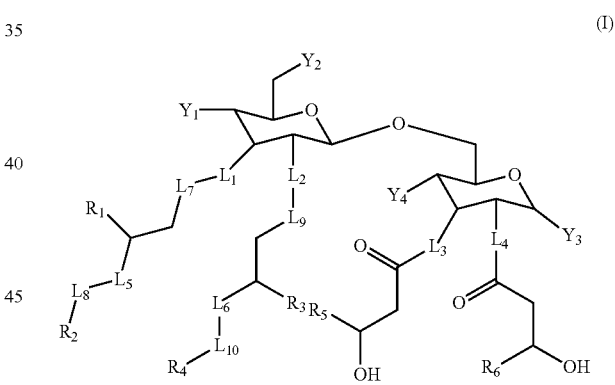

(I)

or a pharmaceutically acceptable salt thereof, wherein:

$L_1$, $L_2$, $L_3$, $L_4$, $L_5$ and $L_6$ are the same or different and independently —O—, —NH— or —($CH_2$)—;

$L_7$, $L_8$, $L_9$, and $L_{10}$ are the same or different and independently absent or —C(=O)—;

$Y_1$ is an acid functional group;

$Y_2$ and $Y_3$ are the same or different and independently —OH, —SH, or an acid functional group;

$Y_4$ is —OH or —SH;

$R_1$, $R_3$, $R_5$ and $R_6$ are the same or different and independently $C_{8-13}$ alkyl; and $R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl.

For example, in certain embodiments, the TLR4 agonist is a synthetic GLA adjuvant having the following structure:

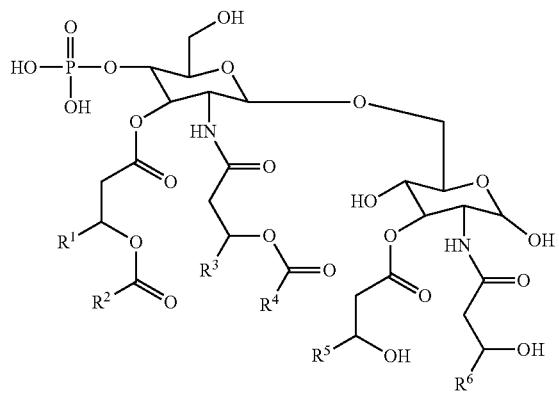

In a specific embodiment, $R^1$, $R^3$, $R^5$ and $R^6$ are $C_{11}$-$C_{20}$ alkyl; and $R^2$ and $R^4$ are $C_{12}$-$C_{20}$ alkyl.

In another specific embodiment, the GLA has the formula set forth above wherein $R^1$, $R^3$, $R^5$ and $R^6$ are $C_{11}$ alkyl; and $R^2$ and $R^4$ are $C_{13}$ alkyl.

In another specific embodiment, the GLA has the formula set forth above wherein $R^1$, $R^3$, $R^5$ and $R^6$ are $C_{10}$ alkyl; and $R^2$ and $R^4$ are $C_8$ alkyl.

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

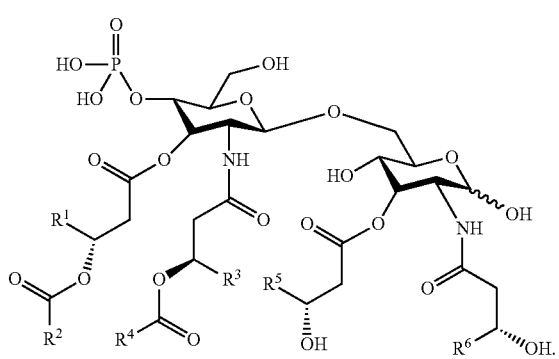

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

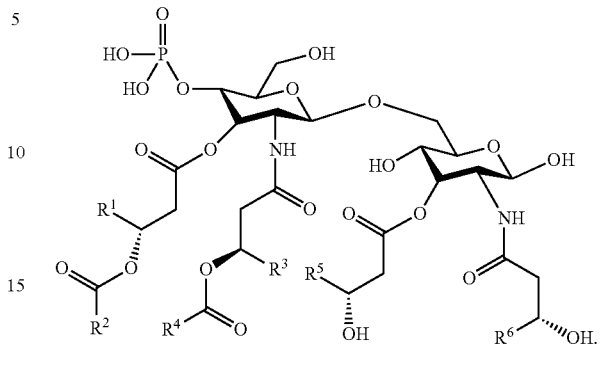

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

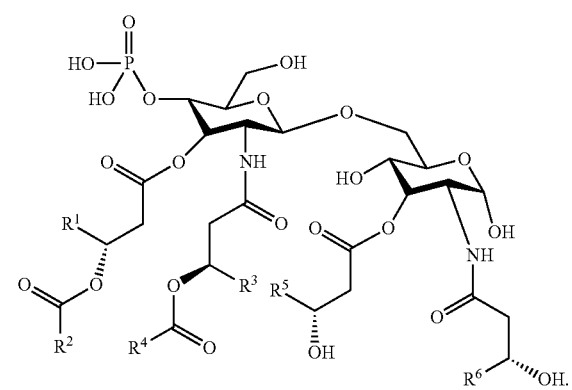

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

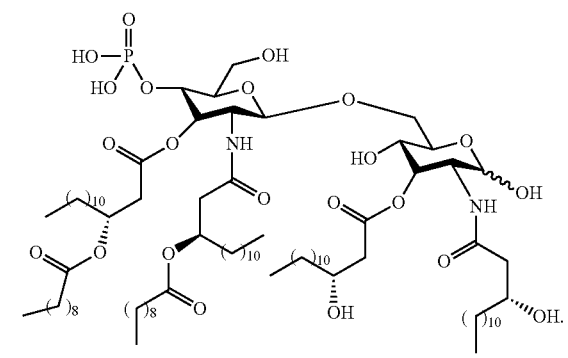

In certain embodiments, the TLR4 agonist is a synthetic GLA adjuvant having the following structure:

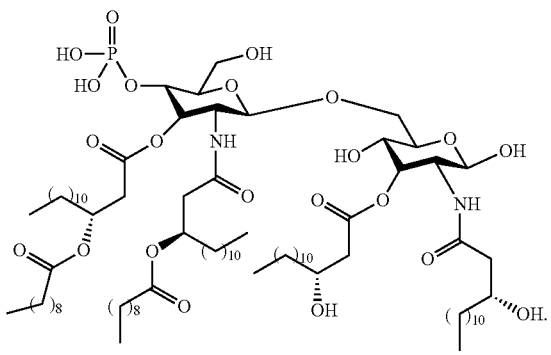

In certain embodiments, the TLR4 agonist is a synthetic GLA adjuvant having the following structure:

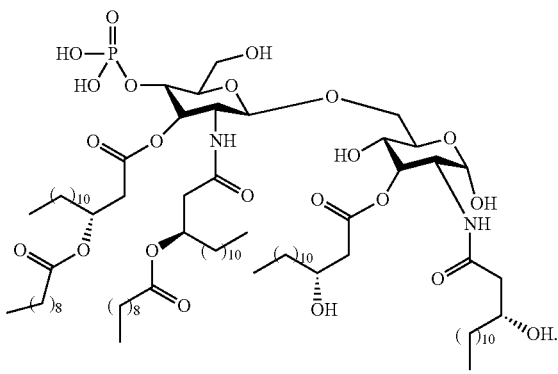

In another embodiment, an attenuated lipid A derivative (ALD) is incorporated into the compositions of the subject invention. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay ($CELD_{50}$) ALDs useful according to the subject invention include monophosphoryl lipid A (MLA) and 3-deacylated monophosphoryl lipid A (3D-MLA). MLA and 3D-MLA are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 U.S. Pat. No. 4,912,094 to Myers, et al., also assigned to Ribi ImmunoChem Research, Inc., embodies 3-deacylated monophosphoryl lipid A and a method for its manufacture. Disclosures of each of these patents with respect to MLA and 3D-MLA are incorporated herein by reference.

Antigen

In some embodiments, the formulations of the invention will also comprise one or more antigens.

An antigen, for use in certain embodiments of the herein described vaccine compositions and methods employing GLA, may be any target epitope, molecule (including a biomolecule), molecular complex (including molecular complexes that contain biomolecules), subcellular assembly, cell or tissue against which elicitation or enhancement of immunreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Preferably and in certain embodiments the vaccine formulations of the present invention contain an antigen or antigenic composition capable of eliciting an immune response against a human or other mammalian pathogen, which antigen or antigenic composition may include a composition derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gp1, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, or M proteins, or combinations thereof).

In certain other preferred embodiments the vaccine formulations of the present invention contain an antigen or antigenic composition capable of eliciting an immune response against a human or other mammlian pathogen, which antigen or antigenic composition may include a composition derived from one or more bacterial pathogens such as Neisseria spp, including N. gonorrhea and N. meningitidis (for example capsular polysaccharides and conjugates thereof, transferrin-binding proteins, lactoferrin binding proteins, PilC, adhesins); S. pyogenes (for example M proteins or fragments thereof, C5A protease, lipoteichoic acids), S. agalactiae, S. mutans: H. ducreyi; Moraxella spp, including M catarrhalis, also known as Branhamella catarrhalis (for example high and low molecular weight adhesins and invasins); Bordetella spp, including B. pertussis (for example pertactin, pertussis toxin or derivatives thereof, filamenteous hemagglutinin, adenylate cyclase, fimbriae), B. parapertussis and B. bronchiseptica; Mycobacterium spp., including M. tuberculosis (for example ESAT6, Antigen 85A, -B or -C), M. bovis, M. leprae, M. avium, M. paratuberculosis, M. smegmatis; Legionella spp, including L. pneumophila; Escherichia spp, including enterotoxic E. coli (for example colonization factors, heat-labile toxin or derivatives thereof, heat-stable toxin or derivatives thereof), enterohemorragic E. coli, enteropathogenic E. coli (for example shiga toxin-like toxin or derivatives thereof); Vibrio spp, including V. cholera (for example cholera toxin or derivatives thereof); Shigella spp, including S. sonnei, S.

dysenteriae, *S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae;* or other bacterial pathogens.

In certain other preferred embodiments the vaccine formulations of the present invention contain an antigen or antigenic composition capable of eliciting an immune response against a human or other mammalian pathogen, which antigen or antigenic composition may include a composition derived from one or more parasites (See, e.g., John, D. T. and Petri, W. A., *Markell and Voge's Medical Parasitology-9th* Ed., 2006, W B Saunders, Philadelphia; Bowman, D. D., *Georgis' Parasitology for Veterinarians-8th* Ed., 2002, W B Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis;* or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis,* and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). Certain embodiments may therefore contemplate vaccine compositions that include an antigen derived from *Schisostoma* spp., *Schistosoma mansonii, Schistosoma haematobium,* and/or *Schistosoma japonicum,* or derived from yeast such as *Candida* spp., including *C. albicans; Cryptococcus* spp., including *C. neoformans*.

Other preferred specific antigens for *M. tuberculosis* are for example Th Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647.

Most preferred antigens for *Chlamydia* include for example the High Molecular Weight Protein (HWMP) (WO 99/17741), ORF3 (EP 366 412), and putative membrane proteins (Pmps). Other *Chlamydia* antigens of the vaccine formulation can be selected from the group described in WO 99128475. Preferred bacterial vaccines comprise antigens derived from *Streptococcus* spp., including *S. pneumoniae* (for example capsular polysaccharides and conjugates thereof, PsaA, PspA, streptolysin, choline-binding proteins) and the protein antigen Pneumolysin (*Biochem Biophys Acta,* 1989, 67, 1007; Rubins et al., *Microbial Pathogenesis,* 25, 337-342), and mutant detoxified derivatives thereof (WO 90/06951; WO 99/03884). Other preferred bacterial vaccines comprise antigens derived from *Haemophilus* spp., including *H. influenzae* type B (for example PRP and conjugates thereof), non typeable *H. influenzae,* for example OMP26, high molecular weight adhesins, P5, P6, protein D and lipoprotein D, and fimbrin and fimbrin derived peptides (U.S. Pat. No. 5,843,464) or multiple copy varients or fusion proteins thereof.

Derivatives of Hepatitis B Surface antigen are well known in the art and include, inter alia, those PreS1, Pars2 S antigens set forth described in European Patent applications EP-A414 374; EP-A-0304 578, and EP 198474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise antigen derived from the Human Papilloma Virus (HPV) considered to be responsible for genital warts (HPV 6 or HPV 11 and others), and the HPV viruses responsible for cervical cancer (HPV16, HPV 18 and others). Particularly preferred forms of genital wart prophylactic, or therapeutic, vaccine comprise L1 particles or capsomers, and fusion proteins comprising one or more antigens selected from the HPV 6 and HPV 11 proteins E6, E7, L1, and L2. Certain preferred forms of fusion protein include L2E7 as disclosed in WO 96/26277, and proteinD(1/3)-E7 disclosed in GB 9717953.5 (PCT/EP98/05285). A preferred HPV cervical infection or cancer, prophylaxis or therapeutic vaccine, composition may comprise HPV 16 or 18 antigens. For example, L1 or L2 antigen monomers, or L1 or L2 antigens presented together as a virus like particle (VLP) or the L1 alone protein presented alone in a VLP or caposmer structure. Such antigens, virus like particles and capsomer are per se known. See for example WO94/00152, WO94/20137, WO94/05792, and WO93/02184.

Additional early proteins may be included alone or as fusion proteins such as E7, E2 or preferably F5 for example; particularly preferred embodiments include a VLP comprising L1E7 fusion proteins (WO 96/11272). Particularly preferred HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such vaccine may optionally contain either or both E6 and E7 proteins front HPV 18, preferably in the form of a Protein D-E6 or Protein D-E7 fusion protein or Protein D E6/E7 fusion protein. The vaccine of the present invention may additionally comprise antigens from other HPV strains, preferably from strains HPV 31 or 33.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

Accordingly, certain herein disclosed embodiment contemplate an antigen that is derived from at least one infectious pathogen such as a bacterium, a virus or a fungus, including an Actinobacterium such as *M. tuberculosis* or *M. leprae* or another *mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus, Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and *Pneumocysti* or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia*, and *Leishmania*.

For example, in GLA-containing vaccine embodiments containing antigens derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Compositions and methods are known in the art for identifying subjects having, or suspected of being at risk for having, an infection with an infectious pathogen as described herein.

For example, the bacterium *Mycobacterium tuberculosis* cases tuberculosis (TB). The bacteria usually attack the lungs but can also attack the kidney, spine, and brain. If not treated properly, TB disease can be fatal. The disease is spread from one person to another in the air when an infected person sneezes or coughs. In 2003, more than 14,000 cases of TB were reported in the United States.

Although tuberculosis can generally be controlled using extended antibiotic therapy, such treatment is not sufficient to prevent the spread of the disease and concerns exist regarding the potential selection for antibiotic-resistant strains. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance. (e.g., U.S. Pat. No. 7,087,713)

Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48 72 hours after injection, which indicates exposure to Mycobacterial antigens. Sensitivity and specificity have, however, been a problem with this test, and individuals vaccinated with BCG cannot be distinguished from infected individuals. (e.g., U.S. Pat. No. 7,087,713)

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-gamma), which, in turn, has been shown to trigger the anti-mycobacterial effects of macrophages in mice. While the role of IFN-gamma in humans is less clear, studies have shown that 1,25-dihydroxy-vitamin D3, either alone or in combination with IFN-gamma or tumor necrosis factor-alpha, activates human macrophages to inhibit *M. tuberculosis* infection. Furthermore, it is known that IFN-gamma stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection, see Chan and Kaufmann, in Tuberculosis: Pathogenesis, Protection and Control, Bloom (ed.), ASM Press. Washington, D.C. (1994).

Existing compounds and methods for diagnosing tuberculosis or for inducing protective immunity against tuberculosis include the use of polypeptides that contain at least one immunogenic portion of one or more *Mycobacterium* proteins and DNA molecules encoding such polypeptides. Diagnostic kits containing such polypeptides or DNA sequences and a suitable detection reagent may be used for the detection of *Mycobacterium* infection in patients and biological samples. Antibodies directed against such polypeptides are also provided. In addition, such compounds may be formulated into vaccines and/or pharmaceutical compositions for immunization against *Mycobacterium* infection. (U.S. Pat. Nos. 6,949,246 and 6,555,653).

Malaria was eliminated in many parts of the world in the 1960s, but the disease still persists and new strains of the disease are emerging that are resistant to existing drugs. Malaria is a major public health problem in more than 90 countries. Nine out of ten cases of malaria occur in sub-Saharan Africa. More than one third of the world's population is at risk, and between 350 and 500 million people are infected with malaria each year. Forty-five million pregnant women are at risk of contracting malaria this year. Of those individuals already infected, more than 1 million of those infected die each year from what is a preventable disease. The majority of those deaths are children in Africa.

Malaria is usually transmitted when a person is bitten by an infected female *Anopheles* mosquito. To transmit the mosquito must have been infected by having drawn blood from a person already infected with malaria. Malaria is caused by a parasite and the clinical symptoms of the disease include fever and flu-like illness, such as chills, headache, muscle aches, and tiredness. These symptoms may be accompanied by nausea, vomiting, and diarrhea. Malaria can also cause anemia and jaundice because of the loss of red blood cells. Infection with one type of malaria, *Plasmodium falciparum*, if not promptly treated, may cause kidney failure, seizures, mental confusion, coma, and death.

An in vitro diagnostic method for malaria in an individual is known, comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed (see, e.g., U.S. Pat. No. 7,087,231).

Expression and purification of a recombinant *Plasmodium falciparum* (3D7) AMA-1 ectodomain have been described. Previous methods have produced a highly purified protein which retains folding and disulfide bridging of the native molecule. The recombinant AMA-1 is useful as a diagnostic reagentas well as in antibody production, and as a protein for use alone, or as part of, a vaccine to prevent malaria. (U.S. Pat. No. 7,029,685)

Polynuclectides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection. (U.S. Pat. No. 6,706,872) Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection (see, e.g., U.S. Pat. No. 6,231,861).

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. (U.S. Pat. No. 7,060,276) Similarly known are the expression and purification of a recombinant *Plasmodium falciparum* (3D7) MSP-$1_{42}$, which retains folding and disulfide bridging of the native molecule. The recombinant MSP-$1_{42}$ is useful as a diagnostic reagent, for use in antibody production, and as a vaccine. (U.S. Pat. No. 6,855,322)

Diagnostic methods for the detection of human malaria infections to identify a subject having or suspected of being at risk for having an infection with a malaria infectious pathogen are thus known according to these and related disclosures. Specifically, for example, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the above-described reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis. Detection of the reduced APAD in the foregoing manner provides a positive indication of malaria infection (e.g., U.S. Pat. No. 5,124,141). In another methodology for diagnosing malaria, a polypeptide comprising a characteristic amino acid sequence derived from the *Plasmodium falciparum* antigen GLURP, is recognized in a test sample by a specific antibody raised against or reactive with the polypeptide. (U.S. Pat. No. 5,231,168).

Leishmaniasis is a widespread parasitic disease with frequent epidemics in the Indian subcontinent, Africa, and Latin America and is a World Health Organization priority for vaccine development. A complex of different diseases, *Leishmania* parasites cause fatal infections of internal organs, as well as serious skin disease. One of the most devastating forms of leishmaniasis is a disfiguring infection of the nose and mouth. The number of cases of leishmaniasis are increasing, and it is now out of control in many areas. Leishmaniasis is also on the rise in some developed countries, specifically southern Europe as a result of HIV infection. Available drugs are toxic, expensive, and require long-term daily injections.

*Leishmania* are protozoan parasites that inhabit macrophages or the white blood cells of the immune system. The parasites are transmitted by the bite of small blood sucking insects (sand flies), which are difficult to control, as they inhabit vast areas of the planet.

Visceral leishmaniasis is the most dangerous of the three manifestations of the disease. It is estimated that about 500,000 new cases of the visceral form (kala-azar or "the killing disease") occur each year. More than 200 million people are currently at risk for contracting visceral leishmaniasis. Over 90 percent of visceral leishmaniasis cases occur in India, Bangladesh, Sudan, Brazil, and Nepal. Most of the deaths occur in children. Those with the cutaneous forms are often left permanently disfigured.

*Leishmania* infections are difficult to diagnose and typically involve histopathologic analysis of tissue biopsy specimens. Several serological and immunological diagnostic assays have, however, been developed. (U.S. Pat. No. 7,008,774; Senaldi et al., (1996) *J. Immunol. Methods* 193:9 5; Zijlstra, et al., (1997) *Trans. R. Soc. Trop. Med. Hyg.* 91:671 673; Badaro, et al., (1996) J. Inf. Dis. 173:758 761; Choudhary, S., et al., (1992) *J. Comm. Dis.* 24:32 36; Badaro, R., et al., (1986) *Am. J. Trop. Med. Hyg.* 35:72 78; Choudhary, A., et al., (1990) *Trans. R. Soc. Trop. Med. Hyg.* 84:363 366; and Reed, S. G., et al., (1990) *Am. J. Trop. Med. Hyg.* 43:632 639). The promastigotes release metabolic products into the culture medium to produce conditioned medium. These metabolic products are immunogenic to the host. See Schnur, L. F., et al., (1972) lsrl. J. Med. Sci. 8:932 942; Sergeiev, V. P., et al., (1969) Med. Parasitol. 38:208 212; El-On, J., et al., (1979) Exper. Parasitol. 47:254 269; and Bray, R. S., et al., (1966) Trans. R. Soc. Trop. Med. Hyg. 60:605 609; U.S. Pat. No. 6,846,648, U.S. Pat. No. 5,912,166; U.S. Pat. No. 5,719,263; U.S. Pat. No. 5,411,865).

About 40 million people around the world are infected with HIV, the virus that causes AIDS. Around 3 million people die of the disease each year, 95 percent of them in the developing world. Each year, close to 5 million people become infected with HW. Currently, sub-Saharan African carries the highest burden of disease, but it is quickly spreading to other countries such as India, China, and Russia. The epidemic is growing most rapidly among minority populations. In the United States there have been more than 950,000 cases of AIDS reported since 1981. AIDS hits people during their most productive years. Women, for both biological and social reasons, have an increased risk for HIV/AIDS.

AIDS is caused by human immunodeficiency virus (HIV), which kills and damages cells of the body's immune system and progressively destroys the body's ability to fight infections and certain cancers. HIV is spread most commonly by having unprotected sex with an infected partner. The most robust solution to the problem is preventing the virus from spreading. Making a safe, effective, and affordable HIV vaccine is one way to reach this goal. Across the world, fewer than one in five people at high risk for HIV infection have access to effective prevention.

Methods for diagnosing HIV infections are known, including by virus culture, PCR of definitive nucleic acid sequences from patient specimens, and antibody tests for the presence of anti-HIV antibodies in patient sera, (see e.g., U.S. Pat. Nos. 6,979,535, 6,544,728, 6,316,183, 6,261,762, 4,743,540.).

According to certain other embodiments as disclosed herein, the vaccine compositions and related formulations and methods of use may include an antigen that is derived from a cancer cell, as may be useful for the immunotherapeutic treatment of cancers. For example, the adjuvant formulation may finds utility with tumor rejection antigens such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 *Current Opinions in Immunology* 8, pps 628-636; Van den Eynde et al., *International Journal of Clinical & Laboratory Research* (1997 & 1998); Correale et al. (1997), *Journal of the National Cancer Institute* 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens are suitable for use with GLA according to certain presently disclosed embodiments include, but are not restricted to, tumor-specific or tumor-associated gangliosides such as $GM_2$, and $GM_3$ or conjugates thereof to carrier proteins; or an antigen for use in a GLA vaccine composition for eliciting or enhancing an anti-cancer immune response may be a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., *Proc. Nat. Acad. Sci. USA* 95(4) 1735-1740 1998), PSMA or, in a preferred embodiment an antigen known as Prostase. (e.g., Nelson, et al., *Proc. Natl. Acad. Sci. USA* (1999) 96: 3114-3119; Ferguson, et al. *Proc. Natl. Acad. Sci. USA* 1999. 96, 3114-3119; WO 98/12302; U.S. Pat. No. 5,955,306; WO 98/20117; U.S. Pat. Nos. 5,840,871 and 5,786,148; WO 00/04149. Other prostate specific antigens are known from WO 98/137418, and WO/004149. Another is STEAP (*PNAS* 96 14523 14528 7-12 1999).

Other tumor associated antigens useful in the context of the present invention include: Plu –1 (*J Biol. Chem* 274 (22) 15633-15645, 1999), HASH-1, HasH-2, Cripto (Salomon et al *Bioessays* 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

The herein disclosed embodiments pertaining to GLA-containing vaccine compositions comprising a cancer antigen will be useful against any cancer characterised by tumor associated antigen expression, such as HER-2/neu expression or other cancer-specific or cancer-associated antigens.

Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohistochemical and immunohistopathological examination of patient samples (e.g., blood, skin biopsy, other tissue biopsy, surgical specimens, etc.), PCR tests for defined genetic (e.g., nucleic acid) markers, serological tests for circulating cancer-associated antigens or cells bearing such antigens, or for antibodies of defined specificity, or other methodologies with which those skilled in the art will be familiar. See, e.g., U.S. Pat. Nos. 6,734,172; 6,770,445; 6,893,820; 6,979,730; 7,060,802; 7,030,232; 6,933,123; 6,682,901; 6,587,792; 6,512,102; 7,078,180; 7,070,931; JP5-328975; Waslylyk et al., 1993 *Eur. J Bioch.* 211(7):18.

Vaccine compositions and methods according to certain embodiments of the present invention may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies, that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells (Akamizu et al., 1996; Kellerman et al., 1995; Raju et al., 1997; and Texier et al., 1992); *pemphigus* is cadherin-like *pemphigus* antigens such as desmoglein 3 and other adhesion molecules (Memar et al., 1996: Stanley, 1995; Plott et al., 1994; and Hashimoto, 1993); and thrombic thrombocytopenic purpura is antigens of platelets. (See, e.g., U.S. Pat. No. 6,929,796; Gorski et al. (Eds.), *Autoimmunity*, 2001, Kluwer Academic Publishers, Norwell, Mass.; Radbruch and Lipsky, P. E. (Eds.) *Current Concepts in Autoimmunity and Chronic Inflammation* (*Curr. Top. Microbiol. and Immunol.*) 2001, Springer, N.Y.)

Autoimmunity plays a role in more than 80 different diseases, including type 1 diabetes, multiple sclerosis, lupus, rheumatoid arthritis, *scleroderma*, and thyroid diseases. Vigorous quantitative estimates of morbidity for most autoimmune diseases are lacking. Most recent studies done in the late 1990s reveal that autoimmune diseases are the third most common major illness in the United States; and the most common autoimmune diseases affect more than 8.5 million Americans. Current estimates of the prevalence of the disease range from 5 to 8 percent of the United States population. Most autoimmune diseases disproportionately affect women. Women are 2.7 times more likely than men to acquire an autoimmune disease. Women are more susceptible to autoimmune diseases; men appear to have higher levels of natural killer cell activity than do women. (Jacobsen et al, *Clinical Immunology and Immunopathology*, 84:223-243, 1997.)

Autoimmune diseases occur when the immune system mistakes self tissues for nonself and mounts an inappropriate attack. The body can be affected in different ways from autoimmune diseases, including, for example, the gut (Crohn's disease) and the brain (multiple sclerosis). It is known that an autoantibody attacks self-cells or self-tissues to injure their function and as a result causes autoimmune diseases, and that the autoantibody may be detected in the patient's serum prior to the actual occurrence of an autoimmune disease (e.g., appearance of clinical signs and symptoms). Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests (e.g., U.S. Pat. Nos. 6,919,210, 6,596, 501, 7,012,134, 6,919,078) while other autoimmune diagnostics may involve detection of a relevant metabolite (e.g., U.S. Pat. No. 4,659,659) or immunological reactivity (e.g., U.S. Pat. Nos. 4,614,722 and 5,147,785, 4,420,558, 5,298, 396, 5,162,990, 4,420,461, 4,595,654, 5,846,758, 6,660, 487).

In certain embodiments, the compositions of the invention will be particularly applicable in treatment of the elderly and/or the immunosuppressed, including subjects on kidney dialysis, subjects on chemotherapy and/or radiation therapy, transplant recipients, and the like. Such individuals generally exhibit diminished immune responses to vaccines and therefore use of the compositions of the invention can enhance the immune responses achieved in these subjects.

In other embodiments, the antigen or antigens used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):S77-121). Exacerbations of COPD are often caused by bacterial (e.g. pneumococcal) infection (Clin Microbiol Rev. 2001 Apr.; 14(2):336-63).

TLR

As described herein, certain embodiments of the present invention contemplate vaccine compositions and immunological adjuvant compositions, including pharmaceutical compositions, that include one or more toll-like receptor agonist (TLR agonist). Toll-like receptors (TLR) include cell surface transmembrane receptors of the innate immune system that confer early-phase recognition capability to host cells for a variety of conserved microbial molecular structures such as may be present in or on a large number of infectious pathogens. (e.g., Armant et al., 2002 *Genome Biol.* 3(8):reviews3011.1-3011.6; Fearon et al., 1996 *Science* 272:50; Medzhitov et al., 1997 *Curr. Opin. Immunol.* 9:4; Luster 2002 *Curr. Opin. Immunol.* 14:129; Lien et al. 2003 *Nat. Immunol.* 4:1162; Medzhitov, 2001 *Nat. Rev. Immunol.* 1:135; Takeda et al., 2003 *Ann Rev Immunol.* 21:335; Takeda et al. 2005 *Int. Immunol.* 17:1; Kaisho et al., 2004 *Microbes Infect.* 6:1388; Datta et al., 2003 *J. Immunol.* 170:4102).

Induction of TLR-mediated signal transduction to potentiate the initiation of immune responses via the innate immune system may be effected by TLR agonists, which engage cell surface TLR. For example, lipopolysaccharide (LPS) may be a TLR agonist through TLR2 or TLR4 (Tsan et al., 2004 *J. Leuk. Biol.* 76:514; Tsan et al., 2004 *Am. J. Physiol. Cell Phsiol.* 286:C739; Lin et al., 2005 *Shock* 24:206); poly(inosine-cytidine) (polyI:C) may be a TLR agonist through TLR3 (Salem et al., 2006 *Vaccine* 24:5119); CpG sequences (oligodeoxynucleotides containing unmethylated cytosine-guanosine or "CpG" dinucleotide motifs, e.g., CpG 7909, Cooper et al., 2005 *AIDS* 19:1473; CpG 10101 Bayes et al. *Methods Find Exp Clin Pharmacol* 27:193; Vollmer et al. *Expert Opinion on Biological Therapy* 5:673; Vollmer et al., 2004 *Antimicrob. Agents Chemother.* 48:2314; Deng et al., 2004 *J. Immunol.* 173:5148) may be TLR agonists through TLR9 (Andaloussi et a., 2006 *Glia* 54:526; Chen et al., 2006 *J. Immunol.* 177:2373); peptidoglycans may be TLR2 and/or TLR6 agonists (Soboll et al., 2006 *Biol. Reprod.* 75:131; Nakao et al., 2005 *J. Immunol.*

174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 *J. Immunol.* 174:1259) may be a TLR7 agonist (Johansen 2005 *Clin. Exp. Allerg.* 35:1591) and/or a TLR8 agonist (Johansen 2005); flagellin may be a TLR5 agonist (Feuillet et al., 2006 *Proc. Nat. Acad. Sci. USA* 103:12487); and hepatitis C antigens may act as TLR agonists through TLR7 and/or TLR9 (Lee et al., 2006 *Proc. Nat. Acad. Sci. USA* 103:1828; Horsmans et al., 2005 *Hepatol.* 42:724). Other TLR agonists are known (e.g., Schirmbeck et al., 2003 *J. Immunol.* 171: 5198) and may be used according to certain of the presently described embodiments.

For example, and by way of background (see, e.g., U.S. Pat. No. 6,544,518) immunostimulatory oligonucleotides containing ummethylated CpG dinucleotides ("CpG") are known as being adjuvants when administered by both systemic and mucosal routes (WO 96/02555, EP 468520, Davis et al., *J. Immunol*, 1998. 160(2):870-876; McCluskie and Davis, *J. Immunol.*, 1998, 161(9):4463-6). CpG is an abbreviation for cytosine-guanosine dinucleotide motifs present in DNA. The central role of the CG motif in immunostimulation was elucidated by Krieg, *Nature* 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., *Proc. Natl. Acad. Sci., USA*, 1998, 95(26), 15553-8).

The preferred oligonucleotides for use in adjuvants or vaccines of the present invention preferably contain two or more dinucleotide CpG motifs separated by at least three, more preferably at least six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Examples of preferred oligonucleotides have sequences that are disclosed in the following publications; for certain herein disclosed embodiments the sequences preferably contain phosphorothioate modified internucleotide linkages:

CPG 7909: Cooper et al., "CPG 7909 adjuvant improves hepatitis B virus vaccine seroprotection in antiretroviral-treated HIV-infected adults." *AIDS,* 2005 Sep. 23; 19(14): 1473-9.

CpG 10101: Bayes et al., "Gateways to clinical trials." *Methods Find. Exp. Clin. Pharmacol.* 2005 Apr.; 27(3):193-219.

Vollmer J., "Progress in drug development of immunostimula-tory CpG oligodeoxynucleotide ligands for TLR9." Expert Opinion on Biological Therapy. 2005 May; 5(5): 673-682

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilising an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phophodiesters. Other internucleotide bonds which stabilize the oligonucleotide may also be used.

Co-Adjuvant

Certain embodiments as provided herein include vaccine compositions and immunological adjuvant compositions, including pharmaceutical compositions, that contain, in addition to GLA, at least one co-adjuvant, which refers to a component of such compositions that has adjuvant activity but that is other than GLA. A co-adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. (See, e.g., Powell and Newman, "Vaccine design—The Subunit and Adjuvant Approach", 1995, Plenum Press, New York) In certain embodiments disclosed herein GLA and a desired antigen, and optionally one or more co-adjuvants, may so alter, e.g., elicit or enhance, an immune response that is directed against the desired antigen which may be administered at the same time as GLA or may be separated in time and/or space (e.g., at a different anatomic site) in its administration, but certain invention embodiments are not intended to be so limited and thus also contemplate administration of GLA in a composition that does not include a specified antigen but which may also include one or more of a TLR agonist, a co-adjuvant, an imidazoquinline immune response modifier, and a double stem loop immune modifier (dSLIM).

Accordingly and as noted above, co-adjuvants include compositions other than GLA that have adjuvant effects, such as saponins and saponin mimetics, including QS21 and QS21 mimetics (see, e.g., U.S. Pat. No. 5,057,540; EP 0 362 279 B1; WO 95/17210), alum, plant alkaloids such as tomatine, detergents such as (but not limited to) saponin, polysorbate 80, Span 85 and stearyl tyrosine, one or more cytokines (e.g., GM-CSF, IL-2, IL-7, IL-12, TNF-alpha, IFN-gamma), an imidazoquinoline immune response modifier, and a double stem loop immune modifier (dSLIM, e.g., Weeratna et al., 2005 *Vaccine* 23:5263).

Detergents including saponins are taught in, e.g., U.S. Pat. No. 6,544,518; Lacaille-Dubois, M and Wagner H. (1996 *Phytomedicine* 2:363-386), U.S. Pat. No. 5,057,540, Kensil, *Crit Rev Ther Drug Carrier Syst,* 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., *Vaccine,* 10(9):572-577, 1992).

Escin is another detergent related to the saponins for use in the adjuvant compositions of the embodiments herein disclosed. Escin is described in the Merck index ($12^{th}$ Ed.: entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin (also known as aescin) have been purified and shown to be biologically active (Yoshikawa M, et al. (Chem Pharm Bull (Tokyo) 1996 August; 44(8): 1454-1464)). Digitonin is another detergent, also being described in the Merck index (12th Ed., entry 3204) as a saponin, being derived from the seeds of *Digitalis purpurea* and purified according to the procedure described by Gisvold et al., *J. Am. Pharm. Assoc.,* 1934, 23, 664; and Rubenstroth-Bauer, *Physiol. Chem.,* 1955, 301, 621.

Other co-adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a GLA vaccine composition or a GLA immunological adjuvant include Pluronic® L121 (BASF Corp., Mount Olive, N. J.; see, e.g., Yeh et al., 1996 *Pharm. Res.* 13:1693; U.S. Pat. No. 5,565,209), CRL1005 (e.g., Triozzi et al., 1997 *Clin Canc. Res.* 3:2355), poly (lactic-co-glycolic acid) (PLGA), poly(lactic acid) (PLA), poly-(D,L-lactide-co-glycolide) (PLG), and polyI:C. (See, e.g., Powell and Newman, "Vaccine design—The Subunit and Adjuvant Approach", 1995, Plenum Press, New York)

Certain embodiments contemplate GLA vaccines and GLA immunological adjuvants that include an oil, which in some such embodiments may contribute co-adjuvant activity and in other such embodiments may additionally or alternatively provide a pharmaceutically acceptable carrier or excipient. Any number of suitable oils are known and may be selected for inclusion in vaccine compositions and immunological adjuvant compositions based on the present disclosure. Examples of such oils, by way of illustration and not limitation, include squalene, squalane, mineral oil, olive oil, cholesterol, and a mannide monooleate.

Immune response modifiers such as imidazoquinoline immune response modifiers are also known in the art and may also be included as co-adjuvants in certain presently disclosed embodiments. Certain preferred imidazoquinoline immune response modifiers include, by way of non-limiting example, resiquimod (R848), imiquimod and gardiquimod (Hemmi et al., 2002 *Nat. Immunol.* 3:196; Gibson et al., 2002 *Cell. Immunol.* 218:74; Gorden et al., 2005 *J. Immunol.* 174:1259); these and other imidazoquinoline immune response modifiers may, under appropriate conditions, also have TLR agonist activity as described herein. Other immune response modifiers are the nucleic acid-based double stem loop immune modifiers (dSLIM). Specific examples of dSLIM that are contemplated for use in certain of the presently disclosed embodiments can be found in Schmidt et al., 2006 *Allergy* 61:56; Weihrauch et al. 2005 *Clin Cancer Res.* 11(16):5993-6001; Modern Biopharmaceuticals, J. Knäblein (Editor). John Wiley & Sons, Dec. 6, 2005. (dSLIM discussed on pages 183 to ~200), and from Mologen A G (Berlin, F R G: [retrieved online on Aug. 18, 2006 at http://www.mologen.com/English/04.20-dSLIM.shtml].

As also noted above, one type of co-adjuvant for use with GLA as described herein may be the aluminum co-adjuvants, which are generally referred to as "alum." Alum co-adjuvants are based on the following: aluminum oxyhydroxide; aluminum hydroxyphophoate; or various proprietary salts. Vaccines that use alum co-adjuvants may include vaccines for tetanus strains, HPV, hepatitis A, inactivated polio virus, and other antigens as described herein. Alum co-adjuvants are advantageous because they have a good safety record, augment antibody responses, stabilize antigens, and are relatively simple for large-scale production. (Edelman 2002 *Mol. Biotechnol.* 21:129-148; Edelman, R. 1980 *Rev. Infect. Dis.* 2:370-383.)

Other co-adjuvants that may be combined with GLA for effective immune stimulation include saponins and saponin mimetics, including QS21 and structurally related compounds conferring similar effects and referred to herein as QS21 mimetics. QS21 has been recognized as a preferred co-adjuvant. QS21 may comprise an HPLC purified non-toxic fraction derived from the bark of *Quillaja Saponaria Molina*. The production of QS21 is disclosed in U.S. Pat. No. 5,057,540. (See also U.S. Pat. Nos. 6,936,255, 7,029, 678 and 6,932,972.)

GLA may also in certain embodiments be combined with "immunostimulatory complexes" known as ISCOMS (e.g., U.S. Pat. Nos. 6,869,607, 6,846,489, 6,027,732, 4,981,684), including saponin-derived ISCOMATRIX®, which is commercially available, for example, from Iscotec (Stockholm, Sweden) and CSL Ltd. (Parkville, Victoria, Australia).

Recombinant Expression Construct

According to certain herein disclosed embodiments, the GLA vaccine composition may contain at least one recombinant expression construct which comprises a promoter operably linked to a nucleic acid sequence encoding an antigen. In certain further embodiments the recombinant expression construct is present in a viral vector, such as an adenovirus, adeno-associated virus, herpesvirus, lentivirus, poxvirus or retrovirus vector. Compositions and methods for making and using such expression constructs and vectors are known in the art, for the expression of polypeptide antigens as provided herein, for example, according to Ausubel et al. (Eds.), Current Protocols in Molecular Biology, 2006 John Wiley & Sons, NY. Non-limiting examples of recombinant expression constructs generally can be found, for instance, in U.S. Pat. Nos. 6,844,192; 7,037,712; 7,052,904; 7,001, 770; 6,106,824; 5,693,531; 6,613,892; 6,875,610; 7,067, 310; 6,218,186; 6,783,981; 7,052,904; 6,783,981; 6,734, 172; 6,713,068; 5,795,577 and 6,770,445 and elsewhere, with teachings that can be adapted to the expression of polypeptide antigens as provided herein, for use in certain presently disclosed embodiments.

Immune Response

The invention thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the invention should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors.

Determination of the induction of an immune response by the vaccines of the present invention may be established by any of a number of well known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (*Immunology Methods Manual: The Comprehensive Sourcebook of Techniques,* 1998; see also *Current Protocols in Immunology*; see also, e.g., Weir, *Handbook of Experimental Immunology,* 1986 Blackwell Scientific, Boston, Mass.; Mishell and Shigii (eds.) *Selected Methods in Cellular Immunology,* 1979 Freeman Publishing, San Francisco, Calif.; Green and Reed, 1998 *Science* 281: 1309 and references cited therein.).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), *Manual of Clinical Laboratory Immunolog,* 5th Ed., 1997 American Society of Microbiology, Washington, D.C.

Accordingly it is contemplated that the vaccine and adjuvant compositions provided herein will be capable of eliciting or enhancing in a host at least one immune response that is selected from a $T_H1$-type T lymphocyte response, a $T_H2$-type T lymphocyte response, a cytotoxic T lymphocyte (CTL) response, an antibody response, a cytokine response, a lymphokine response, a chemokine response, and an inflammatory response. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production one or a plurality of chemokines wherein the chemokine is selected from MIP-1α, MIP-1β, RANTES, CCL4 and CCL5, and a lymphocyte response that is selected from a memory T cell response, a memory B cell response, an effector T cell response, a cytotoxic T cell response and an effector B cell response. See, e.g., WO 94/00153; WO 95/17209; WO 96/02555; U.S. Pat. No. 6,692,752; U.S. Pat. No. 7,084,256; U.S. Pat. No. 6,977,073; U.S. Pat. No. 6,749,856; U.S. Pat. No. 6,733,763; U.S. Pat. No. 6,797,276; U.S. Pat. No. 6,752,995; U.S. Pat. No. 6,057,427; U.S. Pat. No. 6,472,515; U.S. Pat. No. 6,309,847; U.S. Pat. No. 6,969,704; U.S. Pat. No. 6,120,769; U.S. Pat. No. 5,993,800; U.S. Pat. No. 5,595,888; Smith et al., 1987 J Biol Chem. 262:6951; Kriegler et al., 1988 Cell 53:45 53; Beutler et al., 1986 Nature 320:584; U.S. Pat. No. 6,991,791; U.S. Pat. No. 6,654,462; U.S. Pat. No. 6,375,944.

Pharmaceutical Compositions

Provided herein are compositions (including pharmaceutical compositions) comprising oil-in-water emulsions described herein. In some embodiments, the composition further comprises a pharmaceutically acceptable carrier, excipient or diluent. In some embodiments, the pharmaceutical composition is a vaccine composition. The compositions described herein can be administered to a subject for stimulating an immune response in the subject (including non-specific response and antigen-specific response). In some embodiments, the subject is a mammal (e.g., an animal including farm animals (cows, pigs, goats, horses, etc.) and pets (cats, dogs, etc.), or a human). In some embodiments, the subject is a warm-blooded animal.

Pharmaceutical compositions generally comprise GLA (available from Avanti Polar Lipids, Inc., Alabaster, Ala.; product number 699800) and may further comprise one or more components as provided herein that are selected from antigen, TLR agonist, co-adjuvant (including optionally a cytokine, an imidazoquinoline immune response modifier and/or a dSLIM), and/or a recombinant expression construct, in combination with a pharmaceutically acceptable carrier, excipient or diluent.

Therefore, in certain aspects, the present invention is drawn to GLA "monotherapy" wherein GLA, as described herein, is formulated in an emulsion that is substantially devoid of other antigens, and is administered to a subject in order to stimulate an immune response, e.g., a non-specific immune response, for the purpose of treating or preventing a disease or other condition, such as an infection by an organism. In one embodiment, for example, the compositions and methods of the invention employ a monophosphorylated disaccharide for stimulating an immune response in a subject. In another particular embodiment, the compositions and methods employ a 2-monoacyl form of Lipid A for stimulating an immune response in a subject. In another particular embodiment, the GLA is in the form of a spray, optionally provided in a kit.

The GLA may be preferably formulated in a stable emulsion as described herein. In one particular embodiment, for example, a composition is provided comprising a lipid A derivative in a stable emulsion substantially devoid of other antigens. In another particular embodiment, a composition is provided comprising a derivative of 3-acylated monophosphorylated lipid A, suitable for use in mammals, wherein the 2 amine position has a single acyl chain, and that is substantially devoid of other antigens.

In certain other embodiments, the pharmaceutical composition is a vaccine composition that comprises both GLA and an antigen and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For GLA-plus-nucleic acid-based vaccines, or for vaccines comprising GLA plus an antigen, about 0.01 μg/kg to about 100 mg/kg body weight will be administered, typically by the intradermal, subcutaneous, intramuscular or intravenous route, or by other routes.

A preferred dosage is about 1 μg/kg to about 1 mg/kg, with about 5 μg/kg to about 200 μg/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033, 598; 7,018,345; 6,970,739), sonophoretic (e.g., U.S. Pat. Nos. 4,780,212; 4,767,402; 4,948,587; 5,618,275; 5,656, 016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

In another embodiment, a composition of the invention is formulated in a manner which can be aerosolized.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions (including GLA vaccines and GLA immunological adjuvants) may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

As described above, in certain embodiments the subject invention includes compositions capable of delivering nucleic acid molecules encoding desired antigens. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. No. 4,769,330; U.S. Pat. No. 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264:16985-16987, 1989) and lipid-DNA combinations (see Feigner et al., *Proc. Natl. Acad. Sci. USA* 84:7413-7417, 1989).

In addition to direct in vivo procedures, ex vivo procedures may be used in which cells are removed from a host, modified, and placed into the same or another host animal. It will be evident that one can utilize any of the compositions noted above for introduction of antigen-encoding nucleic acid molecules into tissue cells in an ex vivo context. Protocols for viral, physical and chemical methods of uptake are well known in the art.

Accordingly, the present invention is useful for enhancing or eliciting, in a host, a patient or in cell culture, an immune response. As used herein, the term "patient" refers to any warm-blooded animal, preferably a human. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

In certain embodiments a liquid composition intended for either parenteral or oral administration should contain an amount of GLA vaccine composition such that a suitable dosage will be obtained. Typically, this amount is at least 0.01 wt % of an antigen in the composition. When intended for oral administration, this amount may be varied to be between 0.1 and about 70% of the weight of the composition. Preferred oral compositions contain between about 4% and about 50% of the antigen. Preferred compositions and preparations are prepared so that a parenteral dosage unit contains between 0.01 to 1% by weight of active composition.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, Ala.; e.g., product number 699800) of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the invention, the vaccine compositions/adjuvants may be administered through use of insert(s), bead(s), timed-release formulation(s), patch(es) or fast-release formulation(s).

Also contemplated in certain embodiments are kits comprising the herein described GLA vaccine compositions and/or GLA immunological adjuvant compositions, which may be provided in one or more containers. In one embodiment all components of the GLA vaccine compositions and/or GLA immunological adjuvant compositions are present together in a single container, but the invention embodiments are not intended to be so limited and also contemplate two or more containers in which, for example, a GLA immunological adjuvant composition is separate from, and not in contact with, the antigen component. By way of non-limiting theory, it is believed that in some cases administration only of the GLA immunological adjuvant composition may be performed beneficially, whilst in other cases such administration may beneficially be separated temporally and/or spatially (e.g., at a different anatomical site) from administration of the antigen, whilst in still other cases administration to the subject is beneficially conducted of a GLA vaccine composition as described herein and containing both antigen and GLA, and optionally other herein described components as well.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Preferred examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

The following Examples are offered by way of illustration and not by way of limitation.

EXAMPLES

Example 1

Emulsion Adjuvant Dose Titration and TLR4 Agonist Formulation Effects on Immunogenicity of a Recombinant Malaria Vaccine Introduction Oil-in-water (o/w) emulsions have been used safely and successfully as adjuvants in modern vaccines. The most notable o/w emulsions are MF59® and AS03®, which are produced by Novartis and GSK Biologicals, respectively. Both of these adjuvants contain squalene at ~2.5% v/v in the final vaccine formulation [1]. However, until recently only a few reports regarding the motivation for selecting this squalene concentration were published [2-4]. Moreover, a recent study showed that dilution of MF59 did not compromise the immune response in a pandemic influenza vaccine clinical trial [5]. If adjuvant activity can be maintained with a reduction of squalene dose, local reactogenicity of o/w emulsions could potentially be reduced. Furthermore, the vaccine cost could decrease while the available adjuvant supply would increase, thus making vaccine and adjuvant production in resource-poor countries more achievable.

The recombinant malaria antigen PfCelTOS (*Plasmodium falciparum* cell-traversal protein for ookinetes and sporozoites) combined with emulsion adjuvant (Montanide® ISA 720) has demonstrated protective efficacy in 60% of mice in a heterologous challenge model [6]. PfCelTOS inhibits sporozoite motility and hepatocyte infectivity, and could be an important component of next-generation malaria vaccines. Both cellular and humoral immune responses are important for protective efficacy [6, 7].

In this work, we evaluate squalene-based stable emulsion (SE) adjuvant dose effects on humoral and cellular immune responses to PfCelTOS. Moreover, we investigate the effect of including a synthetic TLR4 agonist, glucopyranosyl lipid adjuvant (GLA), in the vaccine formulation. We show that squalene concentrations less than 2% v/v in GLA-SE may induce equivalent adjuvant responses to the 2% v/v squalene concentration. This finding has important implications for vaccine adjuvant production and dosing, as well as novel routes of administration (such as intradermal), which may be more sensitive to oil concentrations. Moreover, we show that the presence of GLA shapes immune activity towards a Th1-type response, eliciting higher levels of IgG2a antibody titers, IFN-γ producing cells, and long-lived antibody-secreting plasma cells, which may be important for vaccine efficacy.

Materials and Methods

Vaccine Formulations.

Shark liver squalene (≥98% purity) was purchased from Sigma-Aldrich (St. Louis, Mo.). Glycerol and α-tocopherol were purchased from Spectrum Chemical (Gardena, Calif.). Poloxamer 188 (Pluronic® F68) was obtained from BASF (Ludwigshafen, Germany) or Spectrum Chemical. Egg phosphatidylcholine (egg PC), 1,2-dipalmitoyl-sn-glycero-3-phosphocholine (DPPC), and glucopyranosyl lipid adjuvant (GLA) were obtained from Avanti Polar Lipids, Inc. (Alabaster, Ala.). Ammonium phosphate buffer components were also obtained from J. T. Baker. The emulsion formulation was prepared by making separate aqueous and oil phases. Poloxamer 188, glycerol, and buffer components were dissolved in the aqueous phase with stirring, whereas egg phosphatidylcholine was dissolved in the oil phase with sonication and heating. Aqueous and oil phases (10% v/v oil) were then mixed with a Silverson Heavy Duty Laboratory Mixer Emulsifier (¾ in. tubular square hole high shear screen attachment; East Longmeadow, Mass.) at ~7,000 RPM for ten minutes to yield a crude emulsion. The crude emulsion was processed through a Microfluidics M110P (Newton, Mass.) high-pressure homogenizer for 12 passes at ~207 MPa (~30,000 psi). The aqueous suspension of GLA was formed by premixing GLA with DPPC at a 4.2:1 molar ratio in organic solvent, followed by solvent evaporation and hydration with ultrapure water. Water-bath sonication at ~70° C. formed the nanoparticle aqueous suspension GLA-AF. Formulations were monitored by size and GLA concentration at 5° C., throughout the duration of the immunization schedule. Particle size was measured by dynamic light scattering as described previously [8]. GLA concentration was monitored by HPLC-CAD [9]. On the day of immunization, the emulsion was diluted with PBS to the specified oil concentrations and mixed with antigen and GLA-AF (where applicable). Montanide® ISA 720 was purchased from Seppic Inc. (Fairfield, N.J.) and was prepared by mixing with 30% v/v aqueous phase prior to immunization. Throughout the manuscript the emulsion dose is referred to as the % v/v of oil in the final vaccine formulation; the ratio of oil to emulsifier is kept constant at all doses. The codon-harmonized recombinant antigen, PfCelTOS, was developed and produced at Walter Reed Army Institute of Research and provided to IDRI as purified bulk in phosphate buffer, courtesy of Dr. Evelina Angov.

Immunology Methods . . .

Endpoint titer was determined using Prism (GraphPad Software, La Jolla, Calif.) following a sigmoidal fit (variable slope) of the values determined at dilution, with the endpoint titer corresponding to a cutoff value (C) determined as described previously [10] with C=$\bar{X}$+SDf, where X is the average and SD is the standard deviation of the negative sera control plate, and f is the multiplier at the 99.9% confidence level. A cutoff value of 0.1 OD was assigned if the cutoff value as determined above was less than 0.1 OD. On rare occasions, individual plate wells registered an abnormally high reading near the highest dilutions. These were excluded from the sigmoidal fit by employing the Grubb's test on the suspect value, comparing to the 4 dilutions surrounding the dilution in question at the 99% confidence level [11].

Results

GLA-AF and SE are stable nanoparticle formulations [12]. GLA-AF is an aqueous nanosuspension of GLA and phospholipid particles. SE is a squalene-based nanoemulsion typically used at 2% v/v squalene for immunization. In order to facilitate emulsion dose titration while keeping GLA concentration constant, GLA-AF was added to the specified concentration of SE immediately prior to immunization for the experimental groups labeled GLA-SE. Average particle sizes of the formulation batches used in the present study are between 88 and 98 nm and are shown in Table 1. In FIG. 1, the concentration of GLA over time in different batches of GLA-AF is shown, demonstrating stability of the TLR agonist concentration for the duration of the in vivo studies described below and at least 6 months. Montanide® ISA 720 is a water-in-oil adjuvant typically used at 70% v/v squalene for immunization, and previously showed significant sterile protection with PfCelTOS in a malaria challenge model [6]. Montanide® ISA 720 is therefore employed as a positive control for the immunogenicity studies described below.

BALB/c mice were immunized 3 times with PfCelTOS vaccine compositions with 3 weeks between injections. FIG. 2 presents the total IgG, IgG1, and IgG2a antibody endpoint titers following the $2^{nd}$ and $3^{rd}$ immunizations. After the $3^{rd}$ immunization (FIG. 2d-f), the impact of SE dose titration was evident in reduced total IgG, IgG1, and IgG2a responses of the 0.02% SE group compared to the 2% SE group. The 0.1% and 0.5% SE groups also showed lower IgG2a response than the 2% SE group. However, the addition of GLA appeared to negate this SE dose titration effect: all GLA-SE groups regardless of emulsion dose elicited equivalent IgG, IgG1, and IgG2a responses. In fact, the GLA-AF group (containing no emulsion) elicited equivalent antibody responses compared to the GLA-SE groups. Clearly, the presence of GLA (whether SE or AF) elicits a stronger IgG2a response compared to the same vaccine composition without GLA. The Montanide® group showed the highest IgG1 responses, although not significantly different compared to the 2% SE or the 0.5% GLA-SE group. Antibody responses after the $2^{nd}$ immunization showed similar patterns as those described above, although overall titers were somewhat lower (FIG. 2a-c). Moreover, several of the GLA-SE groups showed significantly higher IgG2a and IgG1 responses compared to GLA-AF. Finally, higher numbers of antibody-secreting plasma cells in the bone marrow were elicited by vaccines containing GLA (SE or AF), Montanide®, or 2% SE, compared to the antigen alone group (FIG. 2g). Interestingly, 0.02% SE showed reduced levels of antibody-secreting plasma cells compared to the full 2% SE dose, mirroring the IgG antibody endpoint titers.

Figure 3G:
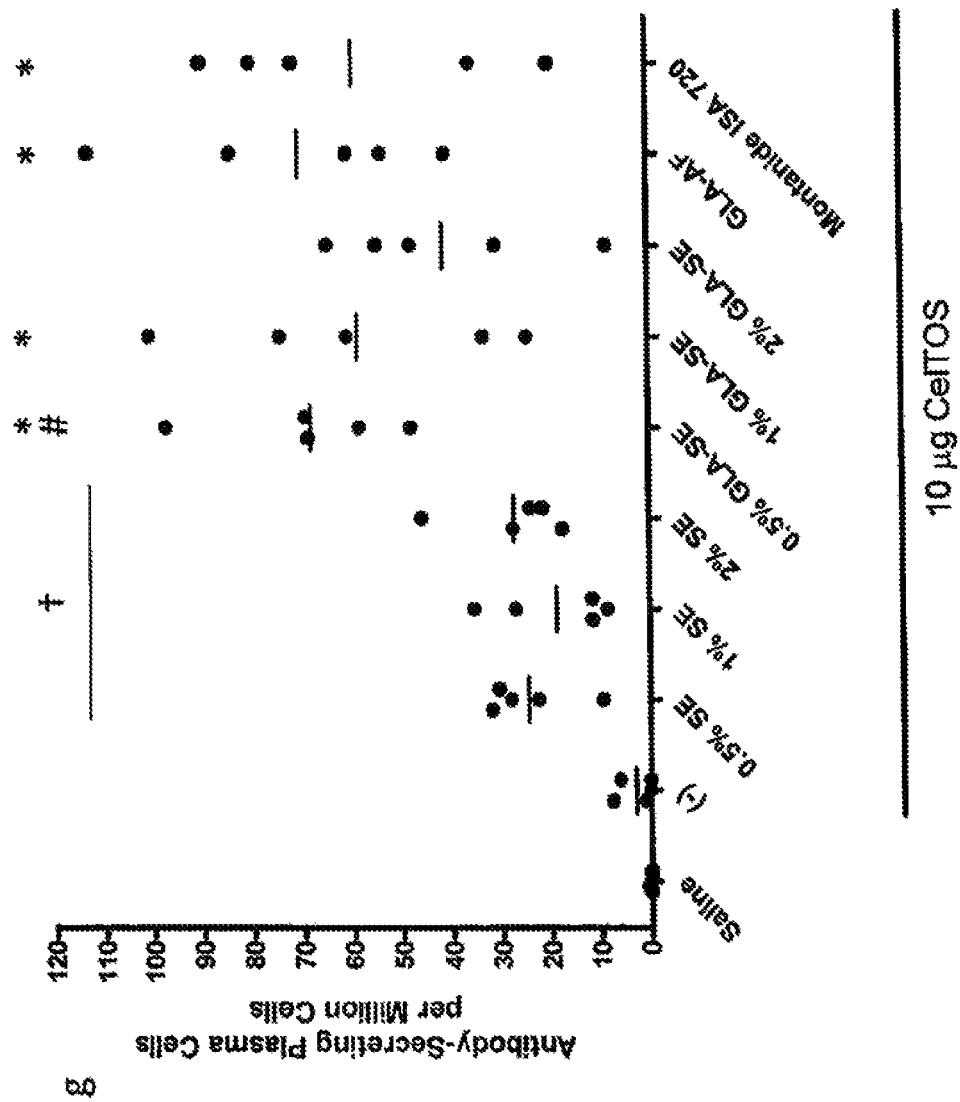

In another experiment, a narrower range of SE dose titration was employed (0.5%-2%), and cellular as well as humoral responses were investigated. In FIG. 3, the total IgG, IgG1, and IgG2a antibody endpoint titers measured after the $2^{nd}$ and $3^{rd}$ immunizations are presented. After the $3^{rd}$ immunization (FIG. 3d-f), all adjuvanted groups showed higher total IgG responses compared to antigen alone. However, the 0.5% dose of SE failed to elicit higher IgG1 antibodies compared to antigen alone, and all SE doses failed to elicit higher IgG2a responses compared to antigen alone. In contrast, all GLA-containing groups showed higher IgG, IgG1, and IgG2a responses compared to antigen alone. GLA dramatically increased IgG2a responses in all groups compared to the same composition without GLA. While the Montanide® group showed significantly higher IgG1 titers compared to all other groups, the GLA-SE groups at the 0.5% and 1% SE doses elicited higher IgG2a responses compared to the Montanide® group. Similar patterns were evident after the $2^{nd}$ immunization (FIG. 3a-c), although the 0.5% SE dose elicited high IgG1 response, in contrast to the post-3$^{rd}$ immunization results. Higher numbers of antibody-secreting plasma cells were elicited with GLA- or Montanide®-containing vaccines (FIG. 3g), although no dose titration effect was evident in the various SE concentrations.

Cellular responses were investigated by cytokine ELISPOT assay. Higher levels of IFN-γ producing cells were elicited by GLA-SE groups at the 1% or 2% SE doses, compared to antigen alone, GLA-AF, SE without GLA, or Montanide® groups (FIG. 4a). In contrast, the GLA-SE groups showed negligible levels of IL-5 secreting cells (FIG. 4b), whereas the 2% SE group elicited higher levels of IL-5 secreting cells than the antigen alone group or the Montanide® group. A similar trend is evident in the multiplex cytokine bead assay results, where production of the Th1 cytokine IFN-γ is induced by the GLA-SE groups, whereas increased Th2 cytokines such as IL-5, IL-10, and IL-13 are associated with the emulsion groups not containing GLA (FIG. 5). The 2% SE dose elicited the highest Th2 cytokine cellular responses (e.g. IL-5 and IL-13).

Discussion

Inclusion of GLA in the vaccine compositions above shapes the immune response towards a Th1 bias as demonstrated by significantly higher IgG2a antibodies and IFN-γ production. Although total antibody production was not found to correlate to protective efficacy in earlier CelTOS studies, antibody isotype analysis was not performed [6, 7]. Therefore, it is unclear whether higher IgG2a antibody production signifies increased protective potential. However, IFN-γ production does appear to be related to vaccine efficacy [6, 7]. Thus, GLA-SE adjuvants may be good candidates for generating protective efficacy in CelTOS vaccines. We note here that the emulsion appears to be necessary for IFN-γ production (i.e. GLA-SE groups), while antibody titers elicited by GLA-AF groups were similar to GLA-SE groups after a 3$^{rd}$ immunization. Interestingly, reduction of the emulsion dose from 2% to 1% did not reduce IFN-γ or antibody production in GLA-SE groups. Finally, inclusion of GLA also induced significantly higher long-lived antibody-secreting cells compared to antigen alone. Overall, GLA shapes the immune response towards a Th1 bias and induces higher numbers of antibody-secreting plasma cells in the bone marrow, although it appears that less than 2% emulsion concentrations may be sufficient for these effects.

In emulsion groups not containing GLA, the effects of reduced adjuvant concentration were more apparent. Thus, levels of IL-5 producing cells were lower in the 1% SE group compared to the 2% SE group, and only the 2% SE group showed higher amounts of IL-13 compared to antigen alone. The effect of emulsion dose titration was demonstrated in the antibody endpoint titers, especially in the lowest emulsion concentration group (0.02% SE), which elicited lower IgG, IgG1, and IgG2a, as well as lower levels of antibody-secreting plasma cells compared to the 2% SE group. However, SE concentrations of 0.5% and 1% appeared to elicit similar levels of IgG and IgG1 antibody titers as well as similar levels of antibody-secreting plasma cells compared to the full 2% SE dose. However, the overall immune response appears to be somewhat reduced with lower concentrations of SE, especially at the highest dilution of 0.02%.

Reduction of emulsion concentration in vaccines can have multiple applications, such as cost-saving, reduced local reactogenicity, alternative routes of delivery, and facilitating immunization of young children. We have shown that adjuvants containing lower amounts of emulsion in the presence of a TLR4 agonist may produce equivalent immune responses to the full 2% oil emulsion dose. Recent clinical studies have evaluated adjuvant dose effects using the leading oil-in-water emulsion products MF59® and AS03, both approved for use in Europe, although neither formulation contains a TLR agonist. Thus, a pandemic influenza vaccine clinical trial found that the typical ~2.3% oil dose of the MF59® adjuvant could be reduced by half (but not by 4-fold) without compromising immunogenicity and still meeting the European criteria for pandemic vaccine licensure [5]. Furthermore, a dose-dependent decrease in injection site pain was noted in trial participants. In contrast, a study employing seasonal influenza antigen and MF59® at doses of 0.125, 0.25, 0.5 or full dose in 6 to 36 month old children found no difference in reactogenicity was between the different adjuvant doses [4]. Antibody responses followed a dose response according to adjuvant concentration, although all formulations met the European Committee for Medicinal Products for Human Use (CHMP) criteria after the 2$^{nd}$ immunization.

Two different doses of AS03 (AS03A containing full dose of 2.5% squalene and 2.5% α-tocopherol vs. AS03B containing half dose) were evaluated in another influenza clinical trial, where it was concluded that while initial immune responses elicited by the two different adjuvant doses were equivalent, the durability of response measured at 182 days post-vaccination was somewhat better with the higher adjuvant dose [3]. Furthermore, the 41-64 years age group showed significantly reduced antibody responses at the lower adjuvant dose. Finally, modest pain reduction was noted at the lower adjuvant dose compared to the full dose. Taken together, the MF59® and AS03 clinical trials demonstrate that the effect of adjuvant dose titration may depend on each vaccine composition and its intended recipients.

Conclusion

PfCelTOS vaccines containing GLA-SE adjuvant elicit strong Th1-type immune responses (including higher IFN-γ production than a PfCelTOS vaccine containing Montanide® ISA 720) in BALB/c mice. Emulsion dose may be reduced from 2% to 1% without compromising immunogenicity in the GLA-SE adjuvant groups. In general, reduction of emulsion dose in SE groups (not containing the TLR4 agonist GLA) showed somewhat reduced immunogenicity, especially at the lowest adjuvant dose dilution (0.02%). Results from protection studies using PfCelTOS with GLA-SE adjuvant are being compiled for a subsequent publication, and a phase I clinical trial is planned for 2012.

References

[1] Fox C B. Squalene emulsions for parenteral vaccine and drug delivery. Molecules 2009; 14:3286-312.

[2] Ott G, Barchfeld G L, Chernoff D, Radhakrishnan R, van Hoogevest P, Van Nest G. MF59: design and evaluation of a safe and potent adjuvant for human vaccines. In: Powell M F, Newman M J, editors. Vaccine Design: The Subunit and Adjuvant Approach. New York: Plenum Press, 1995: 277-96.

[3] Langley J M, Frenette L, Ferguson L, Riff D, Sheldon E, Risi G, et al. Safety and cross-reactive immunogenicity of candidate AS03-adjuvanted prepandemic H5N1 influenza vaccines: A randomized controlled phase 1/2 trial in adults. J Infect Dis 2010; 201:1644-53.

[4] Cioppa G D, Vesikari T, Sokal E, Lindert K, Nicolay U. Trivalent and quadrivalent MF59-adjuvanted influenza vaccine in young children: A dose- and schedule-finding study. Vaccine 2011; 29:8696-704.

[5] Keitel W, Groth N, Lattanzi M, Praus M, Hilbert A K, Borkowski A, et al. Dose ranging of adjuvant and antigen in a cell culture H5N1 influenza vaccine: Safety and immunogenicity of a phase 1/2 clinical trial. Vaccine 2010; 28:840-8.

[6] Bergmann-Leitner E S, Mease R M, De La Vega P, Savranskaya T, Polhemus M, Ockenhouse C, et al. Immunization with pre-erythrocytic antigen CelTOS from *Plasmodium falciparum* elicits cross-species protection against heterologous challenge with *Plasmodium berghei*. PLoS One 2010; 5:e12294.

[7] Bergmann-Leitner E S, Legler P M, Savranskaya T, Ockenhouse C, Angov E. Cellular and humoral immune effector mechanisms required for sterile protection against sporozoite challenge induced with the novel malaria vaccine candidate CelTOS. Vaccine 2011; 29:5940-9.

[8] Fox C B, Baldwin S L, Duthie M S, Reed S G, Vedvick T S. Immunomodulatory and physical effects of oil composition in vaccine adjuvant emulsions. Vaccine 2011; 29:9563-72.

[9] Anderson R C, Fox C B, Dutill T S, Shaverdian N, Evers T L, Poshusta G R, et al. Physicochemical characterization and biological activity of synthetic TLR4 agonist formulations. Coll Surf B: Biointerfaces 2010; 75:123-32.

[10] Frey A, Di Canzio J, Zurakowski D. A statistically defined endpoint titer determination method for immunoassays. J Immunological Methods 1998; 221:35-41.

[11] Hibbert D B, Gooding J J. Data Analysis for Chemistry. New York: Oxford University Press, 2006.

[12] Coler R N, Bertholet S, Moutaftsi M, Guderian J A, Plessner Windish H, Baldwin S L, et al. Development and characterization of synthetic glucopyranosyl lipid adjuvant system as a vaccine adjuvant. PLoS ONE 2011; 6:e16333.

Example 2

Immunomodulatory and Physical Effects of Phospholipid Composition in Vaccine Adjuvant Emulsions Introduction Metabolizable oil-in-water emulsions have been demonstrated to be safe and effective vaccine adjuvants, nutritional supplements, and drug delivery vehicles. Various emulsifier compositions exist, with squalene being the preferred metabolizable oil for vaccine adjuvant applications (1-3). Commonly used emulsifiers include Pluronics®, Tweens®, Spans®, and phospholipids. Emulsifier selection is based on emulsion stabilizing capacity and/or biological activity, since emulsifiers are membrane-active by definition and have been shown to have various biological effects related to immune stimulation (4).

Lecithin and its main component, phosphatidylcholine (PC), have been successfully utilized as emulsifiers in safe and effective parenterally delivered emulsions. Perhaps the widest use of phospholipid emulsifiers is in the application of intravenous nutritional supplementation (5), such as in Intralipid®, a soybean oil/egg lecithin emulsion. However, there may be some disadvantages associated with egg lecithin (or egg PC) as an emulsifier, and advantages to substituting egg-derived phospholipids with synthetic phospholipids. First, there is considerable heterogeneity of structure: egg PC may contain at least 17 different PC species (6), whereas various synthetic PCs are available commercially at 99% purity. Second, egg lecithin consists of multiple mono-unsaturated and polyunsaturated acyl chains, which are prone to oxidative degradation, whereas various synthetic PCs are composed of saturated acyl chains and are therefore more chemically stable (7). Third, the egg phospholipids are derived from an animal source instead of being synthetically produced.

We have previously published the physical stability profile of squalene emulsions stabilized by egg PC (8, 9). Moreover, we showed that synthetic POPC (a main component of egg PC) provided equivalent stability to a squalene emulsion compared to egg PC. However, no other synthetic PCs were evaluated. Synthetic, homogeneous phospholipids have become widely available and are now relatively inexpensive. By appropriate selection of synthetic phospholipid, the chemical stability of the emulsifier and the physical stability of the emulsion could be optimized. Biological equivalence must also be addressed; changes in source or purity of emulsifiers in vaccine adjuvant emulsions have previously been shown to dramatically affect vaccine potency (10, 11). In the present manuscript, we seek to 1) build on our previous work by evaluating the physical stability of squalene emulsions containing other synthetic PCs (besides POPC), and 2) compare the biological activity of the synthetic PC emulsions as well as an egg PC emulsion in the context of malaria and influenza vaccine formulations.

Materials and Methods

Adjuvant Formulations.

Shark liver squalene (>98% purity) was purchased from Sigma-Aldrich (St. Louis, Mo.). Egg phosphatidylcholine (egg PC), 1-palmitoyl-2-oleoyl-sn-glycero-3-phosphocholine (POPC), 1,2-dioleoyl-sn-glycero-3-phosphocholine (DOPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), and 1,2-dilauroyl-sn-glycero-3-phosphocholine (DLPC) were obtained from Avanti Polar Lipids, Inc. at 99% purity (Alabaster, Ala.). All emulsion formulations were prepared by high-speed mixing an oil phase (containing squalene and phospholipid) and an aqueous phase via high-pressure homogenization, as described previously (8). The final concentration of phospholipid was 25 mM. Formulations were monitored for stability over 6 months at 5° C., room temperature (RT), 37° C., and 60° C. Particle size, zeta potential, viscosity, hemolysis, and light scattering optical profiling measurements were performed as described previously (8). Briefly, particle size was determined at the indicated timepoints by diluting an aliquot of each emulsion 1:100 fold in water and measuring the scattering intensity-biased size average (Z-avg) by dynamic light scattering (Malvern Zetasizer APS). Zeta potential was measured shortly after emulsion manufacture by diluting an aliquot of each emulsion 1:20 fold in water and measuring zeta potential by microelectrophoresis (Malvern Zetasizer Nano-ZS). A 20-mL sample of each emulsion was removed from storage at 5° C. and allowed to equilibrate to room temperature before measuring viscosity by a rotational viscometer (Brookfield DV-E). Emulsion hemolytic activity was assayed following a modified version of a previously published technique (12); a suspension of red blood cells from a human volunteer was mixed in saline with each emulsion for ~20 min, following which the sample was centrifuged, the supernatant was diluted into an ethanol:HCl (39:1, v:v) mixture, and the absorbance was measured at 398 nm. Laser scattering optical profiling measurements were collected every 10 min for 4 hrs on undiluted emulsion samples at 60° C. using a 870-nm laser and a charge-coupled detector (LUMiReader).

Immunization, Serum Collection, and Immunological Assays.

Female, six-seven week old, BALB/c mice, (Charles River Laboratories, Wilmington, Mass.) were immunized by intramuscular injection in each hind quadricep. Two distinct antigens were tested: 1) 2007-2008 Fluzone inactivated split-virus vaccine, incorporating the representative influenza strains A/Solomon Islands/2/2006 (H1N1), A/Wisconsin/67/2005 (H3N2) and B/Malaysia/2506/2004; and 2) recombinant *Plasmodium berghei* circumsporozoite protein (PbCSP) produced in-house using the codon harmonized construct developed by Walter Reed Army Institute of Research. Influenza and malaria vaccine formulations, immunization regimens, and serum collection were as described earlier (8), except that the influenza antigen dose was 0.02 µg total HA. All procedures were performed under specific pathogen-free conditions and in accordance with the regulations and guidelines of the IDRI animal care and use committee.

Antibody Responses.

Mice were immunized twice, three weeks apart. Sera were analyzed for antigen-specific IgG, IgG1, IgG2a antibodies, and hemagglutination inhibition (HI) antibody activity, as described previously, with arbitrary anti-PbCSP units assigned by comparison with a standard curve whereas endpoint titers were determined for influenza antibodies (8). A bone marrow ELISPOT assay was used to determine the induction of vaccine specific long-lived antibody-secreting plasma cells in samples collected four weeks following the Fluzone boost immunization with and without adjuvant as previously described with minor modifications (13).

Antigen-Specific Cytokine Responses.

MultiScreen 96-well filtration plates (Millipore, Bedford, Mass.) were coated with rat anti-mouse IL-5 capture Ab (eBioscience, San Diego, Calif.) and incubated overnight at 4° C. Plates were washed with PBS, blocked with RPMI 1640 and 10% FBS for at least 1 hour at RT, and then washed again. Spleens were harvested four weeks after the second Fluzone injection. Single cell suspensions were prepared and seeded at $2\times10^5$ cells per well in duplicate with either media alone, concanavilin A (0.75 □g/m), 5 hemagglutinating units (HAU) inactivated A/Solomon Islands/2/2006 (H1N1) or 2 HAU inactivated A/Wisconsin/67/2005(H3N2) for 48 hours at 37° C. The plates were then washed with 0.1% PBS-Tween 20 and incubated overnight with a biotin-conjugated rat anti-mouse IL-5 secondary Ab (eBioscience). The filters were developed using the VectaStain ABC avidin peroxidase conjugate and Vectastain AEC substrate kits according to the manufacturer's protocol (Vector Laboratories). The reaction was stopped by washing the plates with deionized water, plates dried in the dark, and spots counted using an automated ELISPOT reader (C.T.L. Serie3A Analyzer, Cellular Technology Ltd.). Data were analyzed using ImmunoSpot® software (CTL Analyzer LLC).

Statistical Analysis.

All mouse experiments analyzed five individual animals per group per timepoint. ELISPOT counts and $\log_{10}$-transformed antibody titers were compared using ANOVA with Tukey's multiple comparison test. HI titers were compared by ANOVA with Tukey's multiple comparison test using the log 2-transformed HI titers.

Results

Physical Stability of Emulsions.

Table 1 describes the composition of the emulsifiers employed in this study. Egg PC is a heterogeneous phosphatidylcholine mixture with various acyl chain lengths and degrees of saturation, although a major component has been identified as POPC (6, 14). In contrast, the synthetic phospholipids shown in Table 1 are highly pure (≥99%) and have well defined main phase transition temperatures ($T_m$) as lipid assemblies. DOPC and POPC, which both contain monounsaturated acyl chains, have low phase transition temperatures (<0° C.) due to the packing disorder imposed by the unsaturated chains. Egg PC, which contains monounsaturated and polyunsaturated acyl chains, also has a low $T_m$. DLPC consists of saturated acyl chains but they are only 12 carbons in length, which results in a low $T_m$. DMPC, DPPC, and DSPC have longer saturated acyl chains (14, 16, and 18 carbons, respectively) and their phase transition temperatures increase according to chain length. For example, DPPC configuration at room temperature is the highly ordered gel phase, whereas above 41° C. the lipid forms a liquid crystalline phase which is characterized by more packing disorder due to temperature-induced changes in acyl chain conformation (15).

Table 2 displays the physical and hemocompatibility properties of the emulsions shortly after their manufacture. The viscosity values are close to that of water (~1 cP), indicative of the low oil content in these emulsions (10% v/v when viscosity is measured, but diluted to 2% v/v for immunization). Zeta potential values are negative for emulsions employing phospholipids with low $T_m$ values (e.g. DOPC, DLPC), whereas emulsions with higher $T_m$ phospholipids are positive (DSPC, DPPC). None of the emulsions displays notable hemolytic activity when incubated with a suspension of RBCs, although the DLPC emulsion appears slightly more hemolytic than the others.

We recently reported that particle size stability of a synthetic POPC-squalene emulsion stored at 5° C. or room temperature was equivalent or improved compared to an egg PC-squalene emulsion (9). We sought to build on this work by manufacturing squalene emulsions with various other synthetic phospholipids besides POPC; FIG. 1 shows the particle size stability of the emulsions stored at different temperatures. The initial size of the POPC emulsion was reported earlier (9); here, we have monitored the long-term stability of this same lot for comparison to the other synthetic PC emulsions. Obvious anomalies in physical appearance such as phase separation qualified emulsions as visually unstable. Taking into account data from all temperatures, the DMPC and POPC emulsions demonstrated greater particle size stability than the other emulsions studied. Minimal particle size change was evident at 5° C., and gradual particle size change was apparent with increasing temperature (FIG. 1). Comparatively, the DOPC emulsion droplet size change was minimal at 5° C., but noticeable at the higher storage temperatures. DPPC emulsion stability was highly dependent on temperature. When stored above the DPPC $T_m$ (41° C.), the DPPC emulsion showed good stability compared to the other emulsions. However, at the three storage temperatures below the $T_m$, the DPPC emulsion was either visually unstable or showed more particle size change than more stable emulsions. Interestingly, the DLPC emulsion, containing the shortest saturated chain emulsifier, was visually unstable at early timepoints at all four storage temperatures. The DSPC emulsion also became visually unstable before the 6-month timepoint at all storage temperatures. Size polydispersity values were similar among the more stable emulsions (Supplementary FIG. 1).

Laser scattering optical profiling provides complementary information regarding emulsion stability. Changes in the emulsion due to creaming, coalescence, etc. are detected as changes in light transmission through the vertical profile of the emulsion (8). The laser scattering optical profiles of the emulsions were measured every 10 minutes over a period of 4 hours at 60° C. (Supplementary FIG. 2). In order to compare data from different emulsions, the integral transmission between a specific region (25 to 30 mm) in the vertical profile of the sample are plotted in FIG. 2. A decrease in integral transmission is indicative of coalescence or particle size growth since larger particles will scatter more light, allowing less to be transmitted to the detector. An increase in integral transmission is generally representative of creaming or phase separation. The DMPC emulsion shows little change compared to the POPC or DOPC emulsions, indicating superior stability at this temperature. These optical profile data confirm the particle size and visual stability observations described above. DLPC, DPPC, and DSPC emulsions are not shown since these emulsions were already classified as visually unstable at 5° C. before the optical profiling measurements had been conducted.

Taken together, the physical stability data indicate that among the synthetic lipids DMPC, POPC, and to a lesser extent DOPC are the most effective emulsifiers of squalene oil. Particle size and SDS-PAGE analysis following mixing the emulsions with an inactivated influenza vaccine indicated good compatibility (data not shown). Therefore, the above stable synthetic PC emulsions, along with an egg PC emulsion, were subsequently evaluated for biological activity in a mouse model.

Emulsions Selectively Enhance Antibody Responses to a Recombinant Malaria Protein.

Antibody responses against a recombinant malaria antigen, *Plasmodium berghei* circumsporozoite protein (PbCSP), were measured in individual mouse sera two weeks after a second immunization with protein alone or with protein combined with emulsion formulations. The anti-PbCSP IgG antibody levels were significantly higher in mice immunized with PbCSP injected in the presence of emulsions than mice receiving protein alone (FIG. 3a, p-values<0.05). IgG1 antibodies were also higher in mice immunized with PbCSP with egg PC, POPC, and DMPC emulsions compared to mice immunized with protein alone (FIG. 3b, p-values<0.05). In contrast, differences between the various groups were not detected in the anti-PbCSP IgG2a antibody levels (FIG. 3c, p-values>0.05). These data indicate that antigen-specific IgG1 antibodies are selectively enhanced by including emulsions during exposure to antigen.

Emulsions Enhance Antibody Responses to Influenza Proteins.

We have previously observed elevated antibody responses in animals injected with Fluzone formulated with emulsions incorporating egg-derived PC (8, 13), but have not investigated if these effects are observed when synthetic lipids are incorporated. To determine if emulsions elevated the antibody response to native influenza proteins, we immunized mice with a low dose of Fluzone vaccine in the presence or absence of emulsion formulation incorporating natural or synthetic phospholipids. Compared to vaccination with the Fluzone vaccine alone, total IgG, IgG1, and IgG2a antibody titers were higher for all groups that received Fluzone with emulsion formulations (FIG. 4).

We also assessed the effect of emulsion formulations on the generation of antigen-specific antibody secreting plasma cells (ASPC) within the bone marrow, as these long-lived cells secrete antibody for extended periods of time after antigenic exposure and can provide a basis for long-term protection. Overall, our results indicate that similar numbers of ASPC were generated among the various emulsion formulation groups. Only the vaccine containing DOPC emulsion, however, induced a significantly higher number of long-lived plasma cells than Fluzone vaccine alone (FIG. 4d).

The hemagglutination inhibition (HI) assay is a meaningful predictive indicator of influenza vaccine efficacy, with a titer of generally considered enough to provide protection (16). To determine if emulsion formulations could generate higher quality antibodies capable of enhancing protection afforded by the Fluzone vaccine, we compared HI titers of mice vaccinated with Fluzone alone or Fluzone with various emulsion formulations. When measured 4 weeks after the final immunization, the addition of emulsion formulation induces higher HI titers than the Fluzone vaccine alone against both the A/Solomon Islands/3/2006 (H1N1) and the A/Wisconsin/67/2005 (H3N2) vaccine components (FIG. 5). Against the A/Solomon Islands/3/2006 (H1N1) component, all vaccines containing emulsion induced higher HI titers than Fluzone alone. Against the A/Wisconsin/67/2005 (H3N2) component, egg PC and DOPC emulsions induced higher HI titers than Fluzone alone.

Additional experiments indicated that, with the exception of the DMPC emulsion, increased numbers of antigen-specific T cells from mice immunized with Fluzone plus emulsions secreted greater levels of IL-5 than cells from mice immunized with Fluzone alone (FIG. 6, p-values<0.05). Together, the antibody and cytokine secretion data indicate an enhanced Th2-type immune response is elicited by the vaccines containing these emulsions.

Discussion

Antibody responses elicited with both the malaria and influenza vaccines were enhanced in an equivalent matter regardless of synthetic or egg-derived PC as emulsifier components. This finding is meaningful for continued development of PC-emulsified emulsions based on synthetic instead of natural components. The literature has shown why the biological equivalence of this type of component substitution should not be taken for granted; there are several instances when substitution of one phospholipid emulsifier with another has resulted in differences in biological activity. For instance, Yasuda et al. found that liposomes composed of synthetic phosphatidylcholines showed a direct correlation between immunogenicity (as indicated by the number of antibody-secreting cells in the spleen) and lipid phase transition temperature when used to immunize mice intraperitoneally with a synthetic lipid-based antigen; higher phase transition was found to directly correlate with increased immunogenicity (17). This correlation between phase transition temperature and immunogenicity was not apparent in the current work, although the phospholipids with the highest phase transition temperatures (DPPC and DSPC) were not evaluated immunologically due to poor emulsion stability. In another example of the importance of emulsifier source, recent clinical trial results with a water-in-oil vaccine adjuvant emulsion, Montanide® ISA 51, revealed that the replacement of animal-source emulsifier with plant-source material may have been the cause for significantly reduced in vivo efficacy (11). The immunological data in the present work demonstrate that influenza and malaria vaccines adjuvanted with emulsions made with different natural or synthetic phosphatidylcholines elicit similar antibody responses. Moreover, the qualitative immunogenicity of the emulsions employed in this work are in line with literature reports; for instance, emulsions (without TLR agonists) appear to induce only modest increases in IgG2a responses compared to antigen alone (18). Subtle differences were evident between emulsions in experiments with the influenza vaccine, illustrating that the lipid emulsifiers may differ slightly in biological effects. However, in general, it appears that egg PC can be replaced by synthetic phospholipids without a detrimental effect on biological activity in the context of a simple recombinant antigen malaria vaccine or a more complex inactivated split-virus influenza vaccine.

Besides biological activity, it is important to consider physical emulsion stability as it relates to emulsifier acyl chain structure. It has occasionally been reported that purified PC molecules do not effectively stabilize emulsions (19). For example, a DOPC:DPPC:DPPE synthetic mix did not produce emulsions as stable as that observed with egg lecithin when used to emulsify perfluorocarbons (20). However, the claim that pure synthetic PCs do not emulsify effectively is easily refuted by other reports (21), which make clear that stability is dependent on the structure and properties of both oil and emulsifier (22). The spontaneous curvature or packing structure of the emulsifiers determine their effectiveness in stabilizing emulsions (21). Emulsifier spontaneous curvature or packing is affected by a) the phospholipid phase behavior, b) the degree of unsaturation of the lipid acyl chains, and c) the phospholipid miscibility in the oil (21). In the present work, the importance of lipid phase transition is apparent since emulsions containing the phospholipids with the highest phase transition temperatures (DPPC and DSPC) were not stable at most storage temperatures based on size and visual appearance. Interestingly, DPPC produced a stable emulsion only when stored above its main phase transition temperature. Nevertheless, phase transition temperature was not the only determining factor for physical stability; note that the DMPC emulsion showed good stability (at all storage temperatures, including temperatures above and below the phase transition) compared to the DLPC emulsion even though DMPC has a higher phase transition temperature. Thus, the complexity of the emulsifier-oil interactions is evidenced by the fact that the stability of the emulsions described in the present work could not be predicted solely based on phospholipid phase transition temperature, acyl chain length, or saturation. Likewise, the effect of lipid phase transition temperature and acyl chain structure on emulsion stability was difficult to predict in the context of glyceryl trioctanoate emulsions: DLPC, DMPC, and DPPC emulsions were more stable than DSPC, 1,2-dilinoleoyl-sn-glycero-3-phosphocholine, and DOPC emulsions (23).

Emulsion droplet size growth can occur by two mechanisms: Ostwald ripening (Laplace pressure differences cause oil molecules to diffuse from smaller droplets to larger droplets), or coalescence (separate oil droplets merge and form a single droplet) (24). Since squalene is essentially insoluble in water, it is unlikely that Ostwald ripening is responsible for the size growth in the emulsions of the present work (25-28). Thus, coalescence is the likely mechanism for the size growth reported here. The rate of coalescence is expected to increase with higher temperatures due to increased rates of diffusion and droplet interaction events, and the size data presented here is consistent with this expectation. Emulsifiers that do not provide an effective steric or electrostatic stabilization to the oil droplet via a well-packed interfacial layer may be responsible for increased rates of coalescence. Our findings indicate that, overall, the unsaturated lipid emulsifiers were more effective than the saturated lipids in stabilizing squalene emulsions, with the exception of DMPC which produced a highly stable emulsion even though it contains only saturated acyl chains. This emphasizes again that it is difficult to predict emulsion stability based solely on the phase transition and acyl chain structure of the phospholipid emulsifiers.

Finally, we note that various physical characterization data shown in this manuscript correlate well with previous literature reports. For example, the relationship of more negative zeta potential values for liquid crystalline phase lipids versus gel phase lipids has been reported previously; it is attributed to increased disorder and packing defects in liquid phase membranes which causes exposure of the polar headgroups and allows for more available binding sites for solution anions (29, 30). Furthermore, the slightly increased hemolytic tendency of the DLPC emulsion corresponds with another report from the literature that DLPC and other short-chain phospholipids induce hemolysis via creation of non-specific pores in lipid bilayers through lipid phase separation, allowing permeation of ions (31).

Conclusion

In the present work, it was shown that vaccine adjuvant emulsions containing squalene oil and synthetic phospholipid emulsifiers, namely DMPC or POPC, demonstrated long-term particle size stability at various temperatures. In general, egg PC and synthetic PC emulsions induced similar immune responses in combination with a simple recombinant malaria antigen or an inactivated split-virus influenza vaccine. Thus, substitution of egg phosphatidylcholine with synthetic phosphatidylcholine did not result in loss of vaccine adjuvant biological activity. Ongoing work in our laboratory will compare stability and immunogenicity of squalene-phospholipid emulsions with other classes of non-phospholipid surfactant structures, namely polysorbate 80 and poloxamer 188.

References

1. Fox C B. Squalene emulsions for parenteral vaccine and drug delivery. Molecules. 2009; 14:3286-312.
2. Reddy L H, Couvreur P. Squalene: a natural triterpene for use in disease management and therapy. Adv Drug Del Rev. 2009; 61:1412-26.
3. Brito L A, Chan M, Baudner B, Gallorini S, Santos G, O'Hagan D T, et al. An alternative renewable source of squalene for use in emulsion adjuvants. Vaccine. 2011; 29:6262-8.
4. Yang Y W, Wu C A, Morrow W J W. Cell death induced by vaccine adjuvants containing surfactants. Vaccine. 2004; 22:1524-36.
5. Forchielli M L, Bersani G, Tala S, Grossi G, Puggioli C, Masi M. The spectrum of plant and animal sterols in different oil-derived intravenous emulsions. Lipids. 2010; 45:63-71.
6. Vernooij E A A M, Kettens-van den Bosch J J, Crommelin D J A. Rapid determination of acyl chain position in egg phosphatidylcholine by high performance liquid chromatography/electrospray mass spectrometry. Rapid Comm Mass Spec. 1998; 12:83-6.
7. deMan J M. Chemical and physical properties of fatty acids. In: Chow C K, editor. Fatty Acids in Foods and their Health Implications. Boca Raton, Fla.: CRC Press; 2008. p. 17-46.
8. Fox C B, Baldwin S L, Duthie M S, Reed S G, Vedvick T S. Immunomodulatory and physical effects of oil composition in vaccine adjuvant emulsions. Vaccine. 2011; 29:9563-72.
9. Fox C B, Lin S, Sivananthan S J, Dutill T S, Forseth K T, Reed S G, et al. Effects of emulsifier concentration, composition, and order of addition in squalene-phosphatidylcholine oil-in-water emulsions. Pharm Dev Technol. 2011; 16:511-9.

10. Hilleman M R. Personal historical chronicle of six decades of basic and applied research in virology, immunology, and vaccinology. Immunol Rev. 1999; 170:7-27.
11. Rosenberg S A, Yang J C, Kammula U S, Hughes M S, Restifo N P, Schwarz S L, et al. Different adjuvanticity of incomplete Freund's adjuvant derived from beef or vegetable components in melanoma patients immunized with a peptide vaccine. J Immunother. 2010; 33:626-9.
12. Bock T K, Muller B W. A novel assay to determine the hemolytic activity of drugs incorporated in colloidal carrier systems. Pharm Res. 1994; 11:589-91.
13. Baldwin S L, Shaverdian N, Goto Y, Duthie M S, Raman V S, Evers T, et al. Enhanced humoral and Type 1 cellular immune responses with Fluzone adjuvanted with a synthetic TLR4 agonist formulated in an emulsion. Vaccine. 2009; 27:5956-63.
14. Vernooij E A A M, Brouwers J F H M, Kettenes-van den Bosch J J, Crommelin D J A. RP-HPLC/ESI MS determination of acyl chain positions in phospholipids. J Sep Sci. 2002; 25:285-9.
15. Fox C B, Uibel R H, Harris J M. Detecting phase transitions in phosphatidylcholine vesicles by Raman microscopy and self-modeling curve resolution. J Phys Chem B. 2007; 111(39):11428-36.
16. Falsey A R. Half-dose influenza vaccine. Arch Intern Med. 2008; 168:2402-3.
17. Yasuda T, Dancey G F, Kinsky S C. Immunogenicity of liposomal model membranes in mice: Dependence on phospholipid composition. Proc Natl Acad Sci. 1977; 74:1234-6.
18. Baudner B C, Ronconi V, Casini D, Tortoli M, Kazzaz J, Singh M, et al. MF59 emulsion is an effective delivery system for a synthetic TLR4 agonist (E6020). Pharm Res. 2009; 26:1477-85.
19. Mikrut B. Case study: formulation of an intravenous fat emulsion. In: Burgess D J, editor. Injectable Dispersed Systems: Formulation, Processing, and Performance. Boca Raton, Fla.: Taylor and Francis; 2005. p. 415-25.
20. Yoon J K, Burgess D J. Interfacial properties as stability predictors of lecithin-stabilized perfluorocarbon emulsions. Pharm Dev Tech. 1996; 1:333-41.
21. Kabalnov A, Tarara T, Arlauskas R, Weers J. Phospholipids as emulsion stabilizers: phase behavior versus emulsion stability. J Coll Inter Sci. 1996; 184:227-35.
22. Mollet H, Grubenmann A. Formulation Technology: Emulsions, Suspensions, Solid Forms. Verlag: Wiley-VCH; 2001.
23. Nii T, Ishii F. Properties of various phosphatidylcholines as emulsifiers or dispersing agents in microparticle preparations for drug carriers. Coll Surf B: Biointerfaces. 2004; 39(1-2):57-63.
24. Fox C B, Anderson R C, Dutill T S, Goto Y, Reed S G, Vedvick T. Monitoring the effects of component structure and source and formulation stability and adjuvant activity of oil-in-water emulsions. Coll Surf B: Biointerfaces. 2008; 65:98-105.
25. Bibette J, Morse D C, Witten T A, Weitz D A. Stability criteria for emulsions. Phys Rev Lett. 1992; 69(16): 2439.
26. Capek I. Degradation of kinetically-stable o/w emulsions. Adv Coll Inter Sci. 2004; 107(2-3):125-55.
27. Dalgleish D G. Adsorption of protein and the stability of emulsions. Trends Food Sci Tech. 1997; 8(1):1-6.
28. McClements D J. Critical review of techniques and methodologies for characterization of emulsion stability. Crit Rev Food Sci Nutri. 2007; 47:611-49.
29. Tatulian S A. Binding of alkaline-earth metal cations and some anions to phosphatidylcholine liposomes. Eur J Biochem. 1987; 170:413-20.
30. Tatulian S A. Effect of lipid phase transition on the binding of anions to dimyristoylphosphatidylcholine liposomes. Biochim Biophys Acta. 1983; 736:189-95.
31. Tanaka Y, Mashino K, Inoue K, Nojima S. Mechanism of human erythrocyte hemolysis induced by short-chain phosphatidylcholines and lysophosphatidylcholine. J Biochem. 1983; 94:833-40.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An oil-in-water emulsion comprising a TLR4 agonist, 1,2-dimyristoyl-sn-glycero-3-phosphocholine (DMPC), and a metabolizable oil, wherein the TLR4 agonist comprises synthetic GLA, wherein the metabolizable oil is present in the oil-in-water emulsion at a concentration of 0.01%-1% v/v, wherein the DMPC is present in the oil-and-water emulsion at a concentration of 0.002% to 2% w/v, and wherein the hydrophobic:lipophilic balance (HLB) of the oil-in-water emulsion is greater than about 9.

2. The oil-in-water emulsion of claim 1, wherein the metabolizable oil is present in the oil-in-water emulsion at a concentration of 0.01%- 0.5% v/v.

3. The oil-in-water emulsion of claim 1, wherein the emulsion does not comprise egg phosphatidyl choline (PC).

4. The oil-in-water emulsion of claim 3, wherein the emulsion does not comprise an antioxidant.

5. The oil-in-water emulsion of claim 1, wherein the HLB of the emulsion is greater than about 10.

6. The oil-in-water emulsion of claim 1, wherein the HLB of the emulsion is between about 9-12.

7. The oil-in-water emulsion of claim 1, wherein the synthetic GLA has the following structure:

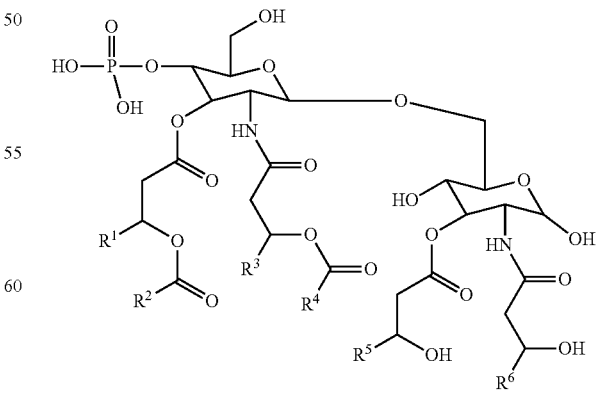

where: $R^1$, $R^3$, $R^5$, and $R^6$ are $C_{11}$-$C_{20}$ alkyl; and $R^2$ and $R^4$ are $C_{12}$-$C_{20}$ alkyl.

8. The oil-in-water emulsion of claim 7, wherein $R^1$, $R^3$, $R^5$, and $R^6$ are $C_{11}$ alkyl; and $R^2$ and $R^4$ are $C_{13}$ alkyl.

9. The oil-in-water emulsion of claim 1, wherein the synthetic GLA has the following structure:

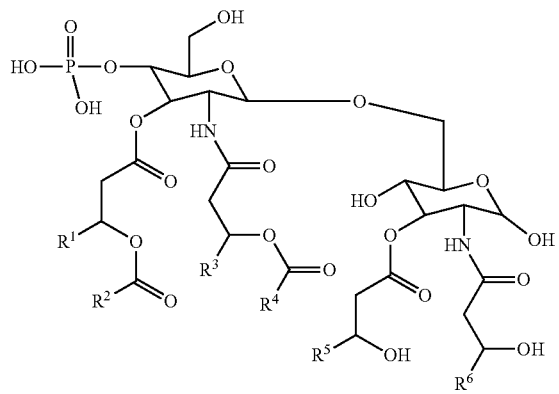

wherein $R^1$, $R^3$, $R^5$, and $R^6$ are $C_{10}$ alkyl; and $R^2$ and $R^4$ are $C_8$ alkyl.

10. The oil-in-water emulsion of claim 1, wherein the emulsion further comprises a surfactant.

11. The oil-in-water emulsion of claim 10, wherein the surfactant is pluronic F68.

12. The oil-in-water emulsion of claim 1, wherein the metabolizable oil is squalene.

13. The oil-in-water emulsion of claim 1, wherein the emulsion further comprises an antioxidant.

14. The oil-in-water emulsion of claim 13, wherein the antioxidant is vitamin E.

15. The oil-in-water emulsion of claim 1, wherein the emulsion further comprises at least one antigen.

16. An oil-in-water emulsion comprising a synthetic GLA, a metabolizable oil at a concentration of 0.01%-1% v/v, and DMPC at a concentration of 0.002%-2% w/v, wherein the HLB of the emulsion is greater than about 10.

17. The oil-in-water emulsion of claim 16, wherein the synthetic GLA has the following structure:

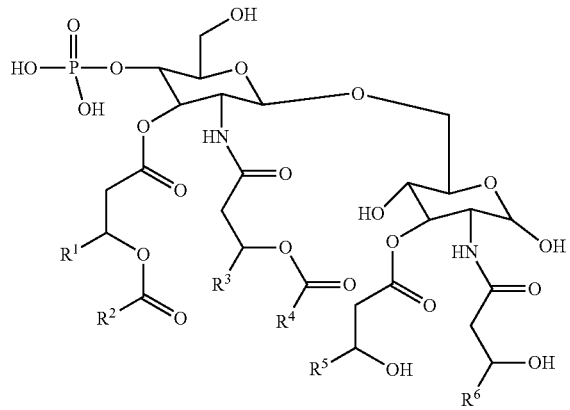

where: $R^1$, $R^3$, $R^5$, and $R^6$ are $C_{11}$-$C_{20}$ alkyl; and $R^2$ and $R^4$ are $C_{12}$-$C_{20}$ alkyl.

18. The oil-in-water emulsion of claim 17, wherein $R^1$, $R^3$, $R^5$, and $R^6$ are $C_{11}$ alkyl; and $R^2$ and $R^4$ are $C_{13}$ alkyl.

19. The oil-in-water emulsion of claim 16, wherein the synthetic GLA has the following structure:

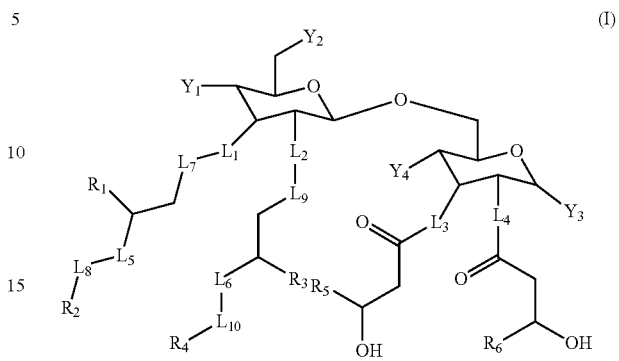

or a pharmaceutically acceptable salt thereof, wherein:
$L_1$, $L_2$, $L_3$, $L_4$, $L_5$, and $L_6$ are the same or different and independently -O-, -NH- or -(CH$_2$)-$L_7$,
$L_8$, $L_9$, and $L_{10}$ are the same or different and independently absent or -C(=O)—; $Y_1$ is an acid functional group;
$Y_2$ and $Y_3$ are the same or different and independently —OH, —SH, or an acid functional group;
$Y_4$ is —OH or —SH;
$R_1$, $R_3$, $R_5$, and $R_6$ are the same or different and independently $C_{8-13}$ alkyl; and
$R_2$ and $R_4$ are the same or different and independently $C_{6-11}$ alkyl.

20. The oil-in-water emulsion of claim 19, wherein $R^1$, $R^3$, $R^5$, and $R^6$ are $C_{11}$ alkyl; and $R^2$ and $R^4$ are $C_8$ alkyl.

21. A method of stimulating an immune response in a subject comprising administering an oil-in-water emulsion of claim 1 to the subject and thereby stimulating an immune response in the subject.

22. The method of claim 21, wherein the immune response is a non-specific immune response.

23. The method of claim 21, wherein the immune response is an antigen-specific immune response.

24. The method of claim 21, wherein the oil-in-water emulsion is administered intradermally.

25. The oil-in-water emulsion of claim 1, wherein the synthetic GLA has the following structure:

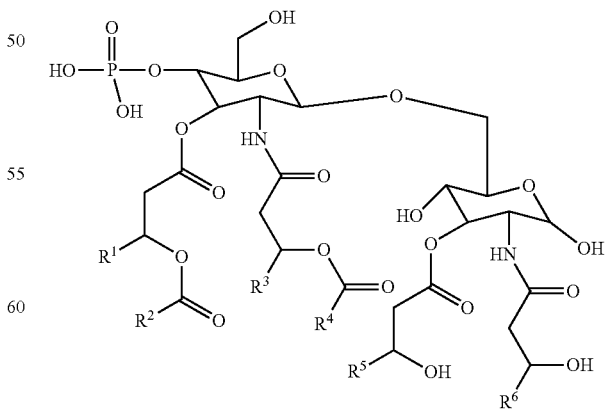

or a pharmaceutically acceptable salt thereof, wherein: $R^1$, $R^3$, $R^5$, and $R^6$ are $C_{11-20}$ alkyl; and $R^2$ and $R^4$ are $C_{9-20}$ alkyl.

26. The oil-in-water emulsion of claim 1, wherein the synthetic GLA has the following structure:

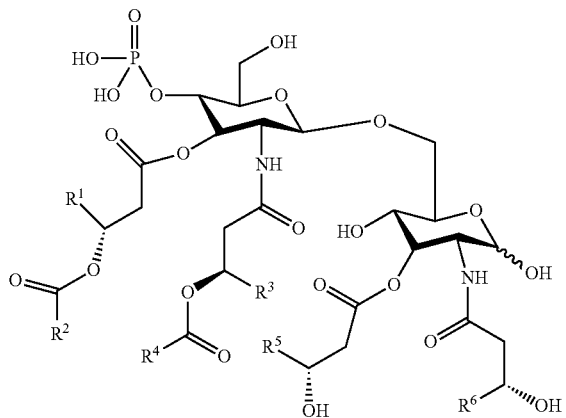

or a pharmaceutically acceptable salt thereof, wherein: $R^1$, $R^3$, $R^5$, and $R^6$ are $C_{11}$-$C_{20}$ alkyl; and $R^2$ and $R^4$ are $C_9$-$C_{20}$ alkyl.

27. The oil-in-water emulsion of claim 1, wherein the synthetic GLA has the following structure:

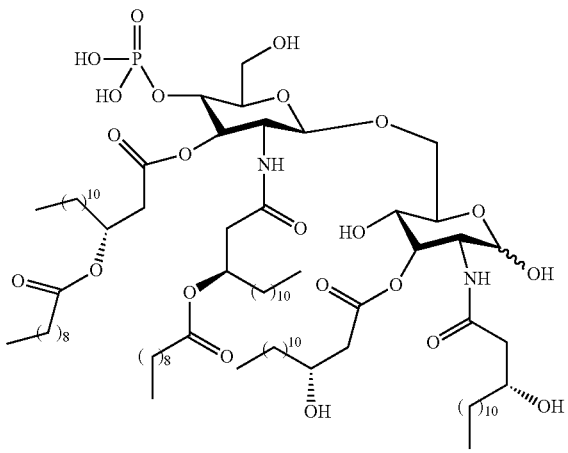

or a pharmaceutically acceptable salt thereof.

28. The oil-in-water emulsion of claim 16, wherein the synthetic GLA has the following structure:

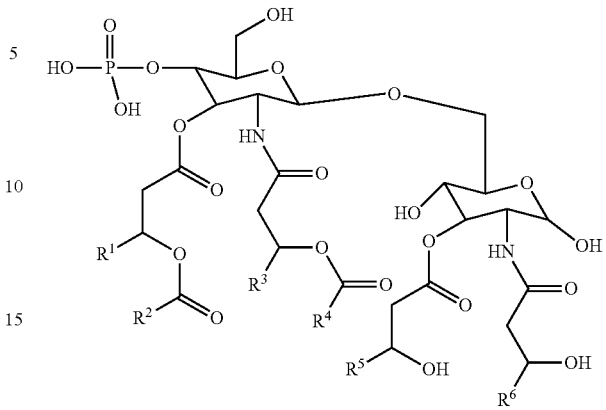

or a pharmaceutically acceptable salt thereof, wherein: $R^1$, $R^3$, $R^5$, and $R^6$ are $C_{11-20}$ alkyl; and $R^2$ and $R^4$ are $C_{9-20}$ alkyl.

29. The oil-in-water emulsion of claim 16, wherein the synthetic GLA has the following structure:

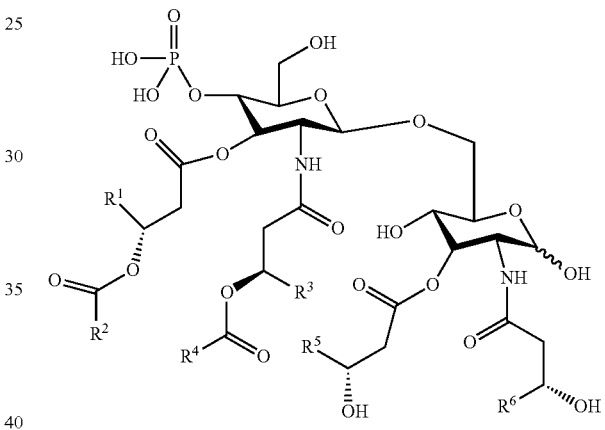

or a pharmaceutically acceptable salt thereof, wherein: $R^1$, $R^3$, $R^5$, and $R^6$ are $C_{11}$-$C_{20}$ alkyl; and $R^2$ and $R^4$ are $C_9$-$C_{20}$ alkyl.

30. The oil-in-water emulsion of claim 16, wherein the synthetic GLA has the following structure:

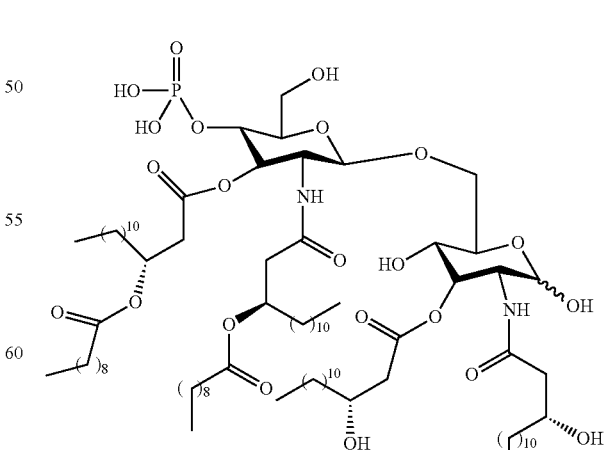

or a pharmaceutically acceptable salt thereof.

31. An oil-in-water emulsion comprising a metabolizable oil and DMPC (1,2-dimyristoyl-sn-glycero-3-phosphocholine), wherein the DMPC is present in the oil-and-water emulsion at a concentration of 0.002% to 2% w/v and wherein the emulsion does not comprise egg phosphatidyl choline (PC).

32. The oil-in-water emulsion of claim 31, wherein the metabolizable oil is present in the oil-in-water emulsion at a concentration of 0.01%-4% v/v.

33. The oil-in-water emulsion of claim 31, wherein the emulsion does not comprise an antioxidant.

34. The oil-in-water emulsion of claim 31, wherein a hydrophobic:lipophilic balance (HLB) of the emulsion is greater than about 10.

35. The oil-in-water emulsion of claim 31, wherein a hydrophobic:lipophilic balance (HLB) of the emulsion is between about 9-12.

36. The oil-in-water emulsion of claim 31, further comprising a TLR4 agonist.

37. The oil-in-water emulsion of claim 36, wherein the TLR4 agonist comprises MPL, 3D-MPL, or synthetic GLA.

38. The oil-in-water emulsion of claim 37, wherein the synthetic GLA has the following structure:

[chemical structure]

where: $R^1$, $R^3$, $R^5$, and $R^6$ are $C_{11}$-$C_{20}$ alkyl; and $R^2$ and $R^4$ are $C_{12}$-$C_{20}$ alkyl.

39. The oil-in-water emulsion of claim 38, wherein $R^1$, $R^3$, $R^5$, and $R^6$ are $C_{11}$ alkyl; and $R^2$ and $R^4$ are $C_{13}$ alkyl.

40. The oil-in-water emulsion of claim 37, wherein the synthetic GLA has the following structure:

[chemical structure]

or a pharmaceutically acceptable salt thereof, wherein: $R^1$, $R^3$, $R^5$, and $R^6$ are $C_{11\text{-}20}$ alkyl; and $R^2$ and $R^4$ are $C_{12\text{-}20}$ alkyl.

41. The oil-in-water emulsion of claim 31, wherein the emulsion further comprises a surfactant.

42. The oil-in-water emulsion of claim 41, wherein the surfactant is pluronic F68.

43. The oil-in-water emulsion of claim 31, wherein the metabolizable oil is squalene.

44. The oil-in-water emulsion of claim 31, wherein the emulsion further comprises an antioxidant.

45. The oil-in-water emulsion of claim 44, wherein the antioxidant is vitamin E.

46. The oil-in-water emulsion of claim 31, wherein the emulsion further comprises at least one antigen.

47. A method of stimulating an immune response in a subject comprising administering an oil-in-water emulsion of claim 31 to the subject and thereby stimulating an immune response in the subject.

48. The method of claim 47, wherein the immune response is a non- specific immune response.

49. The method of claim 47, wherein the immune response is an antigen-specific immune response.

50. The method of claim 47, wherein the oil-in-water emulsion is administered intradermally.

51. The oil-in-water emulsion of claim 31, wherein the DMPC is present in the oil-in-water emulsion at a concentration of 0.015% to 0.25% w/v.

52. The oil-in-water emulsion of claim 32, wherein the metabolizable oil is squalene.

53. The oil-in-water emulsion of claim 36, wherein the metabolizable oil is squalene.

54. The oil-in-water emulsion of claim 51, wherein the metabolizable oil is squalene.

55. The oil-in-water emulsion of claim 16, wherein the metabolizable oil is squalene.

56. A method of stimulating an immune response in a subject comprising administering an oil-in-water emulsion of claim 16 to the subject and thereby stimulating an immune response in the subject.

57. The method of claim 56, wherein the immune response is a non-specific immune response.

58. The method of claim 56, wherein the immune response is an antigen-specific immune response.

59. The method of claim 56, wherein the oil-in-water emulsion is administered intradermally.

60. The oil-in-water emulsion of claim 37, wherein the TLR4 agonist comprises synthetic GLA.

61. The oil-in-water emulsion of claim 31, wherein a hydrophobic:lipophilic balance (HLB) of the emulsion is greater than about 9.

* * * * *